(12) United States Patent
Holt et al.

(10) Patent No.: US 8,436,183 B2
(45) Date of Patent: *May 7, 2013

(54) SYNTHETIC MULTIMERIZING AGENTS

(75) Inventors: Dennis A. Holt, Royersford, PA (US); Terence P. Keenan, Bay Shore, NY (US); Tao Guo, Dayton, NJ (US); Edgardo Laborde, Foster City, CA (US); Wu Yang, Princeton, NJ (US)

(73) Assignee: ARIAD Pharmaceuticals, Inc., Cambridge, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/361,082

(22) Filed: Jan. 30, 2012

(65) Prior Publication Data

US 2012/0130076 A1    May 24, 2012

Related U.S. Application Data

(63) Continuation of application No. 10/461,705, filed on Jun. 13, 2003, now Pat. No. 8,106,191, which is a continuation of application No. 10/086,770, filed on Feb. 28, 2002, now abandoned, which is a continuation of application No. 09/690,581, filed on Oct. 17, 2000, now abandoned, which is a continuation of application No. 08/808,274, filed on Feb. 28, 1997, now Pat. No. 6,150,527, which is a continuation-in-part of application No. 08/793,016, filed on Dec. 1, 1997, now abandoned, and a continuation-in-part of application No. 08/479,694, filed on Jun. 7, 1995, now abandoned, which is a continuation-in-part of application No. 08/292,598, filed on Aug. 18, 1994, now abandoned.

(60) Provisional application No. 60/033,035, filed on Dec. 10, 1996, provisional application No. 60/024,861, filed on Aug. 28, 1996, provisional application No. 60/012,432, filed on Feb. 28, 1996.

(51) Int. Cl.
*C07D 211/06* (2006.01)
*C07D 211/60* (2006.01)
*C07D 401/00* (2006.01)
*C07D 207/00* (2006.01)

(52) U.S. Cl.
USPC ...................................................... 546/189

(58) Field of Classification Search ............. 546/189
See application file for complete search history.

(56) References Cited

U.S. PATENT DOCUMENTS

| | | |
|---|---|---|
| 5,120,727 A | 6/1992 | Kao et al. |
| 5,162,333 A | 11/1992 | Failli et al. |
| 5,192,773 A | 3/1993 | Armistead et al. |
| 5,225,528 A | 7/1993 | Bock et al. |
| 5,304,642 A | 4/1994 | Bastart et al. |
| 5,620,971 A | 4/1997 | Armistead et al. |
| 5,622,970 A | 4/1997 | Armistead et al. |
| 5,717,092 A | 2/1998 | Armistead et al. |
| 5,744,485 A | 4/1998 | Zelle et al. |
| 5,780,484 A | 7/1998 | Zelle et al. |
| 5,811,434 A | 9/1998 | Zelle et al. |
| 5,830,462 A | 11/1998 | Crabtree et al. |
| 5,834,266 A | 11/1998 | Crabtree et al. |
| 5,871,753 A | 2/1999 | Crabtree et al. |
| 5,994,313 A | 11/1999 | Crabtree et al. |
| 6,133,456 A | 10/2000 | Holt et al. |
| 6,150,527 A * | 11/2000 | Holt et al. ............... 546/189 |

FOREIGN PATENT DOCUMENTS

| | | |
|---|---|---|
| EP | 0133098 | 2/1985 |
| WO | WO 96/06097 | 2/1996 |

OTHER PUBLICATIONS

Babine et al., "Molecular Recognition of Protein-Ligand Complexes: Applications to Drug Design", Chem. Rev., (1997), vol. 97, pp. 1359-1472.
Holt et al., "Design, Synthesis and Kinetic Evaluation . . . of Their Complexes with FKBP12", J. Am. Chem. Soc., (1993), vol. 115, pp. 9925-9938.
Holt et al., "Structure-Activity Studies of Synthetic FKBP Ligands as Peptidyl-prolyl Isomerase Inhibitors", Bioorganic & Medicinal Chem. Letters, vol. 4, No. 2, pp. 315-320, 1994.
Katritzky et al., "Handbook of Heterocyclic Chemistry", Pergamon Press (1985), see pp. 151, 298 & 307.
Luengo et al., "Synthesis and Structure-Activity Relationships of Macrocyclic FKBP Ligands", Bioorganic & Medicinal Chem Letters, vol. 4, No. 2, pp. 321-324, 1994.
Spencer et al., "Controlling Signal Transduction with Synthetic Ligands", Science, (1993), 262, pp. 1019-1024.
Uchiyama et al., "Synthesis of Hybrid Type of Anti-HIV Drugs", Peptide Chemistry, (1993), vol. 31, pp. 89-92.
Wang et al., "Synthesis and FKBP Binding of Small Molecule Mimics of the Tricarbonyl Region of FK506", Bioorganic & Medicinal Chem Letters, (1994),vol. 4, No. 9, pp. 1161-1166.
Yamashita et al, "Design, Synthesis and Evaluation of Dual Domain FKBP Ligands", Bioorganic & Medicinal Chem Letters, (1994), vol. 4, No. 2, pp. 325-328.
Cas Online Printout for Boger et al, "-(−)Sandramycin: Total synthesis and preliminary DNA binding properties", Jrl of the Amer Chem Soc, (1993) vol. 115, No. 24, pp. 11624-11625.
CAS Online Printout for Maurer et al., "Separation of Actinomycins and . . . High Performance Liquid Chromatography", J of Antibiotics, (1990), vol. 42, No. 2, pp. 220-221.
CAS Online Printout for Williams et al., "Development of novel class of cyclic . . . based on a natural product", J of Medicinal Chem, (1992), vol. 35, No. 21, pp. 3905-3918.
CASs Online Printout for EP 0 444 898, Sep. 4, 1991.
STN printout of Registry No. 32934-49-9. (1999).

* cited by examiner

*Primary Examiner* — Brenda Coleman
(74) *Attorney, Agent, or Firm* — David L. Berstein

(57) ABSTRACT

New compounds are disclosed for multimerizing immunophilins and proteins containing immunophilin or immunophilin-related domains. The compounds are of the formula

M-L-Q where M is a synthetic ligand for an FKBP protein.

2 Claims, No Drawings

US 8,436,183 B2

SYNTHETIC MULTIMERIZING AGENTS

CROSS-REFERENCE TO RELATED APPLICATIONS

The present application is a continuation of U.S. Ser. No. 10/461,705 filed on Jun. 13, 2003, which is a continuation of U.S. Ser. No. 10/086,770 filed on Feb. 28, 2002 (now abandoned), which is a continuation of U.S. Ser. No. 09/690,581 filed Oct. 17, 2000 (now abandoned), which is a continuation of U.S. Ser. No. 08/808,274 filed Feb. 28, 1997 (now U.S. Pat. No. 6,150,527), the full contents of which are hereby incorporated herein by reference. U.S. Ser. No. 08/808,274 filed Feb. 28, 1997 (now U.S. Pat. No. 6,150,527) is itself a continuation-in-part of each of the following applications, the full contents of which are also expressly incorporated herein by reference: U.S. Ser. No. 60/033,035 filed Dec. 10, 1996; U.S. Ser. No. 60/024,861 filed Aug. 28, 1996; U.S. Ser. No. 60/012,432 filed Feb. 28, 1996; U.S. Ser. No. 08/793,016 filed Aug. 18, 1995 (now abandoned); and U.S. Ser. No. 08/479,694 filed Jun. 7, 1995 (now abandoned) which is a continuation-in-part of U.S. Ser. No. 08/292,598 filed Aug. 18, 1994 (now abandoned). This application also claims the priority of U.S. Ser. No. 08/808,276 filed Feb. 28, 1997 (now U.S. Pat. No. 6,133,456). The entire contents of each of the foregoing applications are hereby incorporated by reference in their entirety.

BACKGROUND OF THE INVENTION

Identification of the immunophilin protein, FKBP12, as a specific receptor for the powerful immunosuppressant drug, FK506, led to a burst of pharmaceutical research over the past decade. Much of that research was aimed at the discovery of other high affinity ligands for FKBP which might become clinically and commercially significant immunosuppressant agents. A variety of synthetic FKBP ligands were produced and evaluated, but with disappointing results. In the early 1990's it was learned that FK506 works, not simply by binding to FKBP, but by mediating the association of FKBP with the effector protein, calcineurin, to form the tripartite complex which actually mediates immunosuppression. This finding explained the absence of immunosuppressive activity for the many high-affinity FKBP ligands which are now known in the art. A body of synthetic knowledge pertaining to the design and synthesis of FKBP ligands had been developed which appeared destined to lie fallow. See e.g., U.S. Pat. Nos. 5,192,773; 5,330,993; WO 92/19593; and WO 94/07858.

Largely independent of the search for new immunosuppressive agents, however, pioneering work on the design, production and use of biological switches based on ligand-mediated multimerization of recombinant proteins, including immunophilin-based fusion proteins, was reported. See Spencer et al, 1993, Science 262:1019-1024 and International Patent Applications PCT/US94/01660 and PCT/US94/08008. Spencer et al reported a new class of biologically active substances based on dimers of FK506, covalently attached to each other via a synthetic linker moiety. The resultant dimers ("FK1012" molecules) are characterized by high binding affinities for immunophilin molecules and are capable of mediating the association or complexation of fusion proteins containing FKBP domains. However, FK1012 and related semisynthetic multimerizing agents are large, complex molecules which can be inconvenient to produce.

New methods and materials for multimerizing chimeric proteins containing immunophilin moieties would be desirable, where the methods and materials involve smaller, simpler multimerizing agents which are more convenient to produce and which are more readily amenable to structural modification.

Important initial research based on N-oxalyl-pipecolyl and N-oxalyl-prolyl ligand moieties and aimed at providing wholly synthetic replacements for FK1012-type semi-synthetic multimerizing agents was disclosed in PCT/US95/10559. Further progress in this direction, including new multimerizing agents e.g. which are more conveniently prepared, have alternative pharmacokinetic profiles and/or which bind preferentially or with higher affinity to genetically engineered immunophilin domains relative to their binding to native immunophilin proteins would be very desirable.

DESCRIPTION OF THE INVENTION

This invention provides new materials and methods based on N-acyl-pipecolyl and N-acyl-prolyl ligand moieties for multimerizing chimeric proteins containing immunophilin-derived domains. The design and expression of fusion proteins containing a ligand-binding domain such as an FKBP domain and one or more effector domains has been reported, inter alia, in Spencer et al and in the international patent applications cited above in connection with Spencer et al, the full contents of all of which are incorporated herein by reference. Numerous other accounts of successful application of this technology have also been reported. Essentially, the fusion proteins are designed such that association of the effector domains, through ligand-mediated "dimerization" or "multimerization" of the fusion proteins which contain them, triggers a desired biological event such as transcription of a desired gene, cell death, cell proliferation, etc. "Multimerization" as the term is used herein encompasses dimerization and higher order multimerization. In many such accounts, the ligand-binding domain of at least one of the fusion proteins is an FKBP domain. For further information and guidance on the design, construction and practice of such systems or components thereof, reference to the following publications is suggested: Spencer et al, 1993, supra; Rivera et al, 1996, Nature Medicine 2, 977-978; Spencer et al, 1996, Current Biology 6, 839-847; Luo et al, 1996, Nature, 383, 181-185; Ho et al, 1996, Nature 382, 822-826; Belshaw et al, 1996, Proc., Natl. Acad. Sci. USA 93, 4604-4607; Spencer, 1996, TIG 12(5), 181-187; Spencer et al, 1995, Proc., Natl. Acad. Sci. USA 92, 9805-9809; Holsinger et al, 1995, Proc., Natl. Acad. Sci. USA 92, 9810-9814; Pruschy et al, 1994, Chemistry & Biology 1(3), 163-172; and published international patent applications WO 94/18317, WO 95/02684, WO 96/20951 and WO 96/41865.

The main focus of the subject invention is a new class of multimerizing agents which are useful as mediators of such protein-protein interactions in applications using fusion proteins containing FKBP domains. In some cases, the FKBP domains are genetically engineered, for instance, to replace the phenylalanine residue at position 36 with an amino acid having a less bulky R group, e.g. valine, alanine, methionine, etc. These multimerizing agents may be used in the various applications of the underlying dimerization-based technology, including triggering biological events in genetically engineered cells grown or maintained in culture or present in whole organisms, including humans and other mammals. The multimerizing agents may thus be useful as research reagents in biological experiments in vitro, in experiments conducted on animals containing the genetically engineered cells, and as prophylactic or therapeutic agents in animal and human healthcare in subjects containing genetically engineered cells.

Multimerizing Agents

The invention relates to immunophilin-multimerizing agents of formula I

M-L-Q                    I and pharmaceutically acceptable salts thereof, including their individual stereoisomers and mixtures of stereoisomers, where M is an immunophilin-binding group comprising a moiety of formula II:

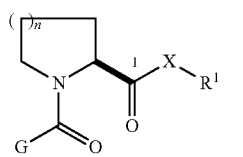

II

Where G is independently selected from the group consisting of:

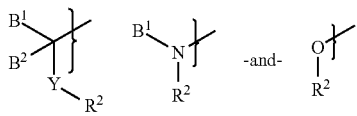

as defined below.

Q is also a moiety of formula II, or is a naturally occurring FKBP ligand such as FK506 or FK520, or is a synthetic FKBP ligand, e.g. as disclosed in PCT/US95/10559; Holt, et al., *J. Amer. Chem. Soc.*, 1993, 115, 9925-9938; Holt, et al., *Biomed. Chem. Lett.*, 1993, 4, 315-320; Luengo, et al., *Biomed. Chem. Lett.*, 1993, 4, 321-324; Yamashita, et al., *Biomed. Chem. Lett.*, 1993, 4, 325-328; Spencer et al, above; PCT/US94/01617; PCT/US94/08008. See also EP 0 455 427 A1; EP 0 465 426 A1; U.S. Pat. No. 5,023,263 and WO 92/00278. As disclosed in greater detail in PCT/US95/10559, synthetic FKBP ligands of formula III

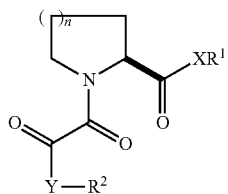

III (where R1, R2 and n may be selected from the definitions provided below) may be readily prepared and multimerized by covalent attachment to linker moiety.

In embodiments of the invention where Q is a moiety of formula II, the multimerizing agent will be of the formula

M¹-L-M²                   IV where M¹ and M² are independently selected from moieties of formula II, and thus may be the same or different.

Multimerizing agents of formula I comprise at least one, and in currently preferred embodiments, two moieties (M¹ and M²) which are independently selected from the group consisting of:

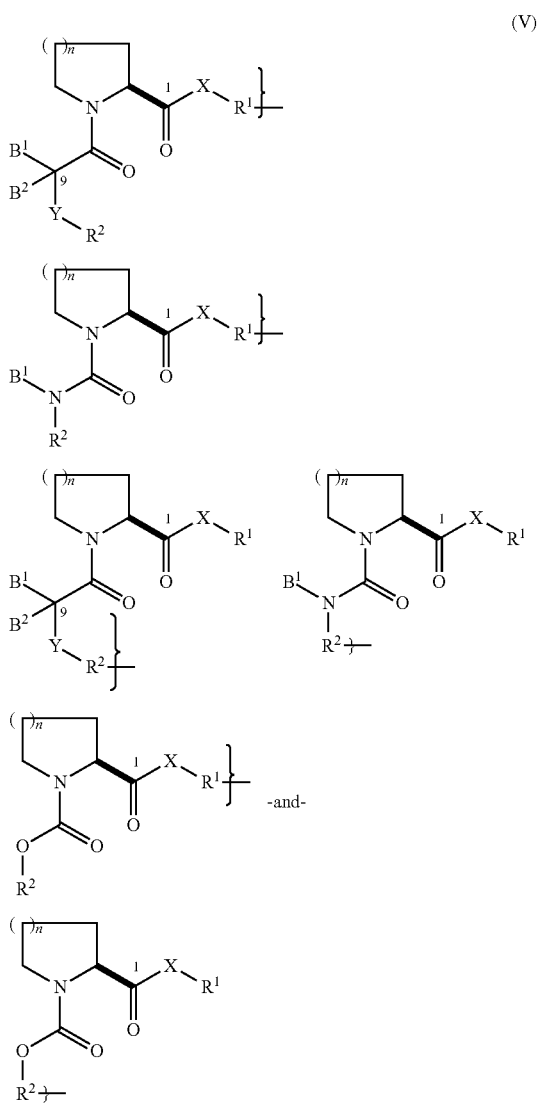

(V)

and include the following exemplary (and non-exclusive) classes:

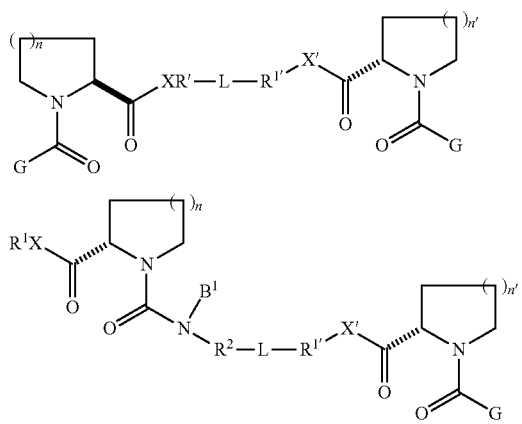

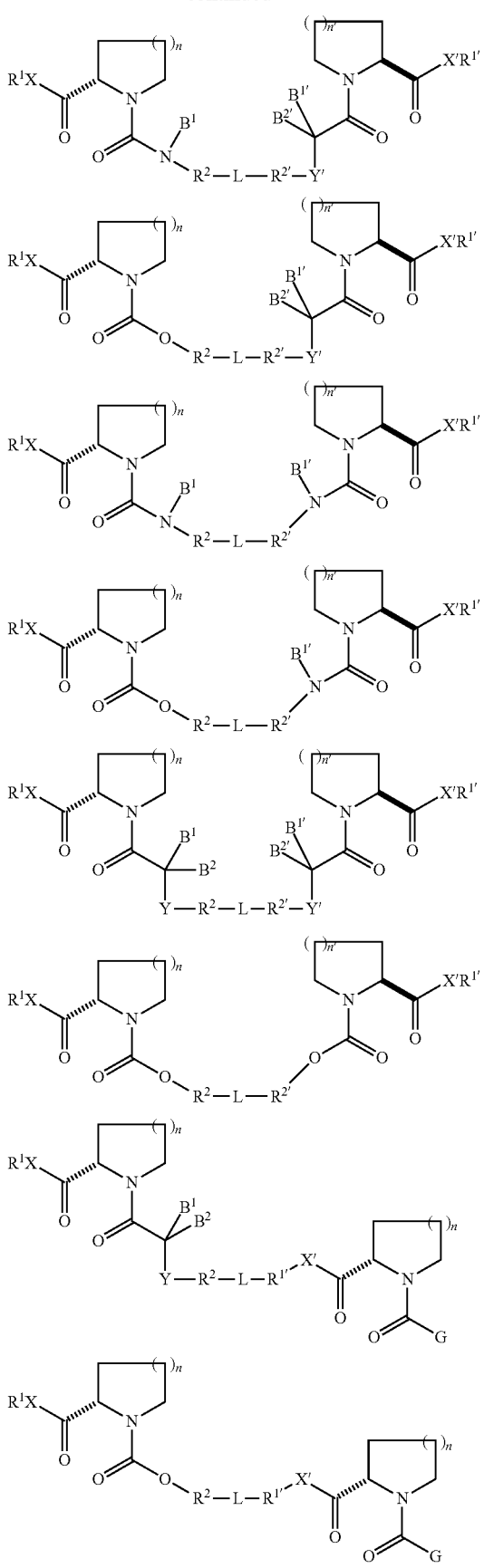

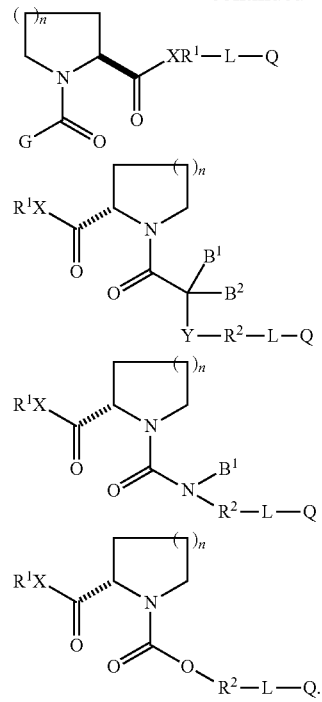

In the foregoing formulas, the following definitions apply:

n=1 or 2;

X=O, NH or CH$_2$;

B$^1$ and B$^2$ are independently H or aliphatic, heteroaliphatic, aryl or heteroaryl as those terms are defined below, usually containing one to about 12 carbon atoms (not counting carbon atoms of optional substituents);

Y=O, S, NH, —NH(C=O)—, —NH(C=O)—O—, —NH(SO$_2$)— or NR$^3$, or represents a direct, i.e. covalent, bond from R$^2$ to carbon 9;

R$^1$, R$^2$, and R$^3$ are aliphatic, heteroaliphatic, aryl or heteroaryl, usually containing one to about 36 carbon atoms (not counting carbon atoms of optional substituents);

two or more of B$^1$, B$^2$ and R$^2$ may be covalently linked to form a C3-C7 cyclic or heterocyclic moiety; and, L is a linker moiety covalently linking monomers M to Q or covalently linking M$^1$ to M$^2$ through covalent bonds to either R$^1$ or R$^2$, not necessarily the same in each of M$^1$ and M$^2$.

The term "aliphatic" as used herein includes both saturated and unsaturated straight chain, branched, cyclic, or polycyclic aliphatic hydrocarbons, which are optionally substituted with one or more functional groups selected from the group consisting of hydroxy, alkoxy, acyl, carbamoyl, amino, alkylamino, dialkylamino, N-acylamino, keto, halo, trihalomethyl, cyano, carboxyl, aryl, heteroaryl, heterocyclic or sulfonamido (unless otherwise specified, the alkyl, other aliphatic, alkoxy and acyl groups preferably contain 1-8, and in many cases 1-6, contiguous aliphatic carbon atoms).

The term "aliphatic" is thus intended to include alkyl, alkenyl, alkynyl, cycloalkyl, cycloalkenyl, and cycloalkynyl moieties.

As used herein, the term "alkyl" includes both straight and branched alkyl groups. An analogous convention applies to other generic terms such as "alkenyl", "alkynyl" and the like. Furthermore, as used herein, the language "alkyl", "alkenyl", "alkynyl" and the like encompasses both substituted and unsubstituted groups.

The term "alkyl" refers to groups usually having one to eight, preferably one to six carbon atoms. For example, "alkyl" may refer to methyl, ethyl, n-propyl, isopropyl, butyl, isobutyl, sec-butyl, tert-butyl, pentyl, isopentyl tert-pentyl, hexyl, isohexyl, and the like. Suitable substituted alkyls include, but are not limited to, fluoromethyl, difluoromethyl, trifluoromethyl, 2-fluoroethyl, 3-fluoropropyl, hydroxymethyl, 2-hydroxyethyl, 3-hydroxypropyl, and the like.

The term "alkenyl" refers to groups usually having two to eight, preferably two to six carbon atoms. For example, "alkenyl" may refer to prop-2-enyl, but-2-enyl, but-3-enyl, 2-methylprop-2-enyl, hex-2-enyl, hex-5-enyl, 2,3-dimethylbut-2-enyl, and the like. The language "alkynyl," which also refers to groups having two to eight, preferably two to six carbons, includes, but is not limited to, prop-2-ynyl, but-2-ynyl, but-3-ynyl, pent-2-ynyl, 3-methylpent-4-ynyl, hex-2-ynyl, hex-5-ynyl, and the like.

The term "cycloalkyl" as used herein refers to groups having three to seven, preferably three to six carbon atoms. Suitable cycloalkyls include, but are not limited to cyclopropyl, cyclobutyl, cyclopentyl, cyclohexyl, cycloheptyl and the like.

The term "heteroaliphatic" as used herein refers to aliphatic moieties which contain one or more oxygen, sulfur, or nitrogen atoms, e.g., in place of carbon atoms.

The language "heterocycle" as used herein refers to cyclic aliphatic groups having one or more heteroatoms, and preferably three to seven ring atoms total, includes, but is not limited to oxetane, tetrahydrofuranyl, tetrahydropyranyl, aziridine, azetidine, pyrrolidine, piperidine, morpholine, piperazine and the like.

The terms "aryl" and "heteroaryl" as used herein refer to stable mono- or polycyclic, heterocyclic, polycyclic, and polyheterocyclic unsaturated moieties having 3-14 carbon atom which may be substituted or unsubstituted. Non-limiting examples of useful aryl ring groups include phenyl, halophenyl, alkoxyphenyl, dialkoxyphenyl, trialkoxyphenyl, alkylenedioxyphenyl, naphthyl, phenanthryl, anthryl, phenanthro and the like. Examples of typical heteroaryl rings include 5-membered monocyclic ring groups such as thienyl, pyrrolyl, imidazolyl, pyrazolyl, furyl, isothiazolyl, furazanyl, isoxazolyl, thiazolyl and the like; 6-membered monocyclic groups such as pyridyl, pyrazinyl, pyrimidinyl, pyridazinyl, triazinyl and the like; and polycyclic heterocyclic ring groups such as benzo[b]thienyl, naphtho[2,3-b]thienyl, thianthrenyl, isobenzofuranyl, chromenyl, xanthenyl, phenoxathienyl, indolizinyl, isoindolyl, indolyl, indazolyl, purinyl, isoquinolyl, quinolyl, phthalazinyl, naphthyridinyl, quinoxalinyl, quinazolinyl, benzothiazole, benzimidazole, tetrahydroquinoline cinnolinyl, pteridinyl, carbazolyl, beta-carbolinyl, phenanthridinyl, acridinyl, perimidinyl, phenanthrolinyl, phenazinyl, isothiazolyl, phenothiazinyl, phenoxazinyl, and the like (see e.g. Katritzky, Handbook of Heterocyclic Chemistry). The aryl or heteroaryl moieties may be substituted with one to five members selected from the group consisting of hydroxy, $C_1$-$C_8$ alkoxy, $C_1$-$C_8$ branched or straight-chain alkyl, acyloxy, carbamoyl, amino, N-acylamino, nitro, halo, trihalomethyl, cyano, and carboxyl.

A "halo" substituent according to the present invention may be a fluoro, chloro, bromo or iodo substituent.

As discussed above, $R^1$ may be aliphatic, heteroaliphatic, aryl or heteroaryl and usually comprises one to about 36 carbon atoms, exclusive of optional substituents.

In certain embodiments, $R^1$ is optionally be joined, i.e., covalently linked, to $R^2$, $B^1$ or $B^2$, forming a macrocyclic structure as indicated by the dashed line in the illustrative structures below:

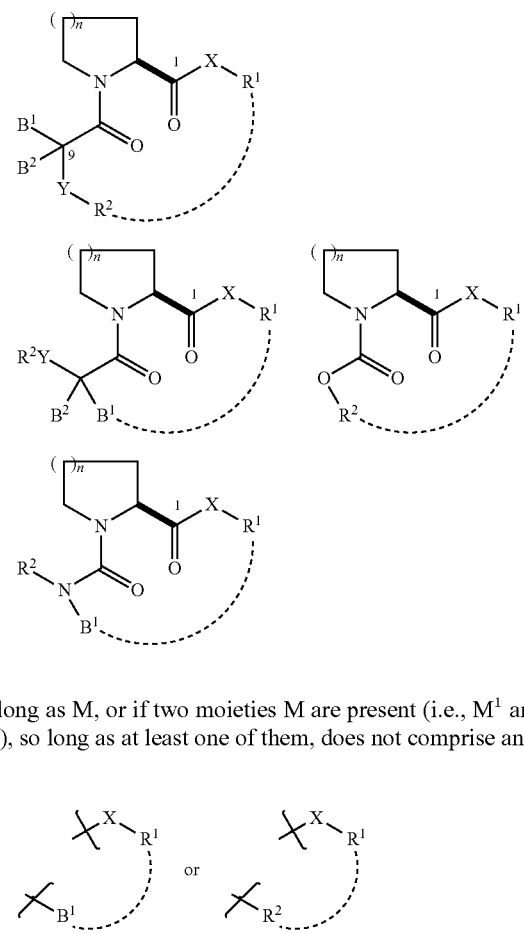

so long as M, or if two moieties M are present (i.e., $M^1$ and $M^2$), so long as at least one of them, does not comprise an

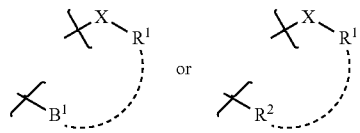

group comprising the following moiety found in FK506 and related natural products such as FK520:

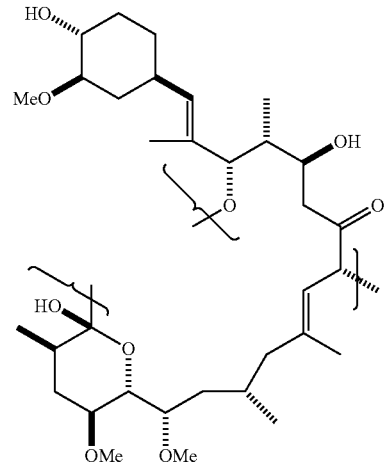

Currently, non-macrocyclic monomers M are of particular interest.

In certain preferred embodiments —$XR^1$ is a moiety of the formula

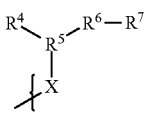

where $R^4$ is a H, aliphatic, heteroaliphatic, aryl or heteroaryl. The aliphatic moieties may be branched, unbranched, cyclic, saturated or unsaturated, substituted or unsubstituted and include, e.g, methyl, ethyl, isopropyl, t-butyl, cyclopentyl, cyclohexyl, etc. Heteroaliphatic moieties may be branched, unbranched or cyclic and include heterocycles such as morpholino, pyrrolidinyl, etc. Illustrative ortho-, meta- or para-, substitutents for a phenyl group at this position include one or more of the following: halo, e.g. chloro or fluoro; hydroxyl, amino, —$SO_2NH_2$, —$SO_2NH$(aliphatic), —$SO_2N$(aliphatic)$_2$, —O-aliphatic-COOH, —O-aliphatic-$NH_2$ (which may contain one or two N-aliphatic or N-acyl substituents), C1-C6 alkyl, acyl, acyloxy, C1-C6 alkoxy, e.g. methoxy, ethoxy, methylenedioxy, ethylenedioxy, etc. Heteroaryl groups are as discussed previously, including indolyl, pyridyl, pyrrolyl, etc. Particular $R^4$ moieties include the following:

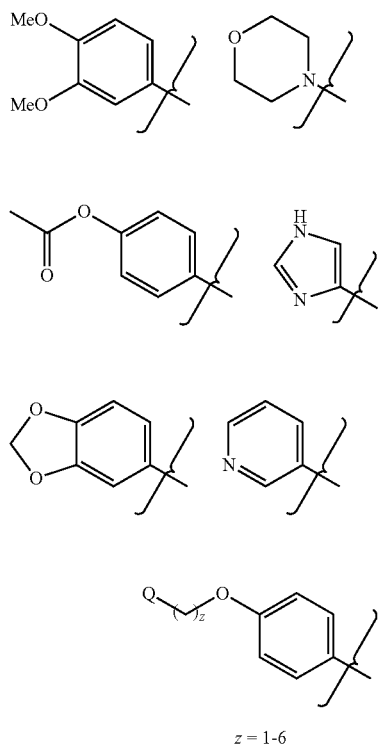

$z = 1-6$

Q = —$NH_2$, -NHalkyl, -Ndialkyl, —COOH, or —OH $R^5$ is a branched, unbranched or cyclic aliphatic moiety of 1 to 8 carbon atoms, which may be optionally substituted, including for example, —CH—, —$CHCH_2$—, —$CH_2CH$—, —$CHCH_2CH_2$—, —$CH_2CHCH_2$—, —CH($CH_3$)—$CH_2$—CH, —CH($CH_2CH_3$)—$CH_2$—CH, —$CH_2CH_2CH$—, —C($CH_3$)$CH_2$—, and the like;

$R^6$ is an aliphatic, heteroaliphatic, heterocylic, aryl or heteroaryl moiety, which may be substituted or unsubstituted.

Typical substituents for $R^6$ include branched, unbranched or cyclic, C1-C8, aliphatic or heteroaliphatic groups, including unsaturated groups such as substitute or unsubstituted alkenes, heterocycles, phenyl, etc.

$R^7$ is H or a reactive functional group permitting covalent attachment to a linker moiety. $R^7$ may be —$(CH_2)_z$—CH=$CH_2$, —$(CH_2)_z$—COOH, —$(CH_2)_z$—CHO, —$(CH_2)_z$—OH, —$(CH_2)_z$—NH2, —$(CH_2)_z$—NH-alkyl, —$(CH_2)_z$—SH, etc. In embodiments where R6 is aryl, R7 may be present in the o, m, or p position. z is an integer from 0 through 4.

As discussed above, $B^1$, $B^2$ and $R^2$ may be aliphatic, heteroaliphatic, aryl or heteroaryl. Typical groups include a branched, unbranched or cyclic, saturated or unsaturated, aliphatic moiety, preferably of 1 to about 12 carbon atoms (including for example methyl, ethyl, n-propyl, isopropyl, cyclopropyl, —$CH_2$-cyclopropyl, allyl, n-butyl, sec-butyl, isobutyl, tert-butyl, cyclobutyl, —$CH_2$-cyclobutyl, n-pentyl, sec-pentyl, isopentyl, tert-pentyl, cyclopentyl, —$CH_2$-cyclopentyl, n-hexyl, sec-hexyl, cyclohexyl, —$CH_2$-cyclohexyl and the like), which aliphatic moiety may optionally be substituted with an —OH, —C=O, —COOH, CHO, allyl, $NH_2$ (or substituted amine, amide, urea or carbamate), ether (or thio-ether, in either case, aliphatic or aromatic), aryl, or heteroaryl moiety, and may optionally contain a heteroatom in place of one or more $CH_2$ or CH units; or a substituted or unsubstituted aryl (e.g. mono-, di- and tri-alkoxyphenyl; methylenedioxyphenyl or ethylenedioxyphenyl; halophenyl; or -phenyl-C(Me)$_2$-$CH_2$—O—CO—[C3-C6] alkyl or alkylamino) or heteroaromatic moiety. In such embodiments, where YR2 is —OPhenyl and $B^1$ is H, $B^2$ is preferably not cyclopentyl. In other embodiments, Y is NH and the moiety —(C=O)—CH($B^1$)NHR$^2$ comprises among other groups, D- or L-forms of naturally occurring or synthetic alpha amino acids as well as N-alkyl, N-acyl, N-aryl and N-aroyl derivatives thereof. Particular G moieties comprising $B^1$, $B^2$ and YR$^2$ groups further include those illustrated in the tables of monomers and dimers below. In embodiments where G is —OR$^2$, it is preferred that R$^2$ be other than t-butyl, especially in embodiments where $R^4R^5$ is phenethyl.

Linker moieties (L), need not contain essential elements for binding to the immunophilin proteins, and may be selected from a very broad range of structural types. Linker moieties of particular interest include aliphatic, heteroaliphatic, aryl or heteroaryl structures, as defined above, generally having 2 to about 40 carbon atoms, not counting carbon atoms of any optional substituent groups. The linker moiety may contain one or more ether, thioether, amine, amide, urea, carbamate, sulfonamide, thiocarbamate, ester, thioester, keto, hydroxyl and/or thiol moieties or substituents. Linker moieties may be conveniently joined to monomers $M^1$ and $M^2$ or Q through functional groups such as ethers, amides, ureas, carbamates, and esters; or through alkyl-alkyl, alkyl-aryl, or aryl-aryl carbon-carbon bonds. See e.g. the above cited international patent applications for numerous examples. Furthermore, linker moieties may be optimized (e.g., by modification of chain length and/or substituents) to enhance physicochemical or pharmacokinetic properties of the multimerizing agent. Numerous linker moieties and classes of linker moieties of general applicability to any of the monomers of this invention are exemplified in the various illustrative compounds disclosed herein. Illustrative linkers are depicted in the Linker Table, below. Note that a connecting moiety such as —O—$CH_2CO$— may be drawn as a component of the linker or the monomer.

| Linker Table |
|---|
| 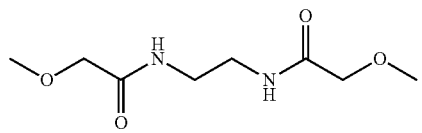 |
| 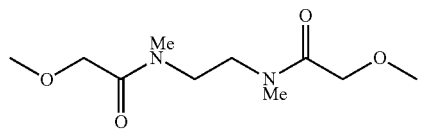 |
| 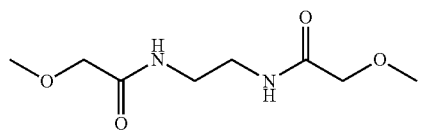 |
| 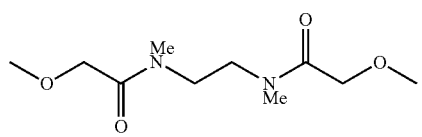 |
| 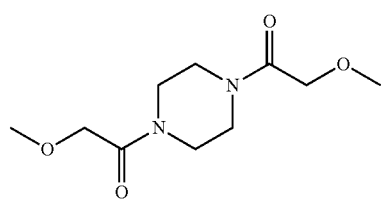 |
| 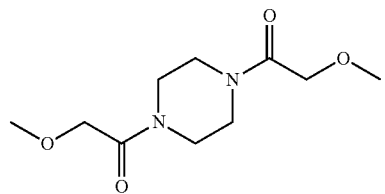 |
| 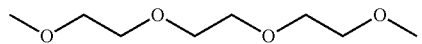 |
| 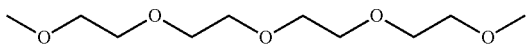 |
| 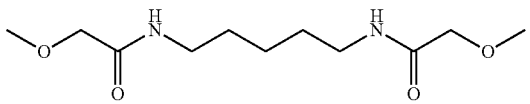 |
| 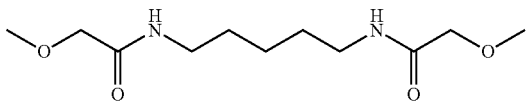 |
| 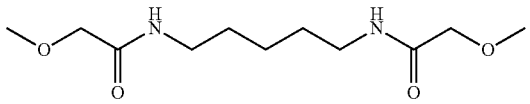 |
| 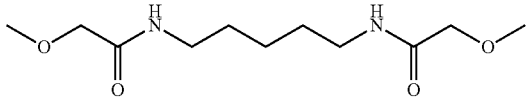 |

Linker Table
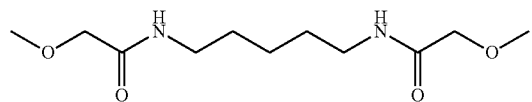
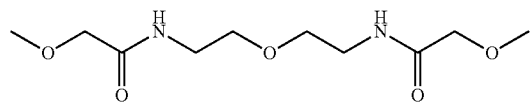
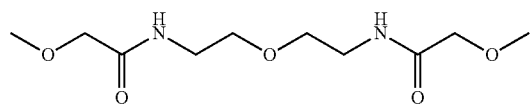
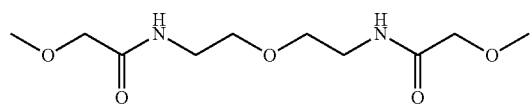
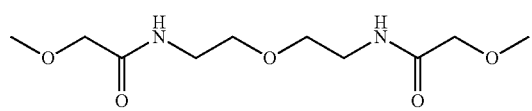
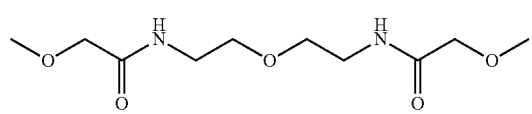
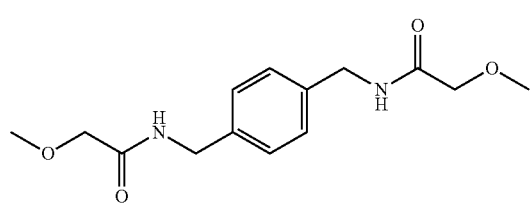
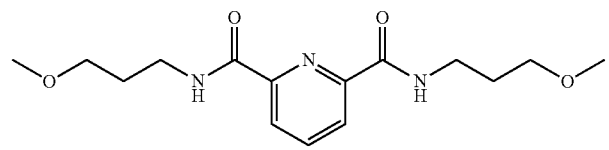
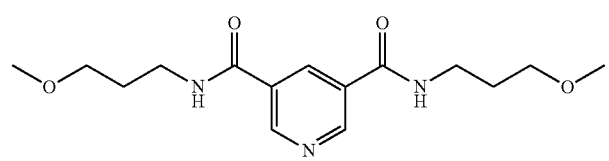
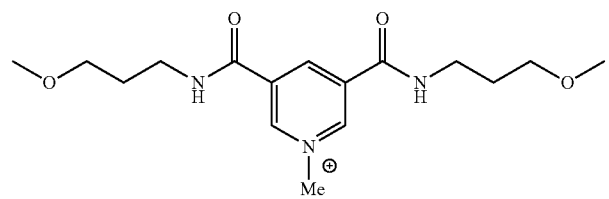

-continued
Linker Table
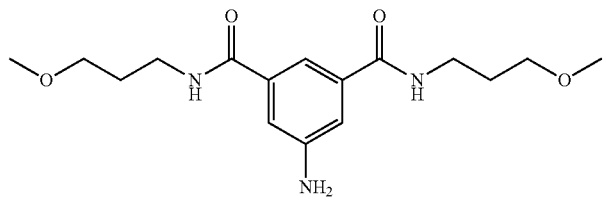
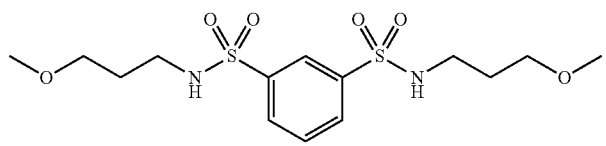
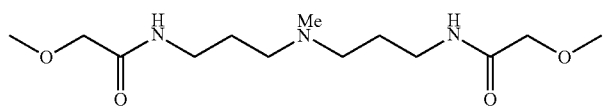
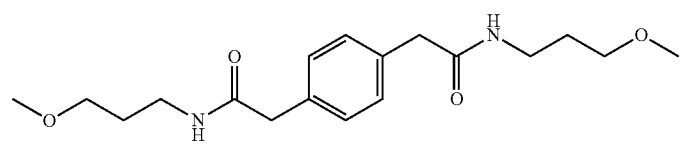
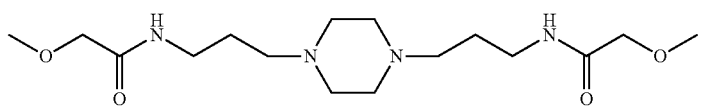
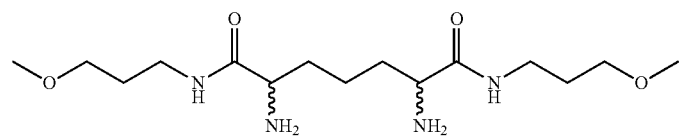
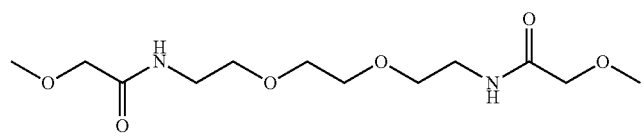
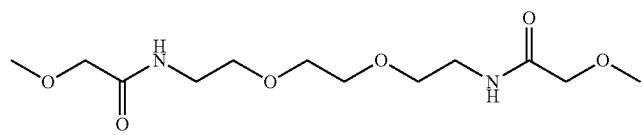
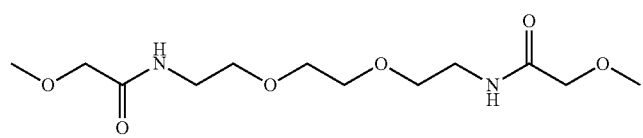
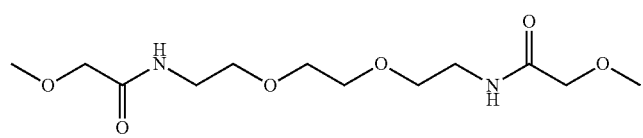
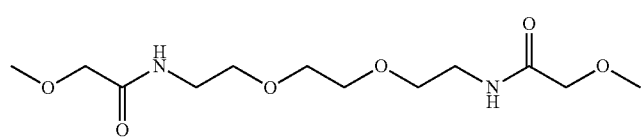

Linker Table

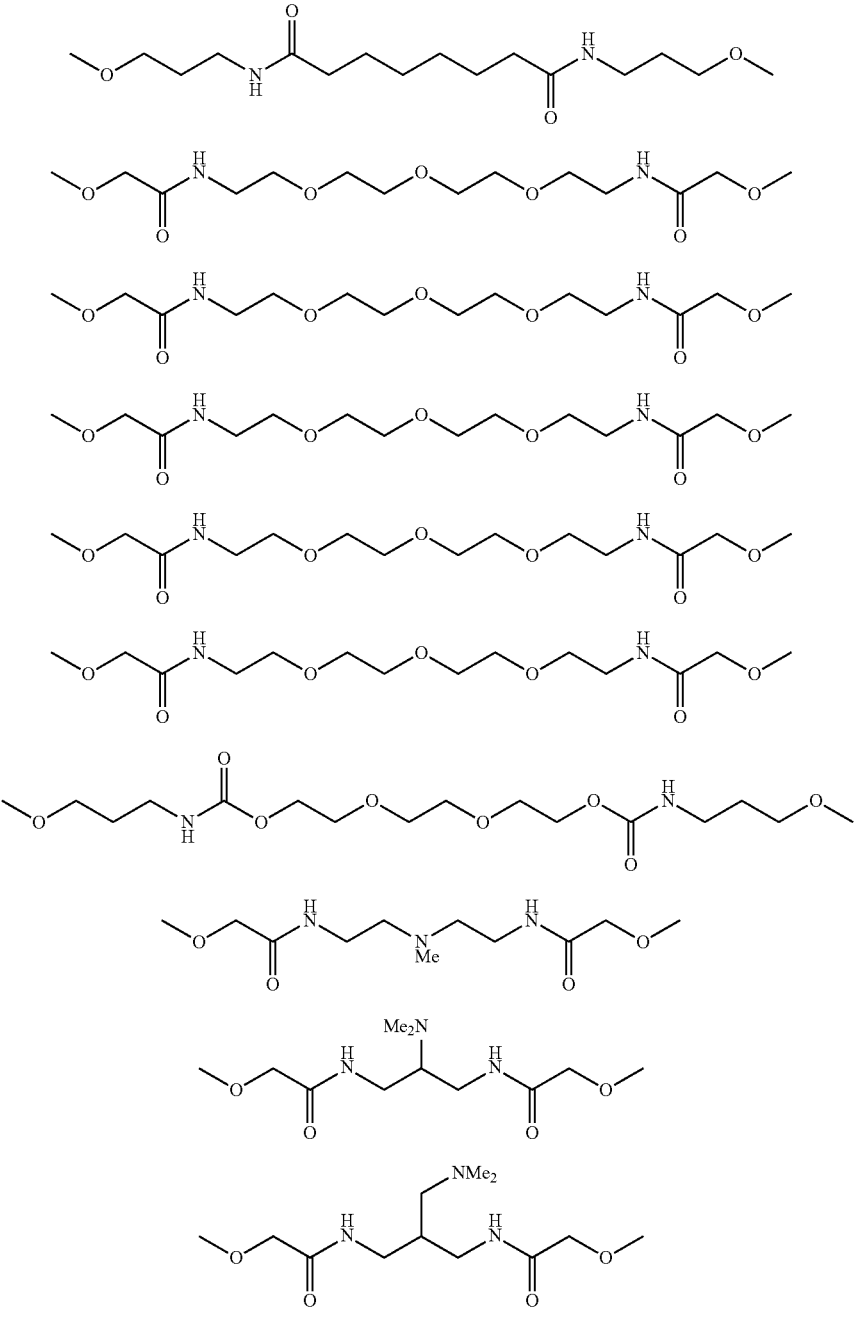

One preferred class of compounds of this invention are compounds of formula I which contain at least one moiety, M, in which n is 2.

Another preferred class of compounds of this invention are compounds of formula IV which contain two moieties, M, of formula II, which may be the same or different.

Another preferred class of compounds of this invention are compounds of formula I which contain at least one moiety, M, in which $B^1$ is H; $B^2$ is branched, unbranched or cyclic, saturated or unsaturated, aliphatic moiety, preferably of 1 to 8, more preferably 1 to 6, carbon atoms (including for example methyl, ethyl, n-propyl, isopropyl, cyclopropyl, —CH$_2$-cyclopropyl, allyl, n-butyl, sec-butyl, isobutyl, tert-butyl, cyclobutyl, —CH$_2$-cyclobutyl, n-pentyl, sec-pentyl, isopentyl, tert-pentyl, cyclopentyl, —CH$_2$-cyclopentyl, n-hexyl, sec-hexyl, cyclohexyl, —CH$_2$-cyclohexyl and the like), which aliphatic moiety may optionally be substituted, e.g. with an —OH, —C=O, —COOH, CHO, allyl, NH$_2$ (or substituted amine, amide, urea or carbamate), or ether (or thio-ether, in either case, aliphatic or aromatic), and may optionally contain a heteroatom in place of one or more CH$_2$ or CH units; and YR$^2$ is aryl, heteroaryl and may be optionally substituted (YR², for instance, includes moieties such as o-, m-, or p-alkoxyphenyl; 3,5-, 2,3-, 2,4-, 2,5-, 3,4- or 3,5-dialkoxyphenyl, or 3,4,5-trialkoxyphenyl, e.g. where the alkoxy groups are independently selected from methoxy and ethoxy (one or more of which may bear a hydroxy or amino moiety).

Another preferred class of compounds of this invention are compounds of formula I which contain at least one moiety, M, in which $B^1$, $B^2$, and $YR^2$ are the same or different lower aliphatic moieties.

Another preferred class of compounds of this invention are compounds of formula I which contain at least one moiety, M, in which G is a substituted amine in which $B^1$ is H and $R^2$ is lower aliphatic.

Another preferred class of compounds of this invention are compounds of formula I which contain at least one moiety, M, in which G is an alicyclic or heterocyclic group bearing optional substituents.

Another preferred class of compounds of this invention are compounds of formula I which contain at least one moiety, M, in which X is oxygen and $R^1$ comprises $R^4R^5R^6R^7$ where $R^4$ is aliphatic, alicyclic, aryl, heteroaryl, or heterocyclic, optionally substituted; $R^5$ is a branched or unbranched lower aliphatic group; $R^6$ is aliphatic, alicyclic, heteroaliphatic, heterocyclic, aryl or heteroaryl, optionally substituted.

Another preferred class of compounds of this invention are compounds of formula I which contain at least one moiety, M, in which $R^1$ comprises $R^4R^5R^6R^7$ as described in the immediately preceding paragraph and $YR^2$ comprises a substituted or unsubstituted aryl or heteroaryl, including phenyl; o-, m- or p-substituted phenyl where the substituent is halo such as chloro, lower alkyl, or alkoxy, such as methoxy or ethoxy; disubstituted phenyl, e.g. dialkoxyphenyl such as 2,4-, 3,4- or 3,5-dimethoxy or diethoxy phenyl or such as methylenedioxyphenyl, or 3-methoxy-5-ethoxyphenyl; or trisubstituted phenyl, such as trialkoxy (e.g., 3,4,5-trimethoxy or ethoxyphenyl), 3,5-dimethoxy-4-chloro-phenyl, etc.).

Particular monomers and dimers that were synthesized and which serve to illustrate the invention are shown in the Synthetic Monomers Table and Synthetic Multimerizers Table, below. The Synthetic Monomers Table sets forth a wide range of compounds synthesized and presents data from our Competitive Binding FP Assay for most of the disclosed monomers with respect to both wild-type human FKBP12 and a series of mutant FKBPs. The data show that the monomers of formula II bind to the modified FKBP proteins with IC50's in many cases in the hundreds, tens, and in some cases single digits (nM). A considerable number of the compounds bind to a modified FKBP with an IC50 value 10-fold, 100-fold, or 1000-fold or more better than for binding to wild type human FKBP12. Note that the first several compounds are monomers of formula III, included for the sake of comparison.

The Synthetic Multimerizers Table sets forth a sample of multimerizers with data from the Competitive Binding FP Assay, Transcription Assay and Apoptosis Assay. Again, profound discrimination for mutant FKBP domains over wild-type FKBP domains is shown.

| | SYNTHETIC MONOMERS ("R" Groups are identified below) | | | | | | |
|---|---|---|---|---|---|---|---|
| | | wild-type IC50 (nM) | F36V IC50 (nM) | F36L IC50 (nM) | F36I IC50 (nM) | F36M IC50 (nM) | F36A IC50 (nM) | F36S IC50 (nM) |
| FK506 | | 2.5 (Kd = 0.23) | 12 (Kd = 2.3) | 20 | 19 | 15 | 62 | 193 |
| AP1540 | [structure with R₂] | 97 | 50 | 63 | 100 | 73 | 327 | |
| AP1497 | [structure with R₁] | 86 | 44 | 47 | 43 | 47 | 174 | 1820 |
| AP3351 | [structure with R₇] | 83 | 76 | 65 | 66 | 32 | 171 | |
| AP1965 | [structure with R₁, trimethoxyphenyl] | 326 | 107 | 143 | 105 | 131 | 1374 | |

-continued
SYNTHETIC MONOMERS
("R" Groups are identified below)
| | | wild-type IC50 (nM) | F36V IC50 (nM) | F36L IC50 (nM) | F36I IC50 (nM) | F36M IC50 (nM) | F36A IC50 (nM) | F36S IC50 (nM) |
|---|---|---|---|---|---|---|---|---|
| AP1767 | 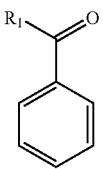 | 1420 | 390 | 375 | 3916 | 623 | 13600 | |
| AP1780 | 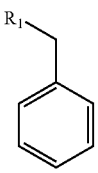 | 21620 | 1530 | 3560 | 2059 | 2600 | 8330 | |
| AP1784 | 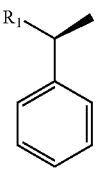 | 16000 | 94 | 92 | 117 | 414 | 171 | |
| AP1782 | 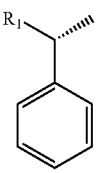 | >100000 | 590 | 1400 | 1049 | 927 | 1434 | |
| AP1643 | 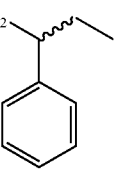 | >10000 | 37 | 124 | 146 | 115 | 150 | 220 |
| AP1768 | 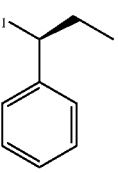 | 57000 | 40 | 51 | 93 | 123 | 66 | |
| AP1769 | 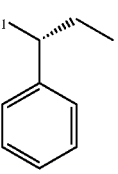 | 220000 | 133 | 238 | 346 | 193 | 460 | |
| AP1781 | 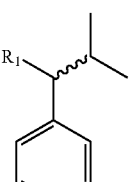 | 38600 | 26 | 33 | 36 | 55 | 109 | |

-continued
| | | SYNTHETIC MONOMERS ("R" Groups are identified below) | | | | | | |
|---|---|---|---|---|---|---|---|---|
| | | wild-type IC50 (nM) | F36V IC50 (nM) | F36L IC50 (nM) | F36I IC50 (nM) | F36M IC50 (nM) | F36A IC50 (nM) | F36S IC50 (nM) |
| AP1597 | 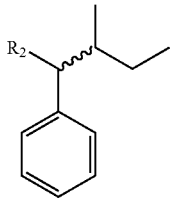 | >10000 | 28 | 58 | 35 | 32 | 55 | 133 |
| AP1748 | 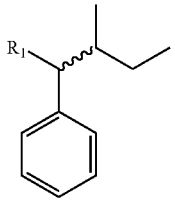 | 9580 | 13 | 24 | 8 | 16 | 21 | 47 |
| AP1778 | 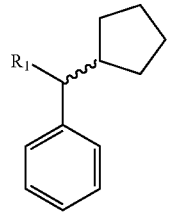 | 16000 | 22 | 32 | 41 | 31 | 75 | |
| AP1779 | 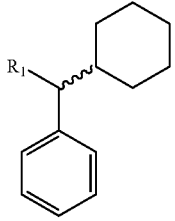 | 3000 | 13 | 16 | 137 | 17 | 23 | |
| AP14245 | 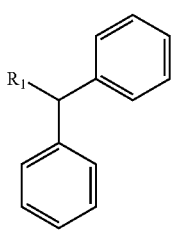 | 73% @ 100000 | 273 | 684 | 562 | 173 | 127 | |
| AP1642 | 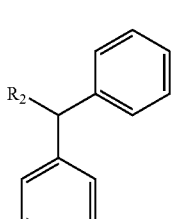 | >>10000 | 160 | 381 | 349 | 159 | 144 | |
| AP1831 | 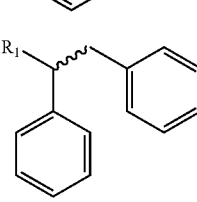 | >10000 | 153 | 217 | 124 | 169 | 447 | |

-continued

SYNTHETIC MONOMERS
("R" Groups are identified below)

| | | wild-type IC50 (nM) | F36V IC50 (nM) | F36L IC50 (nM) | F36I IC50 (nM) | F36M IC50 (nM) | F36A IC50 (nM) | F36S IC50 (nM) |
|---|---|---|---|---|---|---|---|---|
| AP1644 | R₂–CH(cyclohexyl)₂ | >>10000 | 240 | 168 | 366 | 84 | 96 | |
| AP1596 | R₂–C(cyclopropyl)(phenyl) | >10000 | 290 | 359 | 643 | 2080 | 1142 | |
| AP1645 | R₂–CH(CH₂OH)(phenyl) | >10000 | 750 | 909 | 1000 | 1850 | 1637 | |
| AP1552 | R₂–C(OMe)(C(CH₃)₂Et) | >10000 | 810 | 643 | 1738 | 790 | 2352 | 4380 |
| AP1595 | R₂–CH(OMe)(phenyl) | 1330 | 926 | 1550 | 1541 | 14130 | >10000 | 8780 |
| AP1553 | R₂–C(OEt)(C(CH₃)₂Et) | >10000 | 1000 | 581 | 996 | 1008 | 1165 | |
| AP1554 | R₂–C(OPr)(C(CH₃)₂Et) | >10000 | 302 | 244 | 672 | 306 | 598 | |
| AP1574 | R₂–C(OBu)(C(CH₃)₂Et) | >10000 | 2100 | 703 | 1553 | 736 | 1037 | |

-continued

| | SYNTHETIC MONOMERS ("R" Groups are identified below) | | | | | | | |
|---|---|---|---|---|---|---|---|---|
| | | wild-type IC50 (nM) | F36V IC50 (nM) | F36L IC50 (nM) | F36I IC50 (nM) | F36M IC50 (nM) | F36A IC50 (nM) | F36S IC50 (nM) |
| AP1575 | R₂-O-CH₂-Ph structure | >10000 | 1726 | 654 | 5994 | 630 | 776 | |
| AP1598 | R₂-O-CH₂-cyclopropyl structure | >10000 | 440 | 267 | 975 | 321 | 648 | |
| AP1785 | R₁-(3,4,5-trimethoxyphenyl)ethyl | 4760 | 7 | 7.3 | 9.9 | 29 | 34 | |
| AP1867 | R₁-(3,4,5-trimethoxyphenyl)ethyl | 2930 | 1.8 | 6.2 | 5.1 | 10 | 18 | |
| AP1904 | R₁-(3,4,5-trimethoxyphenyl)ethyl | >100000 | 187 | 212 | 163 | 424 | 431 | |
| AP14246 | R₆-(3,4,5-trimethoxyphenyl)ethyl | 75% @ 100000 | 16.5 | 68 | 32 | 52 | 77 | |
| AP14247 | R₆-(3,4,5-trimethoxyphenyl)ethyl | 75% @ 100000 | 103 | 324 | 334 | 256 | 594 | |

SYNTHETIC MONOMERS
("R" Groups are identified below)

| | | wild-type IC50 (nM) | F36V IC50 (nM) | F36L IC50 (nM) | F36I IC50 (nM) | F36M IC50 (nM) | F36A IC50 (nM) | F36S IC50 (nM) |
|---|---|---|---|---|---|---|---|---|
| AP14252 | $R_9$-substituted 3,4,5-trimethoxyphenyl ethyl | | | 32 | 6.7 | 54 | 63 | |
| AP14284 | $R_{11}$-substituted 3,4,5-trimethoxyphenyl ethyl | | | | | | | |
| AP14268 | $R_1$-substituted 3,4,5-trimethoxyphenyl propyl | 5065 | 3.8 | 7.2 | 5.6 | 3.3 | 9.2 | |
| AP14269 | $R_1$-substituted 3,4,5-trimethoxyphenyl propyl | 90% @ 10000 | 43 | 146 | 76 | 73 | 84 | |
| AP14270 | $R_1$-substituted 3,4,5-trimethoxyphenyl allyl | 3670 | 1.53 | 4.7 | 3 | 3.7 | 8.1 | |
| AP14271 | $R_1$-substituted 3,4,5-trimethoxyphenyl allyl | 90% @ 10000 | 19 | 57 | 24 | 42 | 57 | |

-continued

SYNTHETIC MONOMERS
("R" Groups are identified below)

| | | wild-type IC50 (nM) | F36V IC50 (nM) | F36L IC50 (nM) | F36I IC50 (nM) | F36M IC50 (nM) | F36A IC50 (nM) | F36S IC50 (nM) |
|---|---|---|---|---|---|---|---|---|
| AP14885 | (structure: R₁ with cyclopropylmethyl on 3,4,5-trimethoxyphenyl) | 8440 | 4.4 | 14 | | | | |
| AP14886 | (structure: R₁ with cyclopropylmethyl on 3,4,5-trimethoxyphenyl, opposite stereo) | 90% @ 10000 | 126 | 400 | | | | |
| AP1921 | (structure: R₁ with isobutyl on 3,4,5-trimethoxyphenyl) | 4894 | 5.8 | 6.1 | 10 | 10 | 16 | |
| AP1922 | (structure: R₁ with isobutyl on 3,4,5-trimethoxyphenyl, opposite stereo) | >100000 | 65 | 74 | 106 | 46 | 119 | |
| AP1786 | (structure: R₁ with ethyl on 4-methoxyphenyl) | 150000 | 42 | 69 | 91 | 154 | 130 | |
| AP1830 | (structure: R₁ with ethyl on 3-methoxyphenyl) | 115106 | 37 | 70 | 44 | 119 | 105 | |

| | SYNTHETIC MONOMERS ("R" Groups are identified below) | wild-type IC50 (nM) | F36V IC50 (nM) | F36L IC50 (nM) | F36I IC50 (nM) | F36M IC50 (nM) | F36A IC50 (nM) | F36S IC50 (nM) |
|---|---|---|---|---|---|---|---|---|
| AP1828 | R₁ attached to CH(Et)-(2-MeO-phenyl) | 45750 | 93 | 211 | 153 | 425 | 586 | |
| AP1832 | R₁ attached to CH(Et)-(2-thienyl) | >10000 | 62 | 121 | 135 | 182 | 156 | |
| AP1888 | R₁ attached to CH(n-Pr)₂ (heptan-4-yl) | >100000 | 77 | 269 | 307 | 362 | 207 | |
| AP1833 | R₁ attached to CH(Et)₂ (pentan-3-yl) | >100000 | 102 | 287 | 289 | 770 | 240 | |
| AP1865 | R₁-iPr | 12056 | 713 | 1763 | 1143 | 2946 | 2700 | |
| AP1962 | R₁-tBu | 13467 | 390 | 426 | 947 | 2282 | 2700 | |
| AP1919 | R₁-NH-CH(Et)₂ | 13966 | 64 | 45 | 138 | 66 | 107 | |
| AP3353 | R₂-NH-CH(Et)₂ | 90% @ 100000 | 1755 | 1518 | 3409 | 1240 | 3530 | |
| AP20188 | R₁-NH-CH(cyclopropyl)₂ | | | | | | | |
| AP1837 | R₁-(2-methylcyclohexyl) | >10000 | 79 | 53 | 85 | 227 | 141 | |
| AP1892 | R₁-(3-methyl-2-thienyl) | >100000 | 2989 | 1630 | 5470 | 5930 | 5720 | |

-continued

| | SYNTHETIC MONOMERS ("R" Groups are identified below) | | | | | | |
|---|---|---|---|---|---|---|---|
| | | wild-type IC50 (nM) | F36V IC50 (nM) | F36L IC50 (nM) | F36I IC50 (nM) | F36M IC50 (nM) | F36A IC50 (nM) | F36S IC50 (nM) |
| AP1839 | R₁ attached to benzo[1,3]dioxole | 13490 | 9 | 57 | 26 | 19 | 32 | |
| AP1841 | R₂ attached to phenyl | >100000 | 4285 | 7470 | 7554 | 21090 | 4840 | |
| AP1811 | R₁ attached to 4-chlorophenyl | 49900 | 226 | 441 | 294 | 181 | 332 | |
| AP1814 | R₁ attached to 4-chlorophenyl | 17590 | 34 | 56 | 54 | 62 | 81 | |
| AP1864 | R₁ attached to morpholine | >100000 | 2724 | 3790 | 4490 | 10000 | 8800 | |
| AP1972 | R₅ attached to 3,4,5-trimethoxyphenyl | 61800 | 265 | 359 | 351 | 697 | 665 | |
| AP1973 | R₆ attached to 3,4,5-trimethoxyphenyl | 80% @ 100000 | 100 | 141 | 139 | 364 | 253 | |

SYNTHETIC MONOMERS
("R" Groups are identified below)
| | | wild-type IC50 (nM) | F36V IC50 (nM) | F36L IC50 (nM) | F36I IC50 (nM) | F36M IC50 (nM) | F36A IC50 (nM) | F36S IC50 (nM) |
|---|---|---|---|---|---|---|---|---|
| AP1974 | R₁-NH-CH(CH₃)-Ph | 73529 | 450 | 670 | 1165 | 176 | 94 | |
| AP1975 | R₁-NH-CH(CH₃)-Ph | 4200 | 381 | 126 | 368 | 218 | 406 | |
| AP1977 | R₁-NH-cyclohexyl | 2652 | 169 | 121 | 150 | 166 | 486 | |
For the purposes of this table:
R₁ =
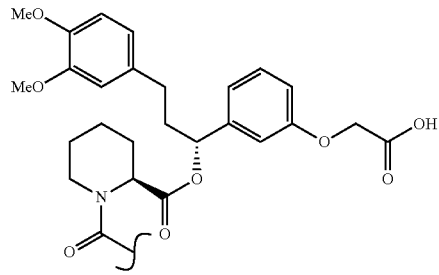 [SMILES: COc1ccc(CC[C@@H](OC(=O)[C@@H]2CCCCN2C(C)=O)c2cccc(OCC(=O)O)c2)cc1OC]
R₂ =
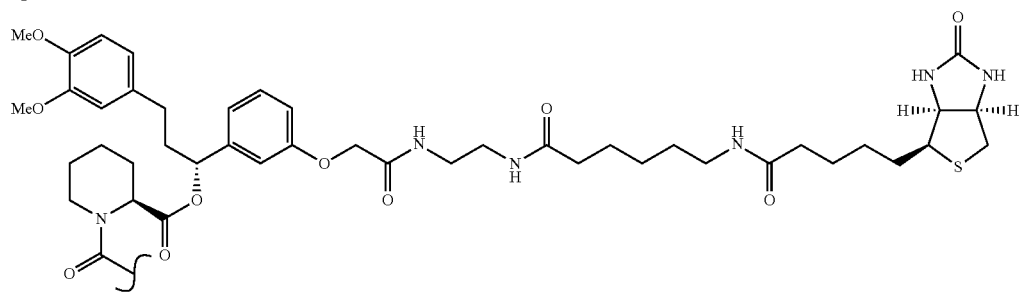
R₃ =
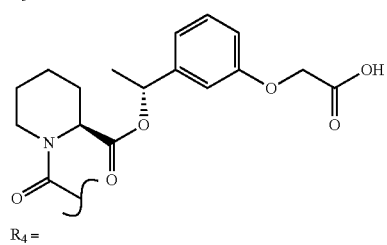
R₄ =

SYNTHETIC MONOMERS
("R" Groups are identified below)
| | wild-type IC50 (nM) | F36V IC50 (nM) | F36L IC50 (nM) | F36I IC50 (nM) | F36M IC50 (nM) | F36A IC50 (nM) | F36S IC50 (nM) |
|---|---|---|---|---|---|---|---|
R₅ =
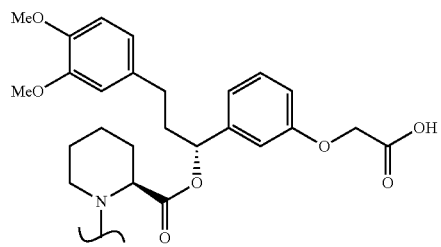 [SMILES: COc1ccc(CC[C@@H](OC(=O)[C@@H]2CCCCN2C)c2cccc(OCC(=O)O)c2)cc1OC]
R₆ =
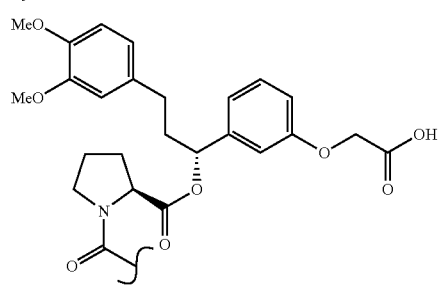
R₇ =
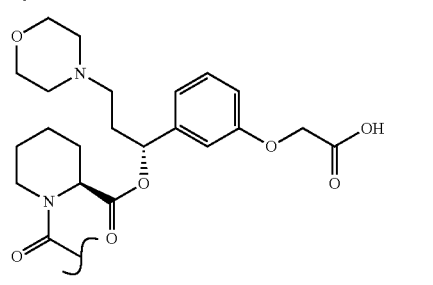
R₈ =
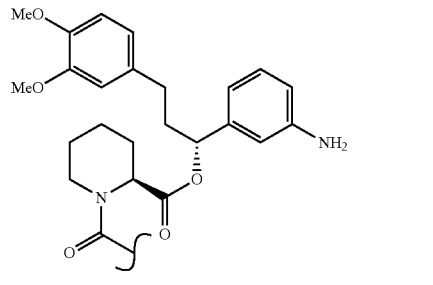 [SMILES: COc1ccc(CC[C@@H](OC(=O)[C@@H]2CCCCN2C(C)=O)c2cccc(N)c2)cc1OC]
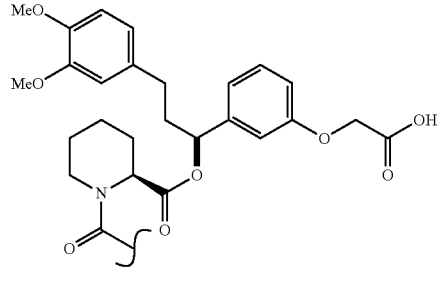 [SMILES: COc1ccc(CC[C@H](OC(=O)[C@@H]2CCCCN2C(C)=O)c2cccc(OCC(=O)O)c2)cc1OC]

-continued
SYNTHETIC MONOMERS
("R" Groups are identified below)
| | wild-type IC50 (nM) | F36V IC50 (nM) | F36L IC50 (nM) | F36I IC50 (nM) | F36M IC50 (nM) | F36A IC50 (nM) | F36S IC50 (nM) |
|---|---|---|---|---|---|---|---|
R₉ =
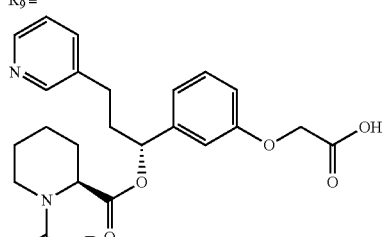
R₁₁ =
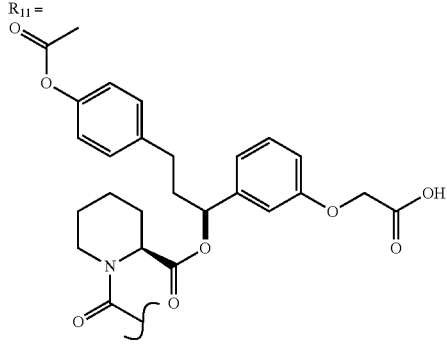
All data normalized to value of FK506 run in the same experiment

SYNTHETIC MULTIMERIZERS TABLE

| dimerizer (monomer) | monomer subunit | linker | FKBP$_{wt}$ binding affinity IC$_{50}$ (nM) | FKBP$_{F36V}$ binding affinity IC$_{50}$ (nM) | FKBP$_{F36L}$ binding affinity IC$_{50}$ (nM) | activation of transcription (wt; stable) EC50, nM[b] (% AP1510)[c] | activation of transcription (F36V; stable) EC50, nM[d] (% AP1510)[e] | Fas killing (wt, stable) EC50 (nM) | Fas killing (36V, stable) EC50 (nM) |
|---|---|---|---|---|---|---|---|---|---|
| AP1749 (AP1748) | 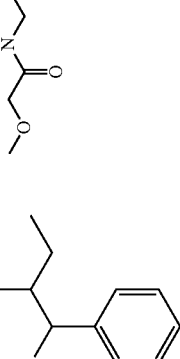 | 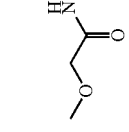 (AP1428) | >100000 (15529) | 1034[a] (6.9) | 4778[a] (ND) | 0% @ 1000 | 150 (90%)<br>60 (90%)<br>200 (90%) | 0% @ 1000 | >1000 |
| AP1754 (AP1748) | 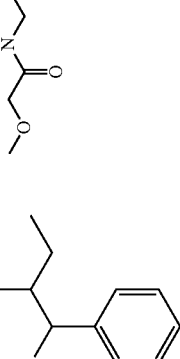 | 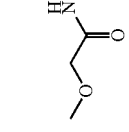 (AP1510) | >100000 (15529) | 512[a] (6.9) | 20930[a] (ND) | 0% @ 1000 | 50 (50%)<br>60 (50%)<br>40 (75%)<br>33 (80%)<br>40 (ND)<br>50 (40%) | 0% @ 1000 | >1000 |
| AP1829 (AP1785) | 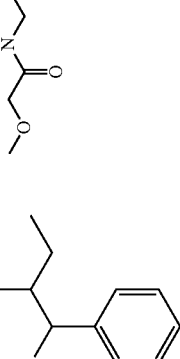 | 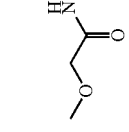 (AP1510) | >10000 (4760) | 3.1 (4.8) | 1.5 (ND) | 0.3% @ 1000 | 8 (9%)<br>5 (7%)<br>8 (25%)<br>6 (35%)<br>3 (ND)<br>6 (3%) | 100 - >1000 | 0.5 - <10 |
| AP1903 (AP1867) | 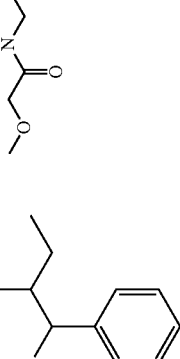 | 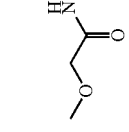 (AP1510) | >10000 (1960) | 3.2 (1.8) | 1.3 (6.2) | 0.5% @ 1000 | 6 (3%) | 40 - 50 | <1 |

SYNTHETIC MULTIMERIZERS TABLE-continued

| dimerizer (monomer) | monomer subunit | linker | FKBP$_{wt}$ binding affinity IC$_{50}$ (nM) | FKBP$_{F36V}$ binding affinity IC$_{50}$ (nM) | FKBP$_{F36L}$ binding affinity IC$_{50}$ (nM) | activation of transcription (wt; stable) EC50, nM[b] (% AP1510)[c] | activation of transcription (F36V; stable) EC50, nM[d] (% AP1510)[c] | Fas killing (wt, stable) EC50 (nM) | Fas killing (36V, stable) EC50 (nM) |
|---|---|---|---|---|---|---|---|---|---|
| AP3344 (AP1921) | 3,4,5-triMeO-phenyl with iPr at R$_1$ | (AP1510) | 95% @ 10000 (4894) | 7 (5.8) | 9.6 (6.1) | 3% @ 1000 | 2 (5%)[e] | 200 - 300 | 1 |
| AP14280 (AP14270) | 3,4,5-triMeO-phenyl with allyl at R$_1$ | (AP1510) | 90% @ 10000 (3670) | 3.2 (1.53) | 14 | • | 2 (25%) | >10 | <1 |
| AP1889 (AP1768) | phenyl with Et at R$_1$ | (AP1510) | >10000 (>100000) | 10000[a] (22.2) | 70% @ 10000 (ND) | 0% @ 1000<br>1% @ 1000<br>0% @ 1000 | 2 (ND)<br>6 (60%)<br>15 (150%)[e]<br>10 (175%)[e]<br>9 (130%) | 0% @ 1000 | 1 |
| AP1885 (AP1839) | benzo[1,3]dioxole with Et at R$_1$ | (AP1510) | >10000 (>16868) | 59.4 (5.4) | 1091 (ND) | 0% @ 1000 | 5 (85%)<br>2 (ND)<br>10 (80%) | 0% @ 1000 | 1 - 20 |

SYNTHETIC MULTIMERIZERS TABLE-continued

| dimerizer (monomer) | monomer subunit | linker | FKBP$_{wt}$ binding affinity IC$_{50}$ (nM) | FKBP$_{F36V}$ binding affinity IC$_{50}$ (nM) | FKBP$_{F36L}$ binding affinity IC$_{50}$ (nM) | activation of transcription (wt; stable) EC50, nM[b] (% AP1510)[c] | activation of transcription (F36V; stable) EC50, nM[d] (% AP1510)[c] | Fas killing (wt, stable) EC50 (nM) | Fas killing (36V, stable) EC50 (nM) |
|---|---|---|---|---|---|---|---|---|---|
| AP1891 (AP1833) | R₁ (sec-butyl) | (AP1510) | >10000 (>100000) | 174 (76) | 272 (ND) | 0% @ 1000 | 25 (ND) 100 (65%) | 0% @ 1000 | 10 · 20 |
| AP1966 (AP1919) | R₁-NH (aminopentyl) | (AP1510) | 88% @ 100000 (13986) | 58 (84) | 64 (45) | 600 | 10 (200)[e] | 100 | 1 · <2 |
| AP3357 (AP3353) | R₂-NH | (AP1510) | 86% @ 10000 (90% @ 100000) | 252 (1755) | 254 (1518) | 0% @ 1000 | 500 (3)[e] | | |
| | | (AP1510) | >10000 (1960) | 3.2 (1.8) | 13 (6.2) | 0.5% @ 1000 60 (4%) | 6 (3%) 3 (7%) | 40 · 50 | <1 | substituted phenyl/lower aliphatic SERIES:

| dimerizer (monomer) | monomer subunit | linker | FKBP$_{wt}$ | FKBP$_{F36V}$ | FKBP$_{F36L}$ | activation (wt) | activation (F36V) | Fas killing (wt) | Fas killing (36V) |
|---|---|---|---|---|---|---|---|---|---|
| AP1903 (AP1867) | R₁-(3,4,5-trimethoxyphenyl) | | | | | | | | |
| AP14278 | R₁-(3,4,5-trimethoxyphenyl) | (bis-methoxyethyl ether linker) | >10000 | 3.2 | 8.7 | · | 20 (35%) | >10 | 2 |

SYNTHETIC MULTIMERIZERS TABLE-continued

| dimerizer (monomer) | monomer subunit | linker | FKBP$_{wt}$ binding affinity IC$_{50}$ (nM) | FKBP$_{F36V}$ binding affinity IC$_{50}$ (nM) | FKBP$_{F36L}$ binding affinity IC$_{50}$ (nM) | activation of transcription (wt; stable) EC50, nM$^b$ (% AP1510)$^c$ | activation of transcription (F36V; stable) EC50, nM$^d$ (% AP1510)$^e$ | Fas killing (wt, stable) EC50 (nM) | Fas killing (36V, stable) EC50 (nM) |
|---|---|---|---|---|---|---|---|---|---|
| AP14279 | | | 90% @ 10000 | 4.3 | 11 | • | 8 (15%) | >10 | <1 |
| AP17364 | | | | | | | | | <1 |
| AP17401 | | | | | | | | | 4 |
| AP17402 | | | 80% @ 10000 | 3.9 | 5.6 | • | 8 (5%) | • | <1 |

SYNTHETIC MULTIMERIZERS TABLE-continued

| dimerizer (monomer) | monomer subunit | linker | FKBP$_{wt}$ binding affinity IC$_{50}$ (nM) | FKBP$_{F36V}$ binding affinity IC$_{50}$ (nM) | FKBP$_{F36L}$ binding affinity IC$_{50}$ (nM) | activation of transcription (wt; stable) EC50, nM[b] (% AP1510)[c] | activation of transcription (F36V; stable) EC50, nM[d] (% AP1510)[e] | Fas killing (wt, stable) EC50 (nM) | Fas killing (36V, stable) EC50 (nM) |
|---|---|---|---|---|---|---|---|---|---|
| AP17417 | | | | | | | | | |
| AP17418 | | | | | | | | | |
| AP17419 | | | | | | | | | . |
| AP20187 | | | | | | | | | <1 |

SYNTHETIC MULTIMERIZERS TABLE-continued

| dimerizer (monomer) | monomer subunit | linker | FKBP$_{wt}$ binding affinity IC$_{50}$ (nM) | FKBP$_{F36V}$ binding affinity IC$_{50}$ (nM) | FKBP$_{F36L}$ binding affinity IC$_{50}$ (nM) | activation of transcription (wt; stable) EC50, nM[b] (% AP1510)[c] | activation of transcription (F36V; stable) EC50, nM[d] (% AP1510)[e] | Fas killing (wt, stable) EC50 (nM) | Fas killing (36V, stable) EC50 (nM) |
|---|---|---|---|---|---|---|---|---|---|
| AP14290 (AP14252) | 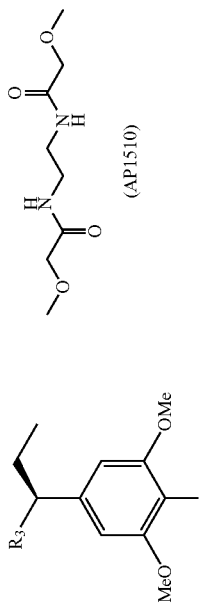 R$_3$ |  (AP1510) | | | | | | >10 | <1 |
| AP14291 (AP14246) | 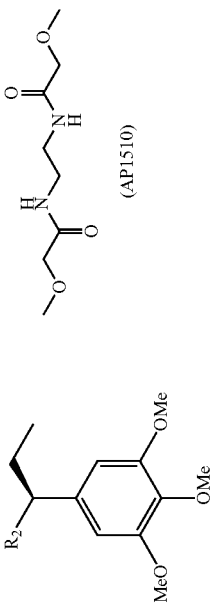 R$_2$ | 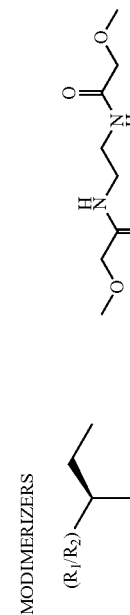 (AP1510) | (77% @ 100000) | (16.5) | | | | >10 | 10 |
| HETERO-HOMODIMERIZERS | | | | | | | | | |
| AP14272 (AP1867/ AP14246) | 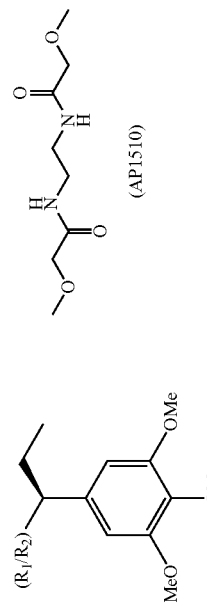 (R$_1$/R$_2$) | (AP1510) | (1960)/77% @ 100000 | (1.8/16.5) | | | | 200 · 1000 | <1 |
| AP14283 (AP1867/ AP14252) | 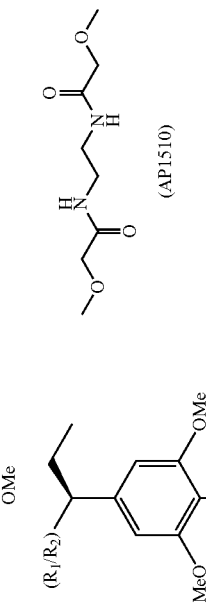 (R$_1$/R$_2$) | (AP1510) | (1960/) | (1.8/) | | | | >10 | <1 |

SYNTHETIC MULTIMERIZERS TABLE-continued

| dimerizer (monomer) | monomer subunit | linker | FKBP$_{wt}$ binding affinity IC$_{50}$ (nM) | FKBP$_{F36V}$ binding affinity IC$_{50}$ (nM) | FKBP$_{F36L}$ binding affinity IC$_{50}$ (nM) | activation of transcription (wt; stable) EC50, nM$^b$ (% AP1510)$^c$ | activation of transcription (F36V; stable) EC50, nM$^d$ (% AP1510)$^c$ | Fas killing (wt, stable) EC50 (nM) | Fas killing (36V, stable) EC50 (nM) |
|---|---|---|---|---|---|---|---|---|---|

$R_1 =$ [structure with MeO, MeO, phenyl-OCH$_2$COOH, piperidine carbonyl]

$R_2 =$ [structure with morpholine, phenyl-OCH$_2$COOH, piperidine carbonyl]

$R_3 =$ [structure with pyridine, phenyl-OCH$_2$COOH, piperidine carbonyl]

(carboxylate of monomer is also shown as part of linker in the table)
Notes:
Binding data: each value represents mean of duplicate experiments. Data are normalized to FK506 = 2.5 nM; "substituted phenyl/lower aliphatic series" data normalized to AP1903 values for each protein
Transcription data: each value represents individual experiment;
Fas signalling data: mean values shown Synthesis Compounds of this invention may be prepared by one of ordinary skill in this art relying upon methods and materials known in the art. For instance, methods and materials may be adapted from known methods for the synthesis of N-oxalyl-pipecolyl, N-oxalyl-prolyl and related monomers. See e.g. Holt, et al., *J. Amer. Chem. Soc.,* 1993, 115, 9925-9938; Holt, et al., *Biomed. Chem. Lett.,* 1993, 4, 315-320; Luengo, et al., *Biomed. Chem. Lett.,* 1993, 4, 321-324; Yamashita, et al., *Biomed. Chem. Lett.,* 1993, 4, 325-328; Spencer et al, above; PCT/US94/01617; and PCT/US94/08008. See also EP 0 455 427 A1; EP 0 465 426 A1; U.S. Pat. No. 5,023,263 and WO 92/00278. Additional guidance and examples are provided herein by way of illustration and further guidance to the practitioner. It should be understood that the chemist of ordinary skill in this art would be readily able to make modifications to the foregoing, e.g. to add appropriate protecting groups to sensitive moieties during synthesis, followed by removal of the protecting groups when no longer needed or desired, and would be readily capable of determining other synthetic approaches.

By way of example, monomers may be assembled and dimerized via a number of synthetic schemes and in various orders as illustrated in the following reaction schemes.

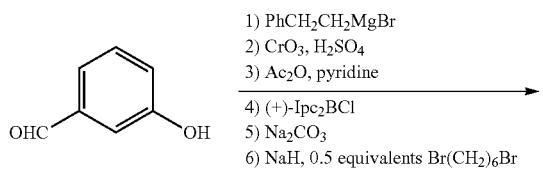

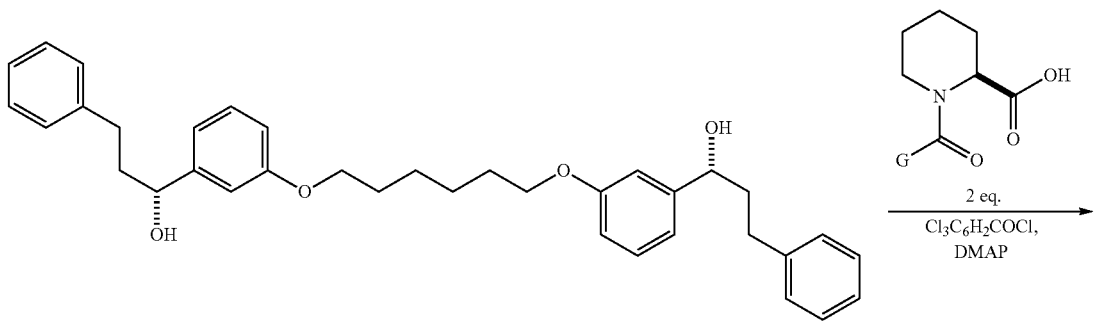

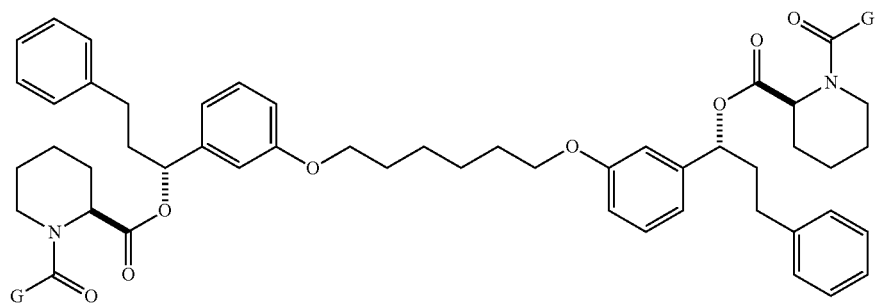

see: Holt, et al. *J. Amer. Chem., Soc,* 1993, 115, 9925-9938.

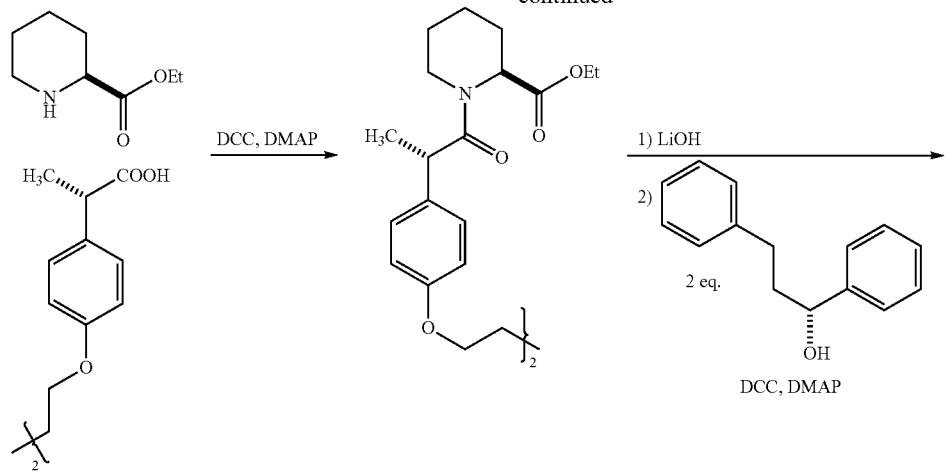
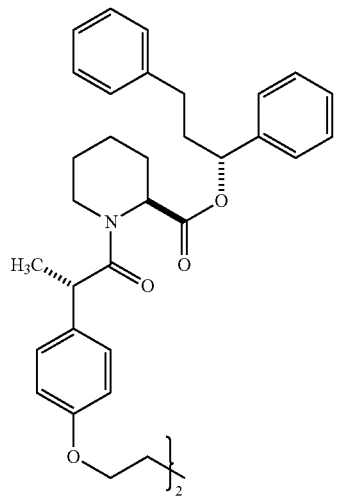
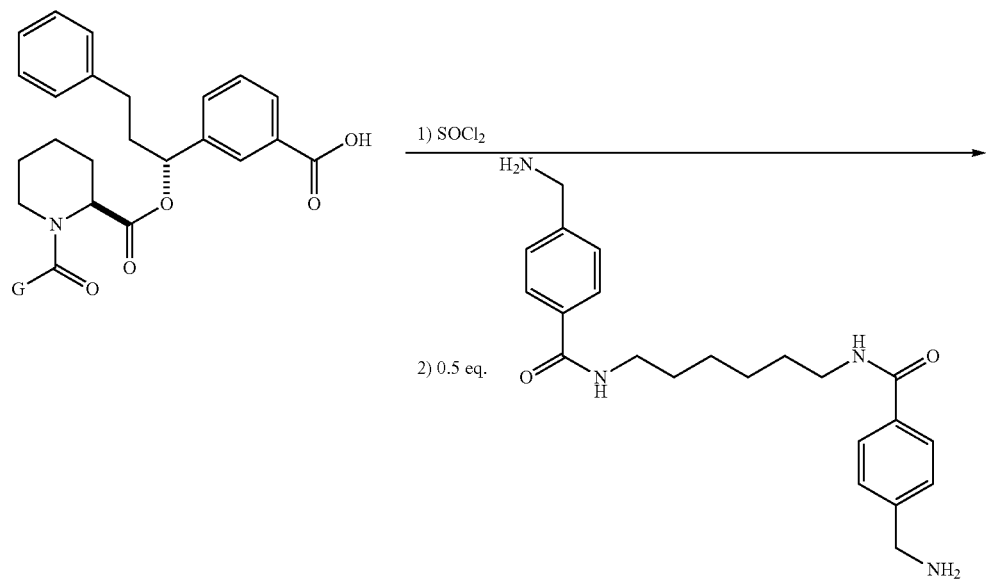

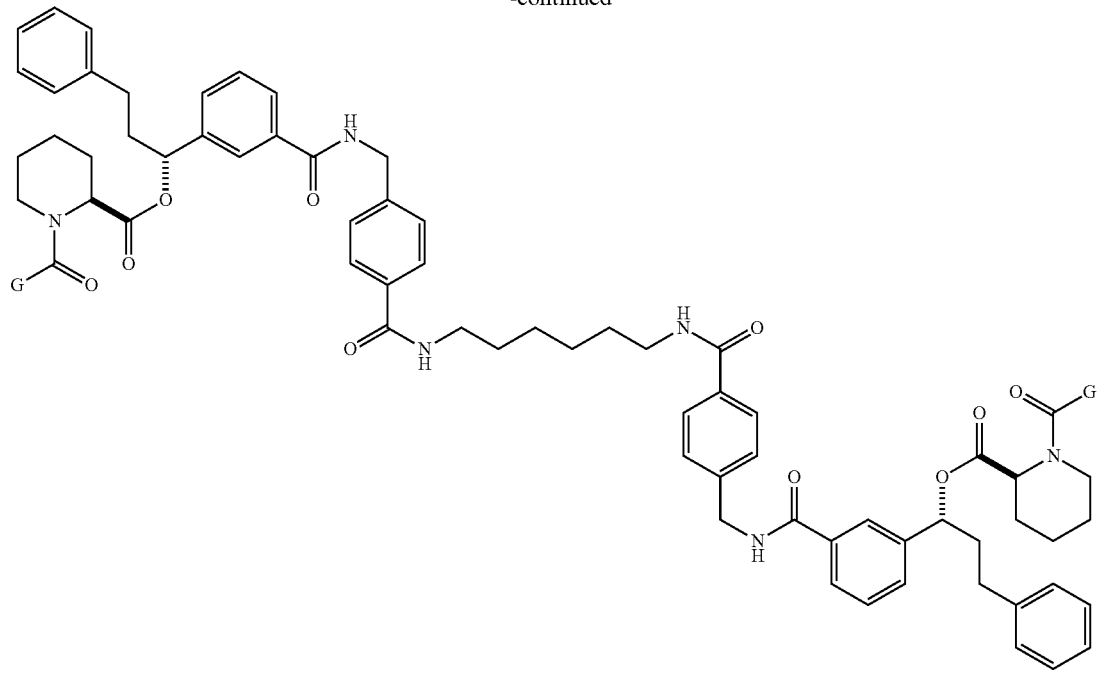

see: *Yamashita, et al. Biomed. Chem. Lett.*, 1993, 4, 325-328.

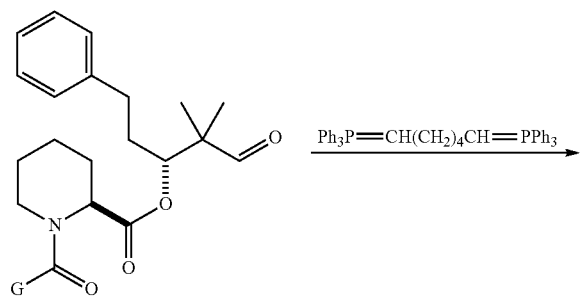

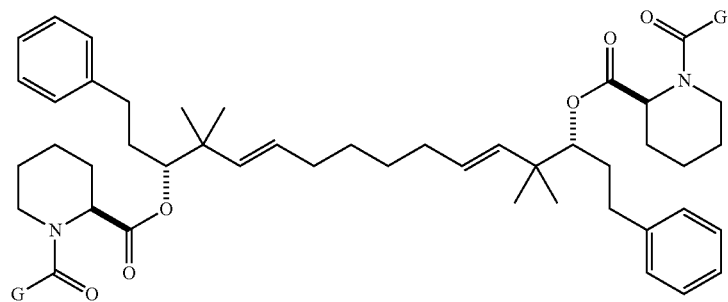

see: *Yamashita, et al. Biomed. Chem Lett.*, 1993, 4, 325-328.

Heterodimers (e.g., where $M^1 \neq M^2$) may be prepared by stepwise attachment of each monomer to the linker. Attachment methods may be different for each monomer and the linker may be non-symmetrical and/or differentially functionalized to facilitate stepwise attachment of monomers. By way of example, the following reaction schemes illustrate formation of heterodimers.

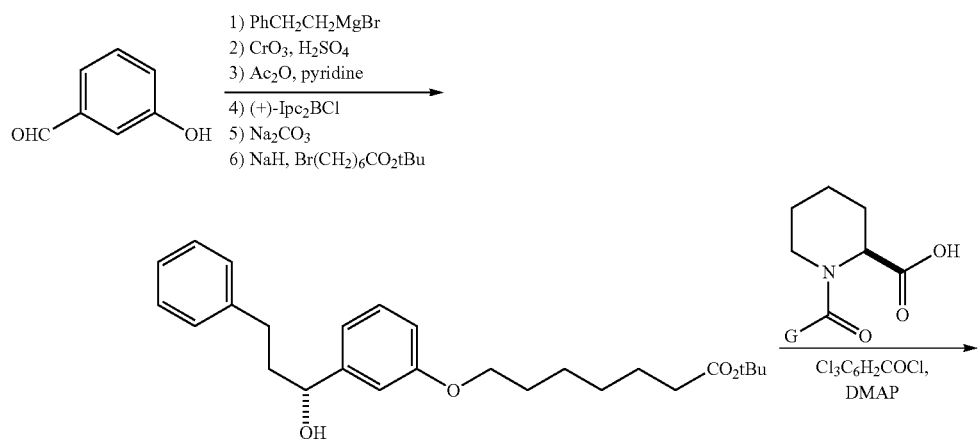
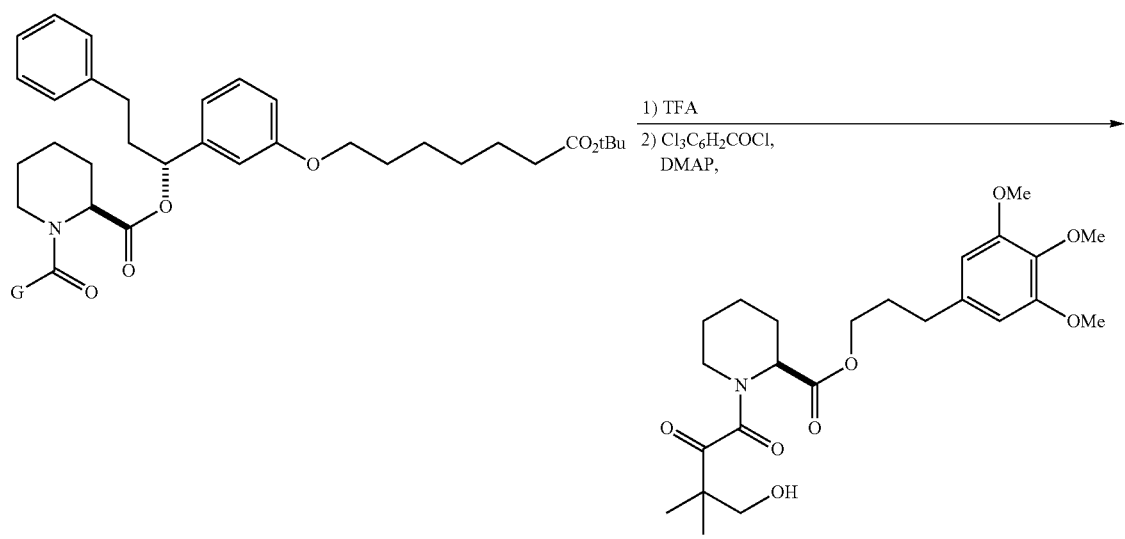
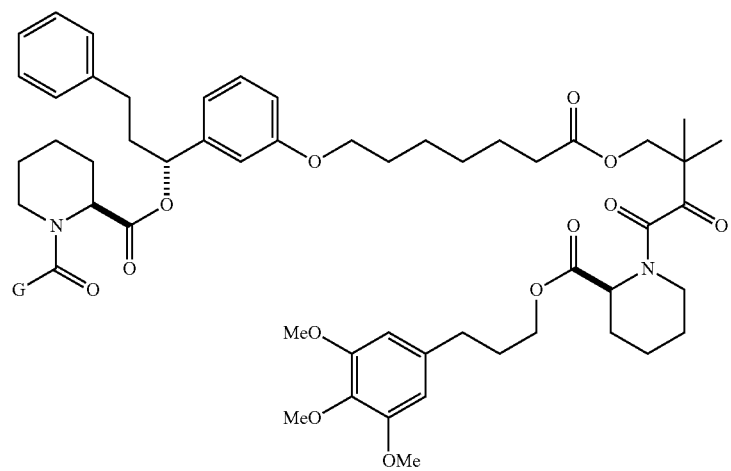

Also:
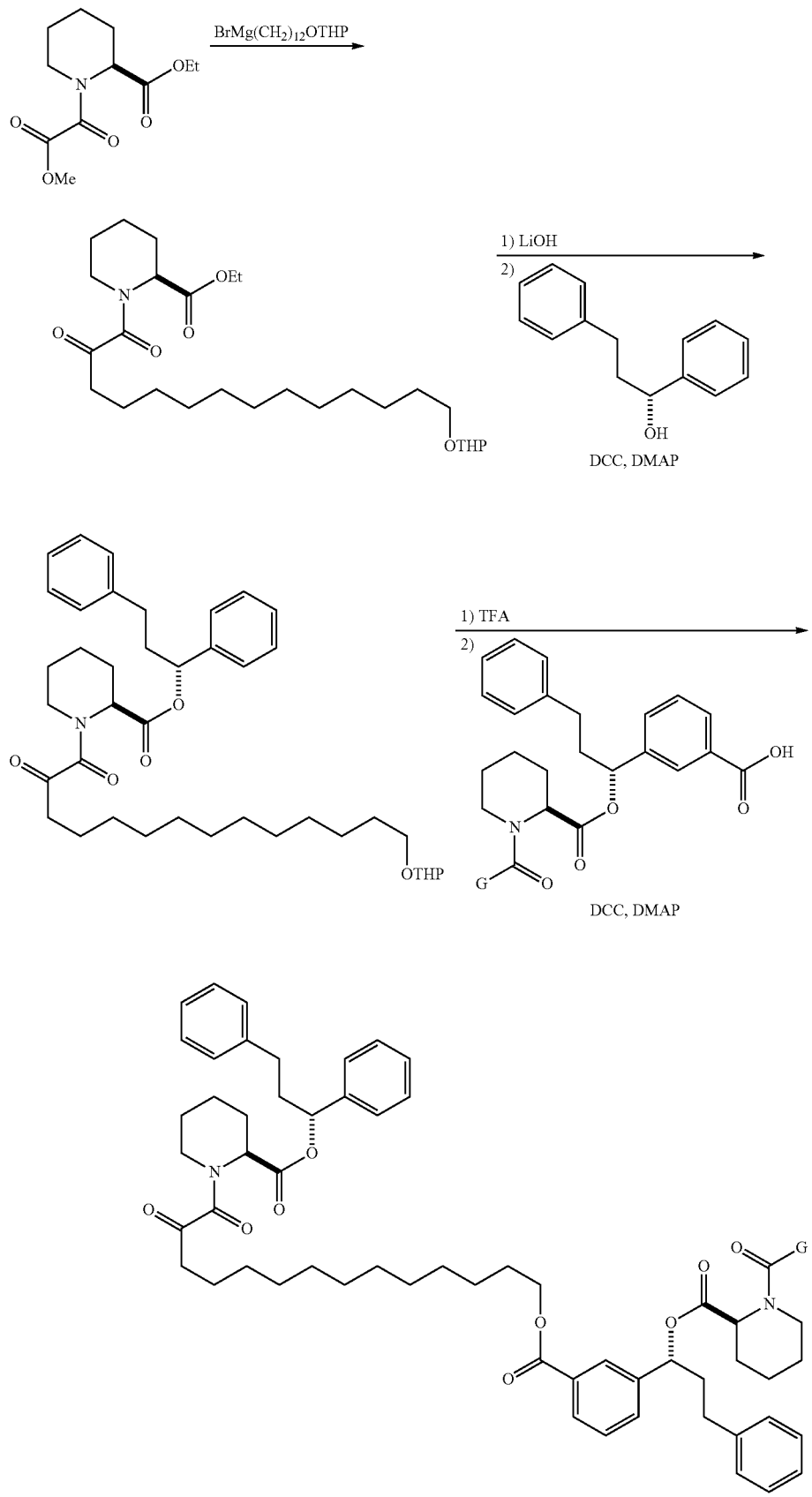

Note also:
Scheme I
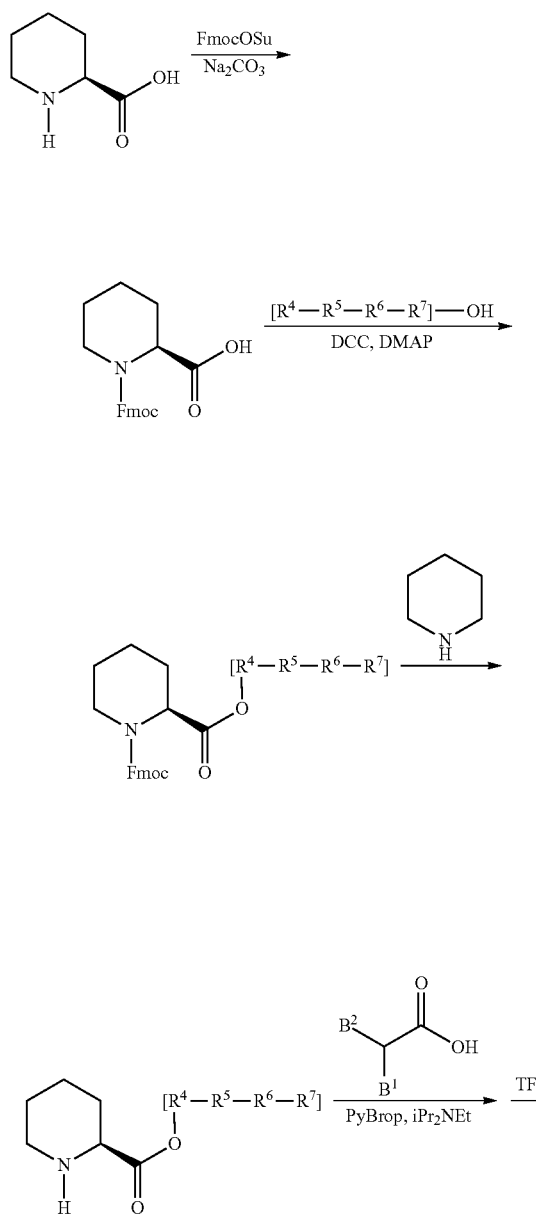
Scheme II
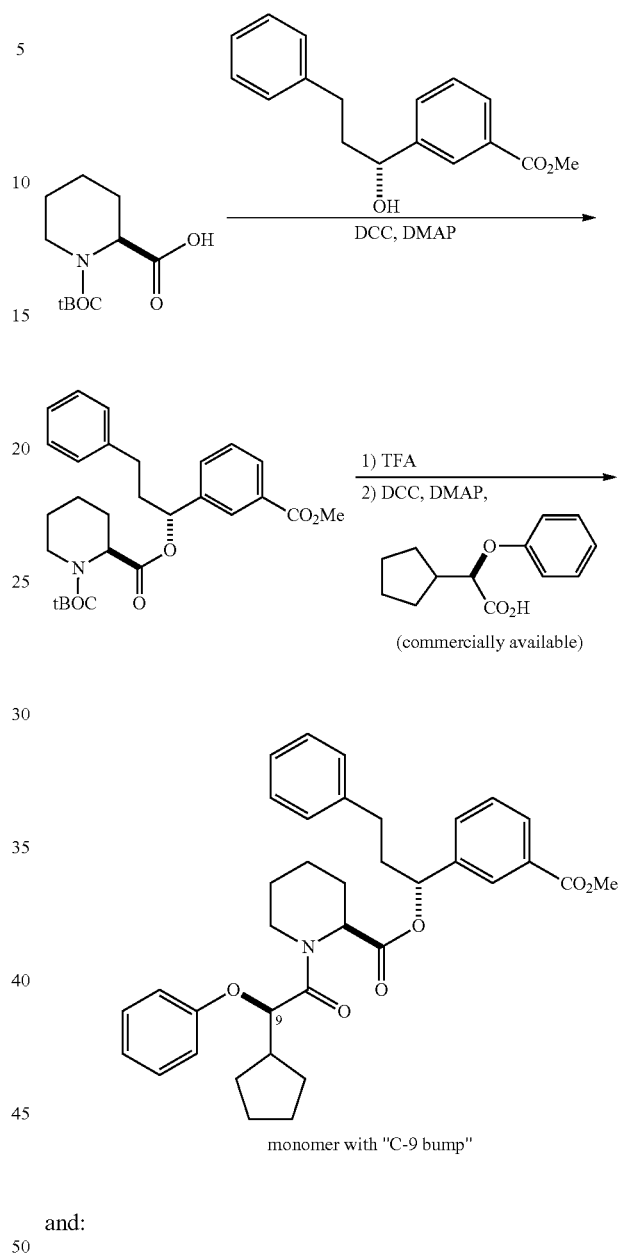
and:
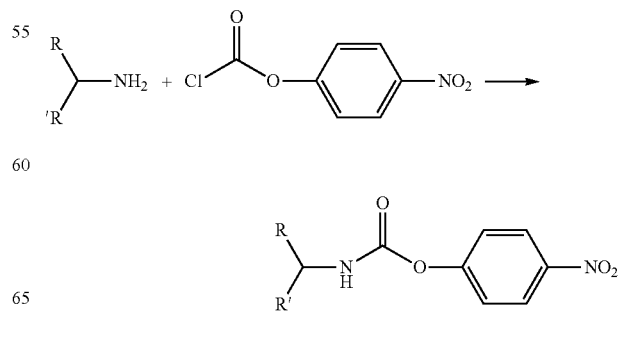

R and R' can be alkyl, protect carboxylic acid, aromatic groups such as:
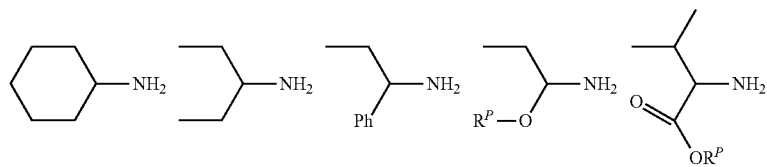
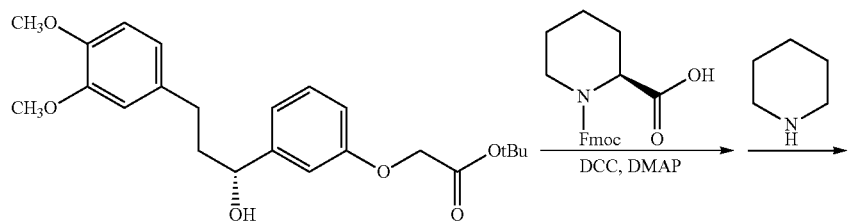
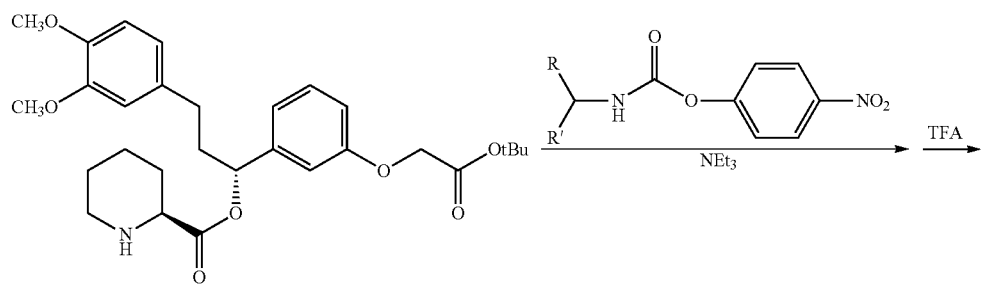
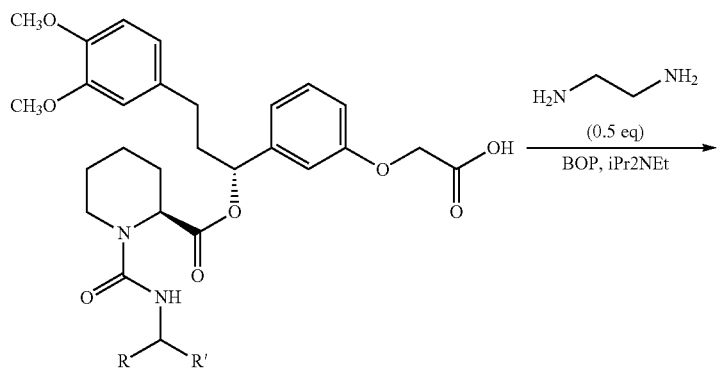
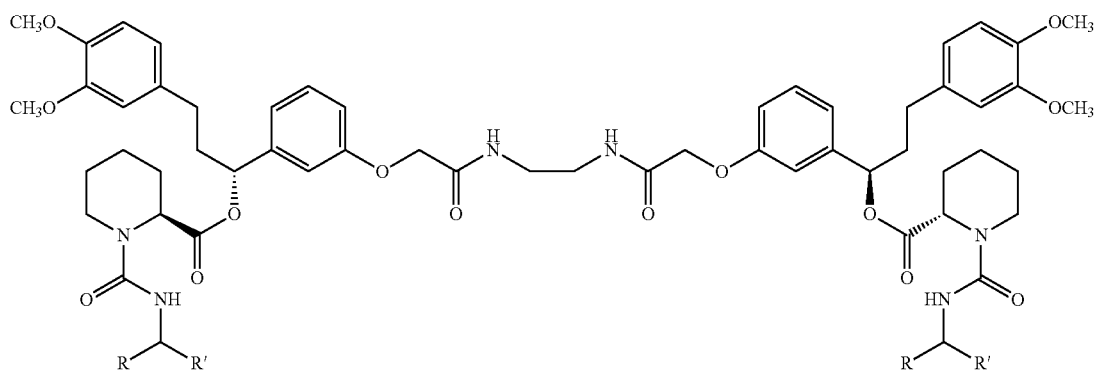

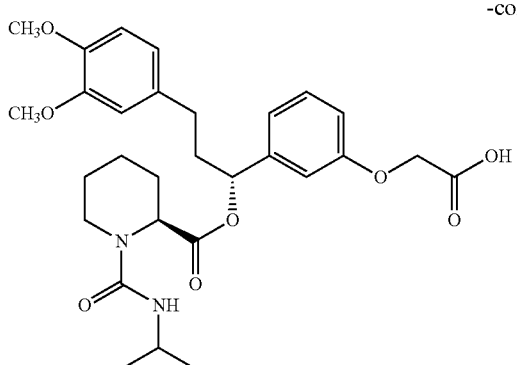

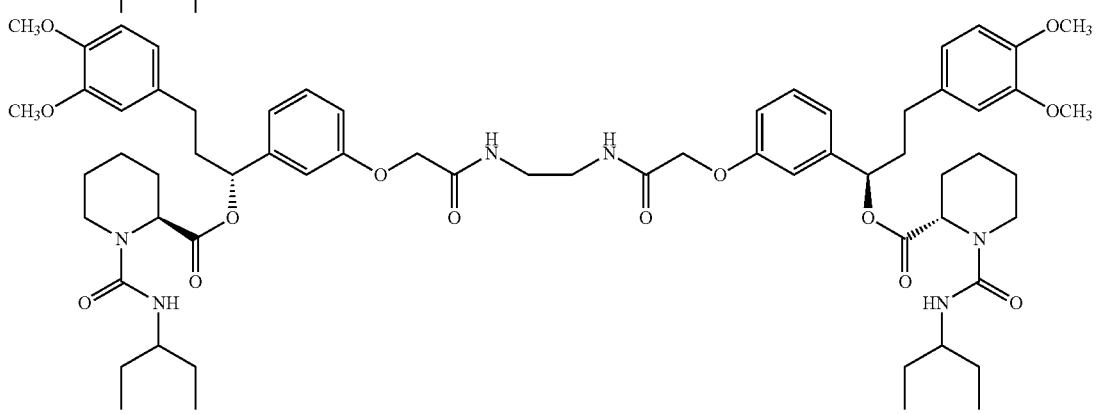

R = protecting groups

Additional Optional Modifications

In addition, compounds of this invention may comprise a substituted proline and pipecolic acid derivative, numerous examples of which have been described in the literature. Using synthetic procedures similar to those described above, substituted prolines and pipecolates can be utilized to prepare monomers with "bumps" at positions C-2 to C-6 as exemplified below.

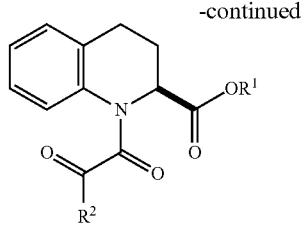

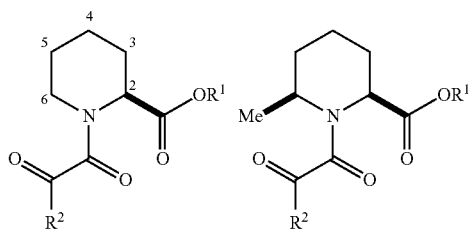

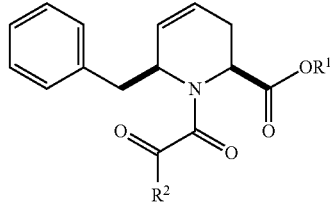

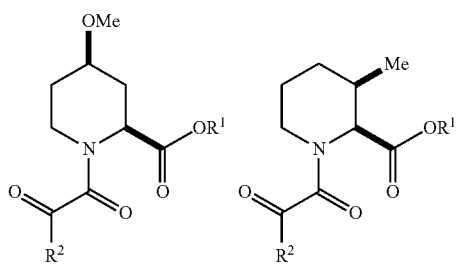

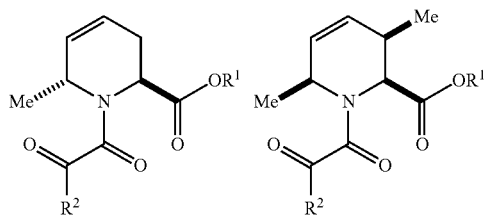

-continued

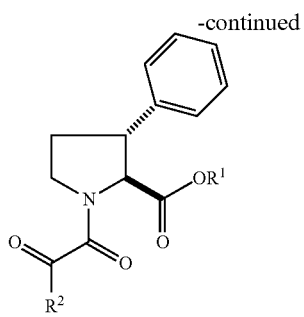

For representative examples of substituted prolines and pipecolic acids see: Chung, et al., *J. Org. Chem.,* 1990, 55, 270; Shuman, et al., *J. Org. Chem.,* 1990, 55, 738; Hanson, et al., *Tetrahedron Lett.,* 1989, 30, 5751; Bailey, et al., *Tetrahedron Lett.,* 1989, 30, 6781.

FKBP Domains

FKBPs (FK506 binding proteins) are the cytosolic receptors for macrolides such as FK506, FK520 and rapamycin and are highly conserved across species lines. Information concerning the nucleotide sequences, cloning, and other aspects of various FKBP species is already known in the art, permitting the synthesis or cloning of DNA encoding the desired FKBP peptide sequence, e.g., using well known methods and PCR primers based on published sequences. See e.g. Staendart et al, 1990, Nature 346, 671-674 (human FKBP12); Kay, 1996, Biochem. J. 314, 361-385 (review). Homologous FKBP proteins in other mammalian species, in yeast, and in other organisms are also known in the art and may be used in the fusion proteins to be multimerized by compounds of this invention. See e.g. Kay, 1996, Biochem. J. 314, 361-385 (FKBP review). The size of FKBP domains for such use varies, depending on which FKBP protein is employed. An FKBP peptide sequence for use in such fusion proteins will be capable of binding to a multimerizing agent of this invention and associating with other such fusion proteins, which may be the same or different. Multimerizer-mediated protein-protein association may be determined by direct or indirect means, known in the art. The FKBP peptide sequence may comprise a naturally occurring peptide sequence derived from the human FKBP12 protein or a peptide sequence derived from another human FKBP, from a murine or other mammalian FKBP, or from some other animal, yeast or fungal FKBP; may contain up to about ten (preferably 1-5) amino acid substitutions, insertions or deletions within that region relative to the naturally occurring sequence; may be a peptide sequence encoded by a DNA sequence capable of selectively hybridizing to a DNA molecule encoding a naturally occurring FKBP or may be encoded by a DNA sequence which would be capable, but for the degeneracy of the genetic code, of selectively hybridizing to a DNA molecule encoding a naturally occurring FKBP. "Capable of selectively hybridizing" as that phrase is used herein means that two DNA molecules are susceptible to hybridization with one another, despite the presence of other DNA molecules, under hybridization conditions which can be chosen or readily determined empirically by the practitioner of ordinary skill in this art. Such treatments include conditions of high stringency such as washing extensively with buffers containing 0.2 to 6×SSC, and/or containing 0.1% to 1% SDS, at temperatures ranging from room temperature to 65-75° C. See for example F. M. Ausubel et al., Eds, Short Protocols in Molecular Biology, Units 6.3 and 6.4 (John Wiley and Sons, New York, 3d Edition, 1995).

FKBP domains, wild-type or modified, may be utilized in the context of fusion proteins expressed in genetically engineered cells to render the cells susceptible to multimerizer-dependent transcription of a heterologous or endogenous target gene, cell death, cell proliferation, deletion of a gene, or other biological event, as described in detail in WO 94/18317, WO 95/02684, WO 96/20951, WO 95/41865, the full contents of each of which is incorporated herein by reference.

Illustrative examples of FKBP chimeras useful in the practice of this invention include the FKBP fusion proteins disclosed in PCT/US94/01617 (Stanford & Harvard), PCT/US94/08008 (Stanford & Harvard), Spencer et al (supra), PCT/US95/10591 (ARIAD) and PCT/US95/06722 (Mitotix, Inc.); FKBP domains derived from a non-human source; variants of any of the foregoing FKBP fusion proteins which contain up to 10 (preferably 1-5) amino acid insertions, deletions or substitutions in one or more of the FKBP domains and which are still capable of binding to FK506, rapamycin or a compound of this invention; and variants of any of the foregoing FKBP fusion proteins which contain one or more amino acid residues corresponding to Tyr26, Phe36, Asp37, Arg42, Phe46, Phe48, Glu54, Val55, or Phe99 of human FKBP12 in which one or more of those amino acid residues is replaced by a different amino acid, the variant being capable of binding to a compound of this invention. Numerous mutant FKBP domains and fusion proteins containing them are disclosed in the various references cited in this section, including by way of illustration, FKBPs in which phenylalanine at position 36 is replaced with an amino acid having a less bulky side chain, e.g. alanine, valine, methionin or serine.

Binding Properties, Assays

The multimerizing agents of this invention preferably do not measurably participate in a ternary complex with both immunophilin and calcineurin, or with immunophilin and FRAP (Brown et al., *Nature,* 1994, 369, 756-758), and are therefore not immunosuppressive like FK506 or rapamycin. Additionally, it will often be preferred that the multimerizing agent be physiologically acceptable (i.e., lack undue toxicity toward the cell or organism with which it is to be used), can be taken orally by animals (i.e., is orally active in applications in whole animals, including gene therapy), and/or can cross cellular and other membranes, as necessary for a particular application.

In certain applications, preferred multimerizers are those which bind, or comprise monomeric moieties, M, which bind, preferentially to mutant immunophilins (by way of non-limiting example, a human FKBP in which Phe36 is replaced with a different amino acid, preferably an amino acid with a less bulky R group such as valine or alanine) over native or naturally-occurring immunophilins. For example, such compounds may bind preferentially to mutant FKBPs at least an order of magnitude better than they bind to human FKBP12, and in some cases may bind to mutant FKBPs greater than 2 or even 3 or more orders of magnitude better than they do to human FKBP12, as determined by any scientifically valid or art-accepted assay methodology.

Binding affinities of various multimerizing agents of this invention or their component monomers with respect to human FKBP12, variants thereof or other immunophilin proteins may be determined by adaptation of known methods used in the case of FKBP. For instance, the practitioner may measure the ability of a compound of this invention to compete with the binding of a known ligand to the protein of interest. See e.g. Sierkierka et al, 1989, Nature 341, 755-757 (test compound competes with binding of labeled FK506 derivative to FKBP). One set of preferred multimerizing agents of this invention bind, or contain at least one component monomer which binds, to human FKBP12, to a mutant thereof as discussed above, or a fusion protein containing such FKBP domain, with a Kd value below about 200 nM, more preferably below about 50 nM, even more preferably below about 10 nM, and even more preferably below about 1 nM, as measured by direct binding measurement (e.g. fluorescence quenching), competition binding measurement (e.g. versus FK506), inhibition of FKBP enzyme activity (rotamase), or other assay methodology. In one subset of such compounds, the FKBP domain is one in which phenylalanine at position 36 has been replaced with an amino acid having a less bulky side chain, e.g. alanine, valine, methionin or serine.

A Competitive Binding FP Assay is described in detail in the examples which follow. That assay permits the in vitro measurement of an 1050 value for a given compound which reflects its ability to bind to an FKBP protein in competition with a labeled FKBP ligand, such as, for example, FK506.

One preferred class of compounds of this invention are those multimerizing agents or monomers which have an IC50 value in the Competitive Binding FP Assay better than 1000 nM, preferably better than 300 nM, more preferably better than 100 nM, and even more preferably better than 10 nM with respect to a given FKBP domain and ligand pair, e.g. human FKBP12 or a variant thereof with up to 10, preferably up to 5 amino add replacements, with a flouresceinated FK506 standard. In one subset of that class, the FKBP domain has one of the abovementioned modifications at position 36.

The ability of the multimerizing agents to multimerize chimeric proteins may be measured cell-based assays by measuring the occurrence of an event triggered by such multimerization. For instance, one may use cells containing and capable of expressing DNAs encoding chimeric proteins comprising one or more immunophilin-derived ligand binding domains and one or more effector domains capable, upon multimerization, of actuating a biological response. We prefer to use cells which further contain a reporter gene under the transcriptional control of a regulatory element (i.e., promoter) which is responsive to the multimerization of the chimeric proteins (at least one of which contains an FKBP domain). The design and preparation of illustrative components and their use in so engineering cells is described in PCT/US94/01617 and the other international patent applications referred to in this and the foregoing section. The cells are grown or maintained in culture. A multimerizing agent is added to the culture medium and after a suitable incubation period (to permit gene expression and secretion, e.g. several hours or overnight) the presence of the reporter gene product is measured. Positive results, i.e., multimerization, correlates with transcription of the reporter gene as observed by the appearance of the reporter gene product. The reporter gene product may be a conveniently detectable protein (e.g. by ELISA) or may catalyze the production of a conveniently detectable product (e.g. colored). Materials and methods for producing appropriate cell lines for conducting such assays are disclosed in the international patent applications cited above in this section. Typically used target genes include by way of example SEAP, beta-galactosidase, Green Fluorescent Protein and luciferase as well as proteins such as hGH for which convenient assays are commercially available.

Another preferred class of compounds of this invention are those which are capable of inducing a detectable signal in a 2-hybrid transcription assay based on fusion proteins containing an FKBP domain. Preferably, the FKBP domain is an FKBP domain other than wild-type human FKBP12.

Another assay for measuring the ability of the multimerizing agents to multimerize chimeric proteins, like the FKBP-based transcription assay, is a cell-based assay which measures the occurrence of an event triggered by such multimerization. In this case, one uses cells which constitutively express a detectable product. The cells also contain and are capable of expressing DNAs encoding chimeric proteins comprising one or more immunophilin-derived ligand binding domains and one or more effector domains, such as the intracellular domain of FAS, capable, upon multimerization, of triggering cell death. The design and preparation of illustrative components and their use in so engineering cells is described in WO 95/02684. See also WO 96/41865. The cells are maintained or cultured in a culture medium permitting cell growth or continued viability. The cells or medium are assayed for the presence of the constitutive cellular product, and a base-line level of reporter is thus established. One may use cells engineered for constitutive production of hGH or any other conveniently detectable product to serve as the reporter. The compound to be tested is added to the medium, the cells are incubated, and the cells or medium is tested for the presence of reporter at one or more time points. Decrease in reporter production indicates cell death, an indirect measure of multimerization of the fusion proteins.

Another preferred class of compounds of this invention are those which are capable of inducing a detectable signal in such an FKBP-based apoptosis assay. Preferably, the FKBP domain is an FKBP domain other than wild-type human FKBP12. In some cases, the FKBP domain is modified at position 36, as discussed above.

Conducting such assays permits the practitioner to select multimerizing agents possessing the desired EC50 values and/or binding preference for a mutant FKBP over wild-type human FKBP12. The Competitive Binding FP Assay permits one to select monomers or multimerizing agents which possess the desired IC50 values and/or binding preference for a mutant KFBP or wild-type FKBP relative to a control, such as FK506.

Monomers and Synthetic Intermediates

Monomers, M, of formula II disclosed herein are also useful, both as synthetic intermediates, e.g. in the synthesis of dimerizing agents as disclosed in detail herein, and in their own right in view of their binding affinity for immunophilins or modified immunophilins. They may be administered to the engineered cells, or to organisms containing them (preferably in a composition as described above in the case of administration to whole animals), in an amount effective for reversing or blocking the effect of the multimerizing agent, i.e. for preventing, inhibiting or disrupting multimerization.

It should be noted that compounds of this invention include mixed multimerizing agents of the formula M-L-Q, in which M is a synthetic monomer such as described herein, covalently linked by linker, L, to Q a natural product immunophilin ligand such as FK506, FK520, rapamycin, cyclosporin A, or an analog or derivative thereof. Numerous such ligands and analogs and derivatives thereof are known in the art which may be linked to synthetic monomers using materials and methods described e.g. in PCT/US94/01667 and PCT/US95/10559.

Uses

The multimerizing agents can be used as described in WO 94/18317, WO 95/02684, WO 96/20951, WO 95/41865, e.g. to regulatably activate the transcription of a desired gene, delete a target gene, actuate apoptosis, or trigger other biological events in engineered cells growing in culture or in whole organisms, including in gene therapy applications. The engineered cells contain and are capable of expressing DNAs encoding proteins containing one or more immunophilin domains, such as an FKBP domain or mutant FKBP domain, which are capable of binding to the monomers or to multimerizing agents comprising such monomers such as depicted in the various formulas herein and in the many examples disclosed herein. In such applications, the multimerizing agent is administered to the cell culture or to the organism containing the cells, as the case may be, in an amount effective to multimerize the proteins containing the corresponding ligand-binding domains (as may be observed by monitoring the transcription, apoptosis or other biological process so triggered). Thus, this invention provides a method for regulatably triggering one of the foregoing biological processes by administering a multimerizing agent of this invention which is capable of binding to fusion proteins expressed in the genetically engineered cells to be treated. In the case of administration to whole organisms, the multimerizing agent may be administered in a composition containing the multimerizing agent and acceptable veterinary or pharmaceutical diluents and/or excipients.

Formulations, Dosage and Administration

By virtue of its capacity to promote protein-protein interactions, a multimerizer of this invention may be used in pharmaceutical compositions and methods for promoting formation of complexes of chimeric proteins of this invention in a human or non-human mammal containing genetically engineered cells of this invention.

The preferred method of such treatment or prevention is by administering to the mammal an effective amount of the compound to promote measurable formation of such complexes in the engineered cells, or preferably, to promote measurable actuation of the desired biological event triggered by such complexation, e.g. transcription of a target gene, apoptosis of engineered cells, etc.

Therapeutic/Prophylactic Administration & Pharmaceutical Compositions

The multimerizers can exist in free form or, where appropriate, in salt form. Pharmaceutically acceptable salts of many types of compounds and their preparation are well-known to those of skill in the art. The pharmaceutically acceptable salts of compounds of this invention include the conventional non-toxic salts or the quaternary ammonium salts of such compounds which are formed, for example, from inorganic or organic acids of bases.

The compounds of the invention may form hydrates or solvates. It is known to those of skill in the art that charged compounds form hydrated species when lyophilized with water, or form solvated species when concentrated in a solution with an appropriate organic solvent.

This invention also relates to pharmaceutical compositions comprising a therapeutically (or prophylactically) effective amount of the compound, and a pharmaceutically acceptable carrier or excipient. Carriers include e.g. saline, buffered saline, dextrose, water, glycerol, ethanol, and combinations thereof, and are discussed in greater detail below. The composition, if desired, can also contain minor amounts of wetting or emulsifying agents, or pH buffering agents. The composition can be a liquid solution, suspension, emulsion, tablet, pill, capsule, sustained release formulation, or powder. The composition can be formulated as a suppository, with traditional binders and carriers such as triglycerides. Oral formulation can include standard carriers such as pharmaceutical grades of mannitol, lactose, starch, magnesium stearate, sodium saccharine, cellulose, magnesium carbonate, etc. Formulation may involve mixing, granulating and compressing or dissolving the ingredients as appropriate to the desired preparation.

The pharmaceutical carrier employed may be, for example, either a solid or liquid.

Illustrative solid carrier include lactose, terra alba, sucrose, talc, gelatin, agar, pectin, acacia, magnesium stearate, stearic acid and the like. A solid carrier can include one or more substances which may also act as flavoring agents, lubricants, solubilizers, suspending agents, fillers, glidants, compression aids, binders or tablet-disintegrating agents; it can also be an encapsulating material. In powders, the carrier is a finely divided solid which is in admixture with the finely divided active ingredient. In tablets, the active ingredient is mixed with a carrier having the necessary compression properties in suitable proportions, and compacted in the shape and size desired. The powders and tablets preferably contain up to 99% of the active ingredient. Suitable solid carriers include, for example, calcium phosphate, magnesium stearate, talc, sugars, lactose, dextrin, starch, gelatin, cellulose, methyl cellulose, sodium carboxymethyl cellulose, polyvinylpyrrolidine, low melting waxes and ion exchange resins.

Illustrative liquid carriers include syrup, peanut oil, olive oil, water, etc. Liquid carriers are used in preparing solutions, suspensions, emulsions, syrups, elixirs and pressurized compositions. The active ingredient can be dissolved or suspended in a pharmaceutically acceptable liquid carrier such as water, an organic solvent, a mixture of both or pharmaceutically acceptable oils or fats. The liquid carrier can contain other suitable pharmaceutical additives such as solubilizers, emulsifiers, buffers, preservatives, sweeteners, flavoring agents, suspending agents, thickening agents, colors, viscosity regulators, stabilizers or osmo-regulators. Suitable examples of liquid carriers for oral and parenteral administration include water (partially containing additives as above, e.g. cellulose derivatives, preferably sodium carboxymethyl cellulose solution), alcohols (including monohydric alcohols and polyhydric alcohols, e.g. glycols) and their derivatives, and oils (e.g. fractionated coconut oil and arachis oil). For parenteral administration, the carrier can also be an oily ester such as ethyl oleate and isopropyl myristate. Sterile liquid carriers are useful in sterile liquid form compositions for parenteral administration. The liquid carrier for pressurized compositions can be halogenated hydrocarbon or other pharmaceutically acceptable propellant. Liquid pharmaceutical compositions which are sterile solutions or suspensions can be utilized by, for example, intramuscular, intraperitoneal or subcutaneous injection. Sterile solutions can also be administered intravenously. The compound can also be administered orally either in liquid or solid composition form.

The carrier or excipient may include time delay material well known to the art, such as glyceryl monostearate or glyceryl distearate along or with a wax, ethylcellulose, hydroxypropylmethylcellulose, methylmethacrylate and the like. When formulated for oral administration, 0.01% Tween 80 in PHOSAL PG-50 (phospholipid concentrate with 1,2-propylene glycol, A. Nattermann & Cie. GmbH) has been recognized as providing an acceptable oral formulation for other compounds, and may be adapted to formulations for various compounds of this invention.

A wide variety of pharmaceutical forms can be employed. If a solid carrier is used, the preparation can be tableted, placed in a hard gelatin capsule in powder or pellet form or in the form of a troche or lozenge. The amount of solid carrier will vary widely but preferably will be from about 25 mg to about 1 g. If a liquid carrier is used, the preparation will be in the form of a syrup, emulsion, soft gelatin capsule, sterile injectable solution or suspension in an ampule or vial or nonaqueous liquid suspension.

To obtain a stable water soluble dosage form, a pharmaceutically acceptable salt of the multimerizer may be dissolved in an aqueous solution of an organic or inorganic acid, such as a 0.3M solution of succinic acid or citric acid. Alternatively, acidic derivatives can be dissolved in suitable basic solutions. If a soluble salt form is not available, the compound is dissolved in a suitable cosolvent or combinations thereof. Examples of such suitable cosolvents include, but are not limited to, alcohol, propylene glycol, polyethylene glycol 300, polysorbate 80, glycerin, polyoxyethylated fatty acids, fatty alcohols or glycerin hydroxy fatty acids esters and the like in concentrations ranging from 0-60% of the total volume.

Various delivery systems are known and can be used to administer the multimerizer, or the various formulations thereof, including tablets, capsules, injectable solutions, encapsulation in liposomes, microparticles, microcapsules, etc. Methods of introduction include but are not limited to dermal, intradermal, intramuscular, intraperitoneal, intravenous, subcutaneous, intranasal, pulmonary, epidural, ocular and (as is usually preferred) oral routes. The compound may be administered by any convenient or otherwise appropriate route, for example by infusion or bolus injection, by absorption through epithelial or mucocutaneous linings (e.g., oral mucosa, rectal and intestinal mucosa, etc.) and may be administered together with other biologically active agents. Administration can be systemic or local. For treatment or prophylaxis of nasal, bronchial or pulmonary conditions, preferred routes of administration are oral, nasal or via a bronchial aerosol or nebulizer.

In certain embodiments, it may be desirable to administer the compound locally to an area in need of treatment; this may be achieved by, for example, and not by way of limitation, local infusion during surgery, topical application, by injection, by means of a catheter, by means of a suppository, or by means of a skin patch or implant, said implant being of a porous, non-porous, or gelatinous material, including membranes, such as sialastic membranes, or fibers.

In a specific embodiment, the composition is formulated in accordance with routine procedures as a pharmaceutical composition adapted for intravenous administration to human beings. Typically, compositions for intravenous administration are solutions in sterile isotonic aqueous buffer. Where necessary, the composition may also include a solubilizing agent and a local anesthetic to ease pain at the side of the injection. Generally, the ingredients are supplied either separately or mixed together in unit dosage form, for example, as a lyophilized powder or water free concentrate in a hermetically sealed container such as an ampoule or sachette indicating the quantity of active agent. Where the composition is to be administered by infusion, it can be dispensed with an infusion bottle containing sterile pharmaceutical grade water or saline. Where the composition is administered by injection, an ampoule of sterile water for injection or saline can be provided so that the ingredients may be mixed prior to administration.

Administration to an individual of an effective amount of the compound can also be accomplished topically by administering the compound(s) directly to the affected area of the skin of the individual. For this purpose, the compound is administered or applied in a composition including a pharmacologically acceptable topical carrier, such as a gel, an ointment, a lotion, or a cream, which includes, without limitation, such carriers as water, glycerol, alcohol, propylene glycol, fatty alcohols, triglycerides, fatty acid esters, or mineral oils.

Other topical carriers include liquid petroleum, isopropyl palmitate, polyethylene glycol, ethanol (95%), polyoxyethylene monolaurate (5%) in water, or sodium lauryl sulfate (5%) in water. Other materials such as anti-oxidants, humectants, viscosity stabilizers, and similar agents may be added as necessary. Percutaneous penetration enhancers such as Azone may also be included.

In addition, in certain instances, it is expected that the compound may be disposed within devices placed upon, in, or under the skin. Such devices include patches, implants, and injections which release the compound into the skin, by either passive or active release mechanisms.

Materials and methods for producing the various formulations are well known in the art and may be adapted for practicing the subject invention. See e.g. U.S. Pat. Nos. 5,182,293 and 4,837,311 (tablets, capsules and other oral formulations as well as intravenous formulations) and European Patent Application Publication Nos. 0 649 659 (published Apr. 26, 1995; illustrative formulation for IV administration) and 0 648 494 (published Apr. 19, 1995; illustrative formulation for oral administration).

The effective dose of the compound will typically be in the range of about 0.01 to about 50 mg/kgs, preferably about 0.1 to about 10 mg/kg of mammalian body weight, administered in single or multiple doses. Generally, the compound may be administered to patients in need of such treatment in a daily dose range of about 1 to about 2000 mg per patient.

The amount of compound which will be effective in the treatment or prevention of a particular disorder or condition will depend in part on the characteristics of the fusion proteins to be multimerized, the characteristics and location of the genetically engineered cells, and on the nature of the disorder or condition, which can be determined by standard clinical techniques. In addition, in vitro or in vivo assays may optionally be employed to help identify optimal dosage ranges. Effective doses may be extrapolated from dose-response curves derived from in vitro or animal model test systems. The precise dosage level should be determined by the attending physician or other health care provider and will depend upon well known factors, including route of administration, and the age, body weight, sex and general health of the individual; the nature, severity and clinical stage of the disease; the use (or not) of concomitant therapies; and the nature and extent of genetic engineering of cells in the patient.

The invention also provides a pharmaceutical pack or kit comprising one or more containers filled with one or more of the ingredients of the pharmaceutical compositions of the invention. Optionally associated with such container(s) can be a notice in the form prescribed by a governmental agency regulating the manufacture, use or sale of pharmaceutical or biological products, which notice reflects approval by the agency of manufacture, use or sale for human administration.

EXAMPLES

Synthetic Overview, Part I

The synthesis of functionalized chiral alcohols was carried out as follows. The unsubstituted chiral alcohol 1 was prepared from 3-hydroxybenzaldehyde in five steps following reported procedures by Holt et al. *J. Amer. Chem. Soc.*, 1993, 115, 9925-9938.

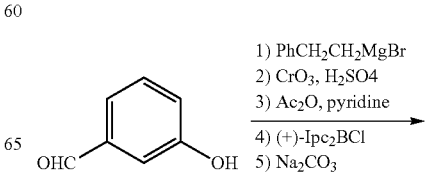

81

-continued

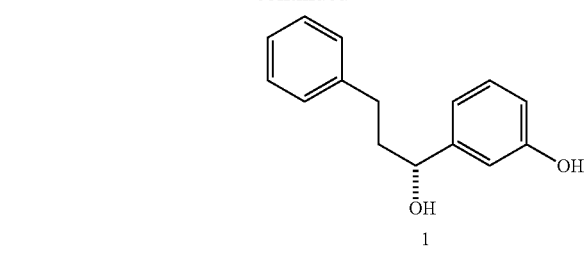

1

Alkylation of 1 with 3-N-Boc-aminopropylbromide in the presence of one equivalent of NaH gave 2 in good yield. Similarly, alkylation of 1 with tert-butyl bromoacetate provided 3.

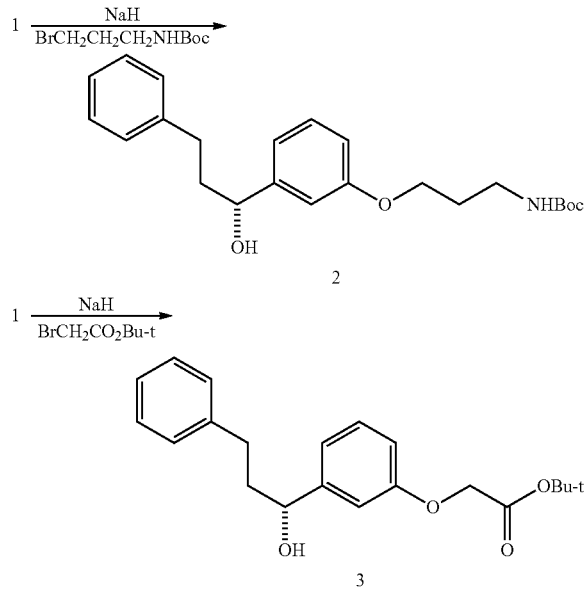

Chiral alcohols containing left-phenyl ring substitutions were prepared using a chalcone chemistry as shown in the following scheme.

4: $R_1 = R_2 = OCH_3, R_3 = H$
5: $R_1 = R_2 = R_3 = OCH_3$
6: $R_1 = R_2 = OCH_2O, R_3 = H$

82

-continued

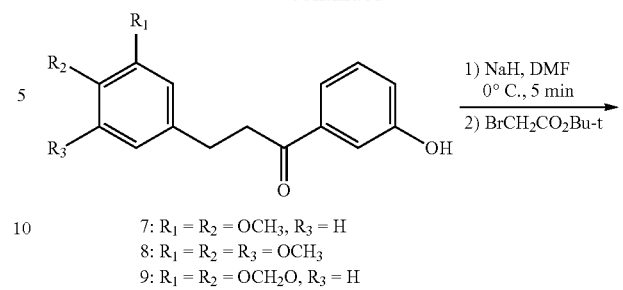

7: $R_1 = R_2 = OCH_3, R_3 = H$
8: $R_1 = R_2 = R_3 = OCH_3$
9: $R_1 = R_2 = OCH_2O, R_3 = H$

10: $R_1 = R_2 = OCH_3, R_3 = H$
11: $R_1 = R_2 = R_3 = OCH_3$
12: $R_1 = R_2 = OCH_2O, R_3 = H$

13: $R_1 = R_2 = OCH_3, R_3 = H$
14: $R_1 = R_2 = R_3 = OCH_3$
15: $R_1 = R_2 = OCH_2O, R_3 = H$

Pyridine and indole containing chiral alcohols were prepared using a similar chalcone chemistry but with some minor modifications as shown below:

16

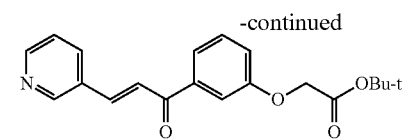

17

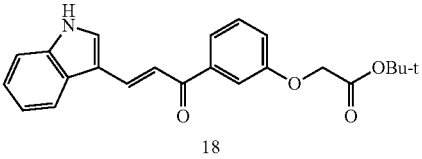

18

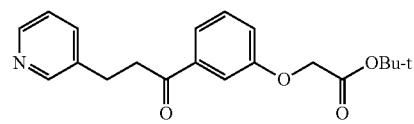

19

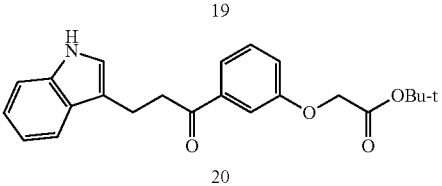

20

H₂, 10% Pd/C
EtOAc/Acetone (+)-Ipc₂BCl,
THF, -20° C.

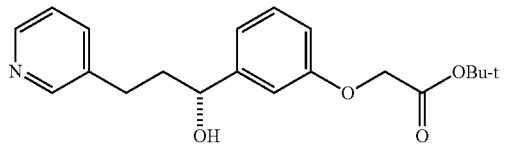

21

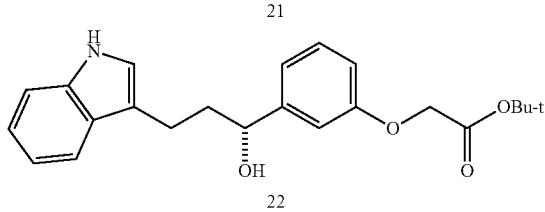

22

The carboxylic acid 23 was prepared from L-pipecolic acid in four steps following literature procedures by Holt et al. *J. Amer. Chem. Soc.,* 1993, 115, 9925-9938.

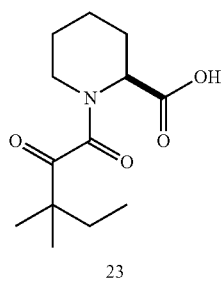

1) EtOH, HCl
2) MeO₂CCOCl
3) CH₃CH₂(CH₃)CMgCl
4) LiOH

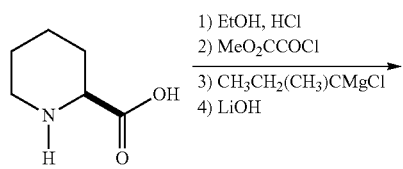

23

Coupling of 23 with 2 using DCC/DMAP and then removal of Boc-group with trifluoroacetic acid give the amine monomer 24 in good yield. The carboxylic acid monomers 25-30 were produced in a similar fashion.

23 → 1) 2, DCC, DMAP
2) CF₃CO₂H

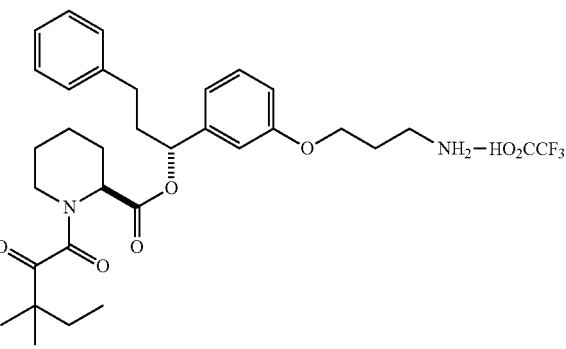

24

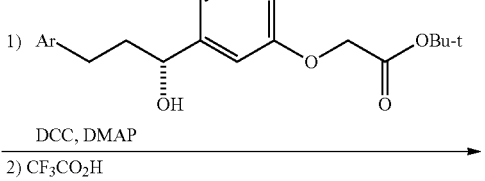

23 → DCC, DMAP
2) CF₃CO₂H

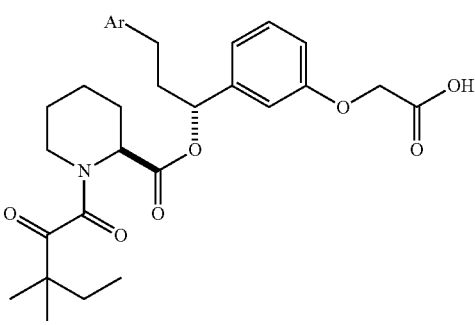

25: Ar = Ph
26: Ar = 3,4,-(OCH₃)₃Ph
27: Ar = 3,4,5-(OCH₃)₃Ph
28: Ar = 3,4-(OCH₂O)Ph
29: Ar = 3-pyridyl
30: Ar = 3-indolyl With monomers 24 and 25-30 in hand, various dimers were then synthesized. The amine 24 was treated with disuccinimidyl dicarboxylates to produce dimers 31-34 and 37, and 38. Reaction of 24 with benzene-1,3-disulfonyl chloride yielded 36. Coupling of 24 with triethylene glycol bis(chloroformate) yielded 39. Treatment of compound 34 with methyl iodide afforded 35 in quantitative yield.

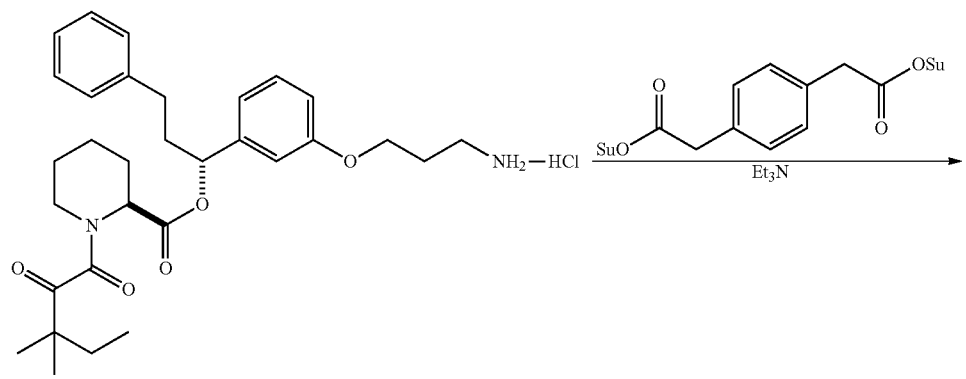
24
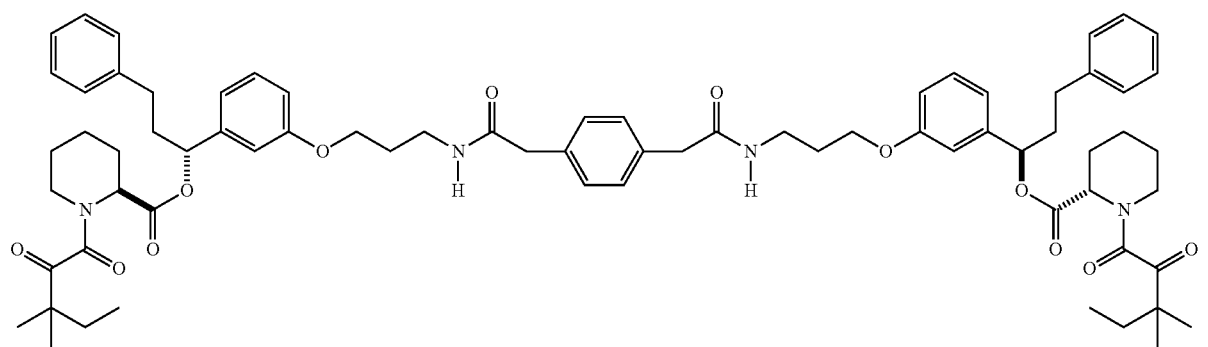
31
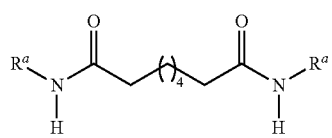
32
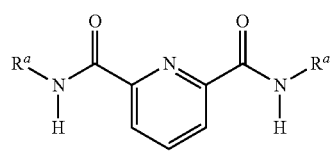
33
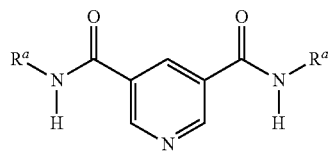
34
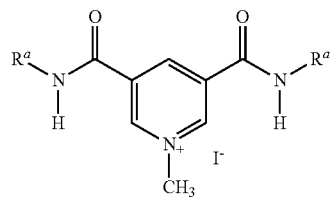
35
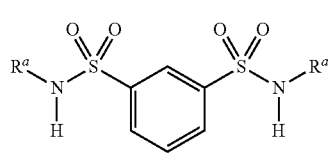
36
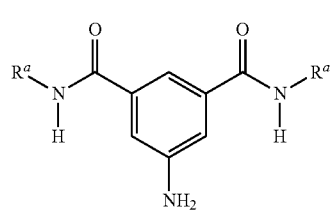
37
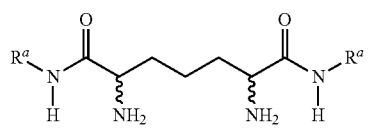
38
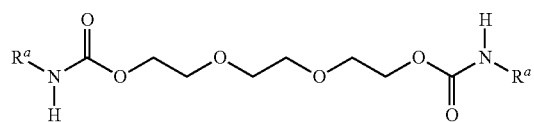
39
The acids 25-30 were converted to their activated succinimidyl esters and then coupled with various diamines to give dimers 40-63. ($R^a$ and $R^b$ groups represent the various monomers, M).

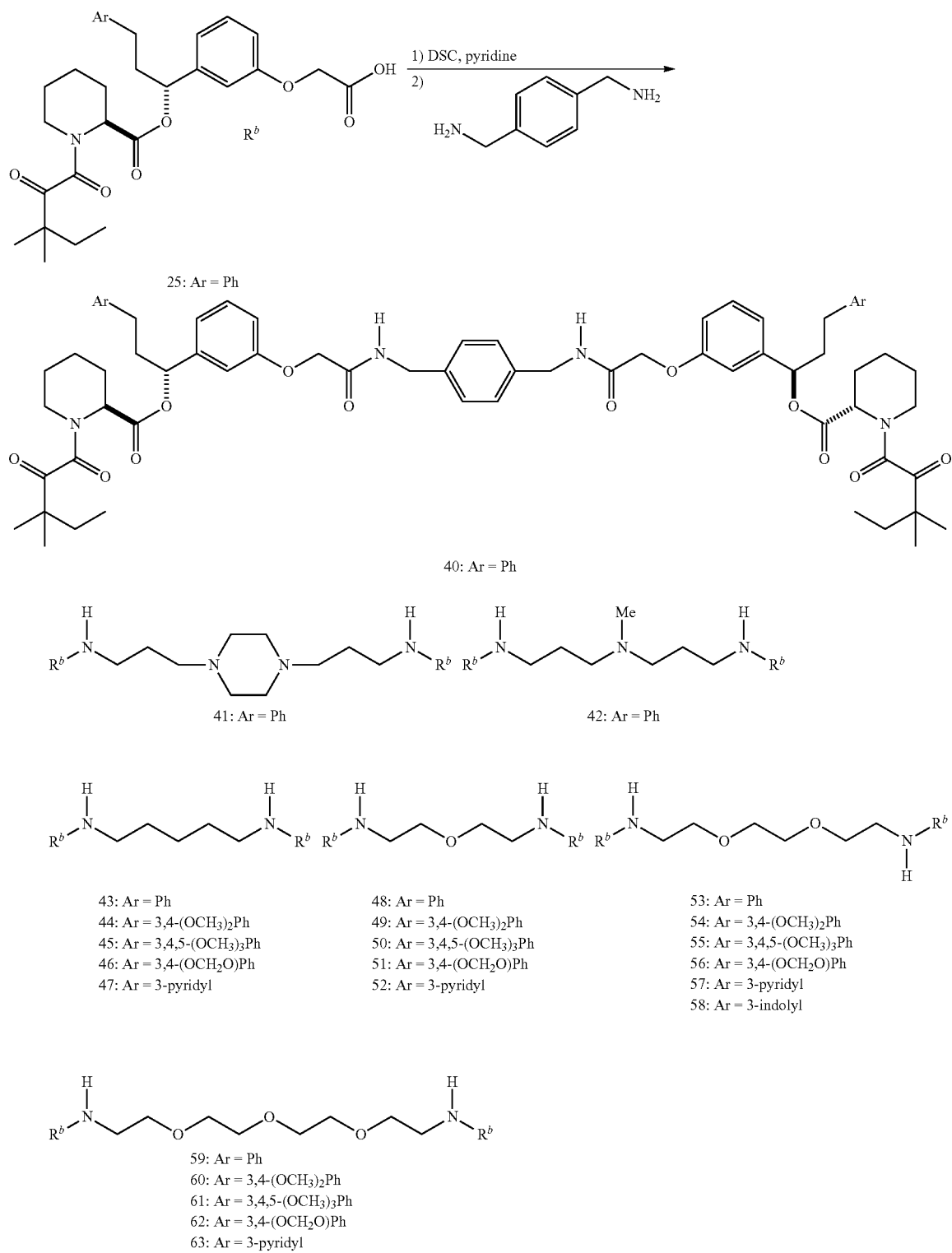
Compounds 64-67, based on the parent structure of 40 but containing the specified linkers and Ar moieties, were made by adaptation of methods described herein. The structure of the four compounds was confirmed by NMR and MS spectroscopy. All four were found to be active in cell-based transcription assays such as described infra.

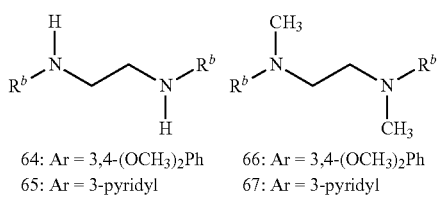

64: Ar = 3,4-(OCH3)2Ph
65: Ar = 3-pyridyl
66: Ar = 3,4-(OCH3)2Ph
67: Ar = 3-pyridyl Synthetic Details General Methods Proton and carbon magnetic resonance spectra ($^1$H, $^{13}$C NMR) were recorded on Bruker ARX-300 spectrometer. Chemical shifts are reported in parts per million (d) relative to Me$_4$Si (d 0.0). All reagents were analytical grade and were used as received. Anhydrous solvents were purchased from Aldrich in sure-seal bottles. Chromatography refers to short column chromatography using TLC grade silica gel 60 G (Merck) and the indicated solvents as the mobile phase. HPLC was conducted using a 4.6 mm×250 mm Daicel Chiracel OD column and (unless otherwise noted) a mobile phase of 85:15 hexane-propanol, flow rate of 1 mL/min, and UV detection at 210 nm. Melting points are uncorrected.

Preparation of Functionalized Chiral Alcohols (1R)-3-Phenyl-1-(3-(3-tert-butyloxycarbamoylpropyl)oxyphenyl)propan-1-ol (2)

(1R)-3-Phenyl-1-(3-hydroxyphenyl)propan-1-ol (1, 98% ee, 1.47 g, 6.45 mmol, prepared in five steps from 3-hydroxybenzaldehyde following reported procedures by Holt et al. *J. Amer. Chem. Soc.*, 1993, 115, 9925-9938) was added to a suspension of NaH (60% dispersion in mineral oil, 310 mg, 7.74 mmol) in DMF (30 mL). 3-tert-Butyloxycarbamoylpropyl bromide (3.07 g, 12.9 mmol) was then added and the resulting mixture was stirred at 40° C. under N2 overnight. The reaction was quenched with water (50 mL) and the mixture was extracted with EtOAc (250 mL). The organic layer was washed with saturated brine, dried (Na$_2$SO$_4$), and concentrated in vacuo. The mixture was redissolved in Et$_2$O (150 mL) and washed with 2 N NaOH (2×100 mL) to remove any unreacted 1 (which has the same R$_f$ as the product 2). The organic layer was then washed with saturated brine, dried (Na$_2$SO$_4$), and concentrated in vacuo. Chromatography (silica gel, 30% EtOAc/hexanes) afforded 2 (1.9 g, 77% yield, 96% ee by Chiracel HPLC: retention time 19.0 min for the (1R)-enantiomer and 15.7 min for the (1S)-enantiomer) as a colorless oil: $^1$H NMR (CDCl$_3$, 300 MHz) 7.40-6.85 (m, 9H), 4.76 (t, J=5.3 Hz, 1H), 4.12 (t, J=5.9 Hz, 2H), 3.42 (t, J=6.3 Hz, 2H), 2.80 (m, 2H), 2.10-1.85 (m, 6H), 1.53 (s, 9H); $^{13}$C NMR (CDCl$_3$, 75 MHz) 159.4, 156.4, 146.8, 142.1, 129.9, 128.83, 128.78, 126.2, 118.8, 114.0, 112.4, 74.2, 66.1, 40.8, 32.4, 30.0, 28.8. MS(FAB): (M+Na)$^+$ 408.

(1R)-3-Phenyl-1-(3-(2-tert-butyloxy-2-oxoethyl)oxyphenyl)propan-1-ol (3)

(1R)-3-Phenyl-1-(3-hydroxyphenyl)propan-1-ol (1, 98% ee, 1.7 g, 7.46 mmol, prepared in five steps from 3-hydroxybenzaldehyde following reported procedures by Holt et al. *J. Amer. Chem. Soc.*, 1993, 115, 9925-9938) was added to a suspension of NaH (60% dispersion in mineral oil, 358 mg, 8.95 mmol) in DMF (50 mL). tert-Butyl bromoacetate (2.4 mL, 14.9 mmol) was then added and the resulting mixture was stirred at 40° C. under N$_2$ overnight. The reaction was quenched with water (50 mL) and the mixture was extracted with EtOAc (250 mL). The organic layer was washed with saturated brine, dried (Na$_2$SO$_4$), and concentrated in vacuo. Chromatography (silica gel, 20% EtOAc/hexanes) afforded 3 (1.64 g, 64% yield, 98% ee by Chiracel HPLC: retention time 42.2 min for the (1R)-enantiomer and 30.6 min for the (1S)-enantiomer) as a colorless oil: $^1$H NMR (CDCl$_3$, 300 MHz) 7.22-6.71 (m, 9H), 4.58 (t, 1H), 4.44 (s, 2H), 2.68-2.59 (m, 2H), 2.05-1.93 (m, 2H), 1.41 (s, 9H); $^{13}$C NMR (CDCl$_3$, 75 MHz) 168.4, 158.6, 146.8, 142.1, 130.0, 128.8, 128.7, 126.2, 119.5, 114.1, 112.6, 82.7, 74.1, 66.1, 40.8, 32.4, 28.4. HRMS (FAB): (M+Na)$^+$ calcd 365.1729. found 365.1721.

3,4-Dimethoxy-3'-hydroxy chalcone (4)

A solution of 3,4-Dimethoxybenzaldehyde (16.6 g, 100 mmol) in EtOH (75 mL) was treated with 3-Hydroxyacetophenone (13.6 g, 100 mmol) and the resulting solution cooled to 0° C. in an ice bath. A 200 mL solution of aqueous KOH (28 g, 500 mmol) was added slowly and the resulting bright red solution was allowed to stir overnight (16 h) at room temperature. The mixture was then acidified to pH 5 by the dropwise addition of concentrated HCl and the resulting suspension extracted with EtOAc (2×200 mL). The combined organic extract was washed with a saturated NaCl solution (2×100 mL), dried over MgSO$_4$, filtered, evaporated, and flash chromatographed (silica gel, 30% Æ 50% EtOAc/hexanes) to give crude material. The crude solid was crystallized from EtOAc to afford 13.9 g (49%) of a yellow colored solids: IR (neat) 3420, 1650, 1575, 1510, 1265, 1140 cm$^{-1}$; $^1$H NMR (CDCl$_3$, 300 MHz) 7.80 (d, J=15.6 Hz, 1H), 7.68 (s, 1H), 7.59, (d, J=7.7 Hz, 1H), 7.42-7.36 (m, 2H), 7.24 (dd, J=8.3, 1.8 Hz, 1H), 7.16-7.13 (m, 2H), 6.90 (d, J=8.3 Hz, 1H), 6.82 (s, 1H), 3.95 (s, 3H), 3.94 (s, 3H); $^{13}$C NMR (CDCl$_3$, 75 MHz) 191.3, 157.0, 152.0, 149.7, 146.1, 140.1, 130.2, 128.2, 123.8, 121.2, 120.7, 120.3, 115.7, 111.6, 110.7, 56.4.

3,4,5-Trimethoxy-3'-hydroxy chalcone (5)

Prepared in a similar manner as (4) from 3,4,5-trimethoxybenzaldehyde. Flash chromatography (silica gel, 30% Æ 50% EtOAc/hexanes) afforded 2.61 g (17%) of yellow colored solids: $^1$H NMR (CDCl$_3$, 300 MHz) 9.80 (s, 1H), 7.82 (d, J=15.6 Hz, 1H), 7.70-7.63 (m, 2H), 7.48 (s, 1H), 7.39 (app t, J=7.9 Hz, 1H) 7.23 (s, 2H) 7.08 (d, J=7.6 Hz, 1H), 3.87 (s, 6H), 3.73 (s, 3H); $^{13}$C NMR (CDCl$_3$, 75 MHz) 189.5, 158.1, 153.5, 144.7, 140.1, 139.5, 130.6, 130.1, 121.8, 120.5, 119.9, 115.0, 106.9, 60.5, 56.5.

3'-Hydroxy-3,4-methylenedioxy chalcone (6)

Prepared in a similar manner as (4) from piperonal. Crude solids (26.7 g, 100%) were carried on directly to the next reaction step without chromatographic purification or characterization.

3-(3,4-Dimethoxyphenyl)-1-(3-hydroxyphenyl)propan-1-one (7)

A solution of 3,4-Dimethoxy-3'-hydroxy chalcone (4) (10 g, 352 mmol) in a 1:1 mixture of EtOAc:Acetone (40 mL) was treated with 10% Pd on Carbon (500 mg) and the mixture hydrogenated at 40-50 psi pressure of H$_2$ for 3 h. The reaction mixture was filtered through a pad of Celite with the aid of acetone and the filtrate concentrated to afford a crude solid.

The crude solid was triturated with EtOAc and filtered to afford 7.83 g (78%) of white solids which proved to be of ~90% purity by $^1$H NMR analysis: $^1$H NMR (CDCl$_3$, 300 MHz) 7.56 (s, 1H), 7.55, (d, J=2.2 Hz, 1H), 753-733 (m, 1H), 7.10 (dd, J=7.9, 2.4 Hz, 1H), 6.80-7.79 (m, 3H), 6.61 (s, 1H), 3.86 (s, 3H), 3.86 (s, 3H), 3.28 (t, J=7.9 Hz, 2H), 3.02 (t, J=7.9 Hz, 2H); $^{13}$C NMR (CDCl$_3$, 75 MHz) 200.6, 156.9, 149.3, 147.8, 138.6, 134.2, 130.3, 121.1, 120.6, 115.0, 112.4, 111.8, 56.3, 41.2, 30.3.

1-(3-Hydroxyphenyl)-3-(3,4,5-trimethoxyphenyl) propan-1-one (8)

Prepared in a similar manner as (7) from 3,4,5-Trimethoxy-3'-hydroxy chalcone (5). Flash chromatography (silica gel, 40% Æ 50% EtOAc/hexanes) of crude material afforded 1.37 g (68%) of white solids: IR (neat) 3395, 2940, 1680, 1590, 1505, 1455, 1240, 1125 cm$^{-1}$; $^1$H NMR (CDCl$_3$, 300 MHz) 7.54-7.52 (m, 2H), 7.34 (app t, J=8.1 Hz, 1H), 7.10 (dd, J=7.9, 2.2 Hz, 1H), 6.48 (s, 2H), 6.08 (s, 1H), 3.85 (s, 9H), 3.30 (t, J=7.3 Hz, 2H), 3.02 (t, J=7.7 Hz, 2H); $^{13}$C NMR (CDCl$_3$, 75 MHz) 200.0, 156.7, 153.6, 138.7, 137.4, 136.7, 130.3, 120.9, 115.0, 105.8, 61.3, 56.5, 41.0, 31.0.

1-(3-Hydroxyphenyl)-3-(3,4-methylenedioxyphenyl) propan-1-one (9)

Prepared in a similar manner as (7) from 3'-Hydroxy-3,4-methylenedioxy chalcone (6). Crystallization of crude material from EtOAc/hexanes afforded 4.10 g (41%) of white solids: $^1$H NMR (CDCl$_3$, 300 MHz) 9.73 (s, 1H), 7.43 (d, J=7.8 Hz, 1H), 734-7.29 (m, 2H), 7.02 (dd, J=8.0 Hz, 1H), 6.88 (m, 1H), 6.80 (d, J=7.9 Hz, 1H), 6.71 (d, J=7.9 Hz, 1H), 5.96 (s, 2H), 3.26 (t, J=7.6 Hz, 2H), 2.84 (t, J=75 Hz, 2H); $^{13}$C NMR (CDCl$_3$, 75 MHz) 199.4, 158.0, 147.5, 145.7, 138.4, 135.4, 130.1, 121.5, 120.5, 1193, 114.4, 1092, 108.4, 101.0, 402, 29.7.

1-(3-(tert-Butoxycarbonylmethoxy)phenyl)-3-(3,4-dimethoxyphenyl)propan-1-one (10)

A 60% mineral oil suspension of NaH (279 mg, 6.98 mmol) in anhydrous DMF (10 mL) was cooled to 0° C. in an ice bath and solid 3-(3,4-Dimethoxyphenyl)-1-(3-hydroxyphenyl)propan-1-one (7) (2 g, 6.98 mmol) added in one portion. The resulting yellow solution was stirred for 5 min after which time tert-butylbromoacetate (1.18 mL, 7.33 mmol) was added. Stirring was continued at 0° C. for 15 min after which time the reaction mixture was warmed to room temperature and partitioned between diethyl ether (50 mL) and water (50 mL). The organic layer was washed with a saturated NaCl solution (2×50 mL), dried over MgSO$_4$, filtered, evaporated, and flash chromatographed (silica gel, 30% EtOAc/hexanes) to afford 230 g (82%) of a clear colorless oil: IR (neat) 2980, 1750, 1685, 1590, 1515, 1260, 1155 cm$^{-1}$; $^1$H NMR (CDCl$_3$, 300 MHz) 7.59 (d, J=7.7 Hz, 1H), 7.49 (s, 1H), 7.39 (app t, J=8.0 Hz, 1H), 7.14 (dd, J=8.2, 2.6 Hz, 1H), 6.81-6.79 (m, 3H), 4.58 (s, 2H), 3.89 (s, 3H), 3.88 (s, 3H), 3.28 (t, J=7.3 Hz, 2H), 3.02 (t, J=7.8 Hz, 2H), 1.51 (s, 9H); $^{13}$C NMR (CDCl$_3$, 75 MHz) 199.2, 168.0, 158.6, 149.3, 147.8, 138.7, 134.2, 130.1, 121.8, 120.6, 113.5, 112.2, 111.8, 108.1, 83.0, 66.1, 56.2, 41.1, 30.2, 28.4.

1-(3-(tert-Butoxycarbonylmethoxy)phenyl)-3-(3,4,5-trimethoxyphenyl)propan-1-one (11)

Prepared in a similar manner as (10) from 1-(3-Hydroxyphenyl)-3-(3,4,5-trimethoxyphenyl)propan-1-one (8). Flash chromatography (silica gel, 30% Æ 40% EtOAc/hexanes) of crude material afforded 1.30 g (96%) of a clear colorless oil: IR (neat) 2955, 1750, 1684, 1590, 1455, 1230, 1150, 1125 cm$^{-1}$; $^1$H NMR (CDCl$_3$, 300 MHz) 7.59 (d, J=7.7 Hz, 1H), 7.49 (s, 1H), 7.39 (app t, J=7.9 Hz, 1H), 7.14 (dd, J=8.2, 2.6 Hz, 1H), 6.47 (s, 2H), 4.58 (s, 2H), 3.86 (s, 6H), 3.84 (s, 3H), 3.28 (t, J=7.3 Hz, 2H), 3.01 (t, J=7.8 Hz, 2H), 1.50 (s, 9H); $^{13}$C NMR (CDCl$_3$, 75 MHz) 199.1, 168.0, 158.5, 153.6, 138.6, 137.4, 136.8, 130.1, 121.8, 120.4, 113.6, 105.8, 83.0, 66.1, 61.2, 56.5, 41.0, 31.0, 28.4.

1-(3-(tert-Butoxycarbonylmethoxy)phenyl)-3-(3,4-methylenedioxyphenyl)propan-1-one (12)

Prepared in a similar manner as (10) from 1-(3-Hydroxyphenyl)-3-(3,4-methylenedioxyphenyl)propan-1-one (9). Flash chromatography (silica gel, 20% Æ 30% EtOAc/hexanes) of crude material afforded 5.04 g (89%) of a clear colorless oil: IR (neat) 2980, 1750, 1685, 1490, 1445, 1245, 1155, 1040 cm$^{-1}$; $^1$H NMR (CDCl$_3$, 300 MHz) 7.58 (dd, J=6.7, 1.1 Hz, 1H), 7.48 (s, 1H), 7.39 (app t, J=8.0 Hz, 1H), 7.17-7.13 (m, 1H), 6.89-6.69 (m, 4H), 5.94 (s, 2H), 458 (s, 2H), 3.25 (t, J=7.8 Hz, 2H), 2.99 (t, J=7.8 Hz, 2H), 1.51 (s, 9H); $^{13}$C NMR (CDCl$_3$, 75 MHz) 199.0, 168.0, 158.5, 148.1, 146.3, 138.6, 135.4, 130.1, 121.8, 121.5, 120.6, 113.4, 109.3, 108.7, 101.2, 83.0, 66.1, 41.1, 20.3, 28.4.

(R) 1-(3-(tert-Butoxycarbonylmethoxy)phenyl)-3-(3,4-dimethoxyphenyl)propan-1-ol (13)

A solution of 1-(3-(tert-Butoxycarbonylmethoxy)phenyl)-3-(3,4-dimethoxyphenyl)propan-1-one (10) (3.0 g, 7.49 mmol) in THF (5 mL) at −20° C. was treated with a solution of (+)-B-chlorodiisopinocamphenylborane (2.9 g, 8.99 mmol) in THF (10 mL) at −20° C. The resulting mixture was allowed to stand in a −20° C. freezer for 48 h after which time the mixture was evaporated and treated with diethyl ether (25 mL) followed by diethanolamine (8 mL). The viscous mixture was allowed to stir at room temperature for 3 h, after which time, was filtered through a pad of Celite with the aid of diethyl ether. The cloudy filtrate was evaporated and flash chromatographed (silica gel, 30% Æ 40% EtOAc/hexanes) to afford 2.72 g (90%) of a clear colorless oil. (95% ee by Chiracel HPLC, 25% i-PrOH/hexanes, retention time 44.4 min for the R-enantiomer and 35.7 mm for the S-enantiomer): IR (neat) 3525, 2935, 1750, 1515, 1150 cm$^{-1}$; $^1$H NMR (CDCl$_3$, 300 MHz) 7.30-7.25 (m, 2H), 6.99-6.73 (m, 5H), 4.68 (m, 1H), 453 (s, 2H), 3.88 (s, 3H), 3.87 (s, 3H), 2.72-2.63 (m, 2H), 2.12-1.97 (m, 2H), 1.50 (s, 9H); $^{13}$C NMR (CDCl$_3$, 75 MHz) 168.4, 158.5, 149.3, 147.6, 146.9, 134.8, 130.0, 120.6, 119.5, 114.0, 112.6, 112.2, 111.7, 82.7, 74.1, 66.1, 56.3, 56.2, 41.0, 32.0, 28.4.

(1R)-3-(3,4,5-Trimethoxyphenyl)-1-(3-(tert-butoxycarbonylmethoxy)phenyl)-propan-1-ol (14)

To a solution of 11 (130 g, 3.0 mmol) in THF (5 mL) at −23° C. under N$_2$ was added a cold (−23° C.) solution of (+)-B-chlorodiisopincampheylborane (1.64 g, 5.1 mmol) in THF (10 mL). The mixture was placed in a freezer for 3 days. Then, the mixture was concentrated in vacuo and the residue was redissolved in diethyl ether (60 mL). The ether solution was treated with diethanolamine (0.86 mL, 9.0 mmol) with vigorous stirring at room temperature for 3 h. The white precipitates were filtered off and the filtrate was concentrated in vacuo. Chromatography on silica (50-100% EtOAc/hexanes) provided 1.3 g (99%) of a colorless oil (98.1% ee by Chiracel HPLC, 20% i-PrOH/hexanes, retention time 46.4 min for the R-enantiomer and 40.0 min for the S-enantiomer). $^1$H NMR (CDCl$_3$, 300 MHz) 7.28 (t, J=7.8 Hz, 1H), 6.96 (m, 2H), 6.82 (m, 1H), 6.41 (s, 2H), 4.69 (t, J=6.2 Hz, 1H), 4.52 (s, 2H), 3.85 (s, 6H), 3.83 (s, 3H), 2.65 (m, 2H), 2.05 (m, 2H), 1.50 (s, 9H); $^{13}$C NMR (CDCl$_3$, 75 MHz) 168.4, 158.6, 1535, 146.8, 137.9, 136.6, 130.0, 119.5, 114.0, 112.7, 105.7, 82.8, 74.1, 66.0, 61.2, 56.5, 40.8, 32.8, 28.4.

(R) 1-(3-(tert-Butoxycarbonylmethoxy)phenyl)-3-(3, 4-methylenedioxyphenyl)propan-1-ol (15)

Prepared in a similar manner as (13) from 1-(3-(tert-Butoxycarbonylmethoxy)phenyl)-3-(3,4-methylenedioxyphenyl)propan-1-one (12). Flash chromatography (silica gel, 20% Æ 25% EtOAc/hexanes) of crude material afforded 3.84 g (96%) of a clear colorless oil: IR (neat) 3440, 1750, 1490, 1440, 1245, 1150, 1040 cm$^{-1}$; $^1$H NMR (CDCl$_3$, 300 MHz) 7.30-7.24 (m, 1H), 6.98-6.93 (m, 2H), 6.82 (dd, J=8.2, 2.5 Hz, 1H), 6.75-6.64 (m, 3H), 5.93 (s, 2H), 4.67-4.63 (m, 1H), 4.53 (s, 2H), 2.68-2.60 (m, 2H), 2.10-1.95 (m, 3H), 1.51 (s, 9H); $^{13}$C NMR (CDCl$_3$, 75 MHz) 168.4, 158.5, 148.0, 146.9, 146.0, 136.0, 130.0, 121.5, 119.5, 114.1, 112.5, 1093, 108.5, 101.1, 82.7, 73.9, 66.1, 41.1, 32.1, 28.4.

3'-(tert-Butoxycarbonylmethoxy)acetophenone (16)

To a suspension of NaH (60% dispersion in mineral oil, 1.47 g, 36.7 mmol) in anhydrous DMF (50 mL) at 0° C. was added solid 3'-hydroxyacetophenone (5.0 g, 36.7 mmol). The mixture was stirred under N$_2$ for 10 min and a clear yellow solution was formed. Then, tert-butylbromoacetate (6.23 mL, 38.5 mmol) was added and the mixture stirred at 0° C. for 5 min and then at room temperature for 20 min. TLC showed no starting material remaining. The mixture was partitioned between EtOAc (250 mL) and water (100 mL). The organic layer was separated, washed with saturated brine, dried (MgSO$_4$) and concentrated in vacuo. Chromatography on silica (20% EtOAc/hexanes) gave 7.6 g (83%) of a white crystal. $^1$H NMR (CDCl$_3$, 300 MHz) 7.60-7.14 (m, 4H), 4.59 (s, 2H), 2.60 (s, 3H), 1.51 (s, 9H); $^{13}$C NMR (CDCl$_3$, 75 MHz) 198.0, 168.0, 158.6, 138.9, 130.1, 122.3, 120.6, 113.5, 83.0, 66.1, 28.4, 27.0.

3-(3-Pyridyl)-1-(3-(tert-butoxycarbonylmethoxy) phenyl)-2-propen-1-one (17)

A mixture of 16 (4.0 g, 16 mmol), nicotinaldehyde (1.89 mL, 20 mmol), and piperidine (4.0 mL, 40 mmol) in absolute EtOH (65 mL) was heated at reflux for 16 h. The mixture was cooled and concentrated in vacuo. Chromatography on silica gel (30-60% EtOAc/hexanes) gave a mixture of unreacted nicotinaldehyde and 17 (both have the same R$_f$ on TLC). Washing of the mixture with hexane in a filter funnel provide 1.73 g (32%) of pure 17 as a yellow crystal. $^1$H NMR (CDCl$_3$, 300 MHz) 8.87 (d, J=2.1 Hz, 1H), 8.66 (dd, J=4.8, 1.5 Hz, 1H), 7.97 (d, J=7.9 Hz, 1H), 7.80 (d, J=16.7 Hz, 1H), 7.66 (d, J=7.6 Hz, 1H), 7.60 (d, J=15.9 Hz, 1H), 7.55 (s, 1H), 7.46 (t, J=7.8 Hz, 1H), 7.38 (dd, J=7.9, 4.8 Hz, 1H), 7.20 (dd, J=8.2, 2.6 Hz, 1H), 4.62 (s, 2H), 1.52 (s, 9H); $^{13}$C NMR (CDCl$_3$, 75 MHz) 189.7, 175.0, 168.0, 158.7, 151.6, 150.5, 141.4, 139.5, 134.9, 131.0, 130.2, 124.2, 122.3, 120.6, 114.1, 83.1, 66.2, 28.4.

1-(3-(tert-Butoxycarbonylmethoxy)phenyl)-3-(3-indoyl)-2-propen-1-one (18)

A mixture of 16 (2.0 g, 8.0 mmol) and 3-indolecarboxaldehyde (967 mg, 6.66 mmol) in piperidine (4 mL) was heated at reflux for 6 h. The reaction mixture was cooled and treated with pH 7 phosphate buffer (25 mL) and EtOAc (50 mL). The organic portion was washed with a saturated NaHCO$_3$ solution (2×50 mL) followed by a saturated NaCl solution (2×25 mL) solution. The organic layer was then dried over MgSO$_4$, filtered, evaporated, and flash chromatographed (silica gel, 50% EtOAc/hexanes) to afford 1.47 g (59%) of yellow solids. IR (neat) 1730, 1650, 1560, 1240, 1150 cm$^{-1}$; $^1$H NMR (MeOH, 300 MHz) 8.06 (d, J=15.5 Hz, 1H), 7.94-7.91 (m, 1H), 7.76 (s, 1H), 7.62 (dd, J=6.7, 1.1 Hz, 1H), 7.52-7.42 (m, 4H), 7.40-7.17 (m, 3H), 4.61 (s, 2H), 1.42 (s, 9H); $^{13}$C NMR (MeOH, 75 MHz) 192.9, 170.5, 160.2, 142.4, 142.1, 139.8, 134.2, 131.3, 127.2, 124.5, 123.0, 121.7, 120.7, 117.4, 115.3, 113.7, 84.0, 67.2, 28.7.

3-(3-Pyridyl)-1-(3-(tert-butoxycarbonylmethoxy) phenyl)-propan-1-one (19)

A mixture of 17 (1.70 g, 5.0 mmol) and 10% Pd/C (85 mg) in EtOAc (70 mL) was hydrogenated in a Parr under H$_2$ at 42 psi for 15 h. The mixture was filtered through Celite and the filtrate was concentrated in vacuo. Chromatography on silica (50-60% EtOAc/hexanes) gave 1.70 g (100%) of a colorless oil. $^1$H NMR (CDCl$_3$, 300 MHz) 8.54 (d, J=2.0 Hz, 1H), 8.48 (dd, J=4.8, 1.5 Hz, 1H), 7.70-7.10 (m, 6H) 4.58 (s, 2H), 3.31 (t, J=7.3 Hz, 2 H), 3.09 (t, J=7.4 Hz, 2H), 1.50 (s, 9H); $^{13}$C NMR (CDCl$_3$, 75 MHz) 198.3, 168.0, 158.6, 150.4, 148.1, 138.4, 136.9, 136.4, 130.2, 123.7, 121.8, 120.7, 113.5, 83.0, 66.1, 40.2, 28.4, 27.5.

1-(3-(tert-Butoxycarbonylmethoxy)phenyl)-3-(3-indoyl)propan-1-one (20)

Prepared in a similar manner as (19) from 1-(3-(tert-Butoxycarbonylmethoxy)phenyl)-3-(3-indoyl)-2-propen-1-one (18). Flash chromatography (silica gel, 20% Æ 30% EtOAc/hexanes) afforded 468 mg (80%) of a white solid: IR (neat) 1735, 1680, 1230, 1150 cm$^{-1}$; $^1$H NMR (MeOH, 300 MHz) 7.60-7.55 (m, 2H), 7.43-7.32 (m, 3H), 7.16-6.99 (m, 4H), 4.57 (s, 2H), 3.39-332 (obs t, 2H), 3.16 (t, J=7.2 Hz, 2H), 1.47 (s, 9H); $^{13}$C NMR (MeOH, 75 MHz) 202.5, 170.4, 160.0, 140.2, 138.6, 131.3, 129.0, 123.5, 122.9, 122.7, 121.5, 120.0, 119.7, 115.6, 114.6, 112.6, 84.0, 67.1, 41.0, 28.7, 21.6.

(1R)-3-(3-Pyridyl)-1-(3-(tert-butoxycarbonylmethoxy)phenyl)-propan-1-ol (21)

To a solution of 19 (1.70 g, 4.98 mmol) in THF (10 mL) at −23° C. under N$_2$ was added a cold (−23° C.) solution of (+)-B-chlorodiisopinocamphenylborane (3.2 g, 9.97 mmol) in THF (20 mL). The mixture was placed in a freezer for 3 days. Then, the mixture was concentrated in vacuo and the residue was redissolved in diethyl ether (100 mL). The ether solution was treated with diethanolamine (1.44 mL, 15.0 mmol) with vigorous stirring at room temperature for 3 h. The white precipitates were filtered off and the filtrate was concentrated in vacuo. Chromatography on silica (50-100% EtOAc/hexanes) provided 1.41 g (82%) of a colorless oil (975% ee by Chiracel HPLC, 25% i-PrOH/hexanes, retention time 78.5 min for the R-enantiomer and 52.1 min for the S-enantiomer). $^1$H NMR (CDCl$_3$, 300 MHz) 8.42 (m, 2H), 7.55-6.80 (m, 6H), 4.65 (dd, J=7.8, 5.1 Hz, 1H), 4.52 (s, 2H), 2.75 (m, 2 H), 2.05 (m, 2H), 1.49 (s, 9H); $^{13}$C NMR (CDCl$_3$, 75 MHz) 175.1, 168.4, 158.6, 150.3, 147.7, 146.8, 137.5, 136.3, 130.0, 123.7, 119.4, 114.1, 112.5, 108.0, 82.8, 73.5, 66.0, 40.5, 295, 28.4.

(R) 1-(3-(tert-Butoxycarbonylmethoxy)phenyl)-3-(3-indoyl)propan-1-ol (22)

Prepared in a similar manner as (21) from 1-(3-(tert-Butoxycarbonylmethoxy)phenyl)-3-(3-indoyl)propan-1-one (20). Flash chromatography (silica gel, 20% Æ 30% EtOAc/hexanes) afforded 258 mg (55%) of yellowish oil (+95% ee by Chiracel HPLC, 20% i-PrOH/hexanes, retention time 54.2 min for the R-enantiomer and 50.7 min for the S-enantiomer): IR (neat) 3410, 2930, 1735, 1455, 1230, 1150, 1080 cm$^{-1}$; $^1$H NMR (MeOH, 300 MHz) 7.51 (d, J=7.8 Hz, 1H), 7.33 (d, J=8.1, 1H), 7.25 (app t, J=7.9, 1H), 7.11-6.92 (m, 5H), 6.82-6.78 (m, 1H), 4.67 (t, J=5.8 Hz, 1H), 4.54 (s, 2H), 2.85-2.77 (m, 2H), 2.18-2.06 (m, 2H), 1.47 (s, 9H); $^{13}$C NMR (MeOH, 75 MHz) 170.8, 159.9, 148.9, 138.6, 130.8, 129.2, 123.2, 122.6, 120.8, 119.9, 116.4, 114.9, 113.7, 112.6, 83.8, 75.0, 67.0, 41.3, 28.7, 22.9.

Preparation of Functionalized Monomers

(1R)-3-Phenyl-1-[3-((3-aminopropyl)oxy)phenyl]-1-propyl (2S)-1-(3,3-dimethyl-1,2-dioxopentyl)-2-piperidinecarboxylate trifluoroacetic acid salt (24)

A solution of alcohol 2 (385 mg, 1.0 mmol) in CH$_2$Cl$_2$ (3 mL) was treated with (2S)-1-(1,2-dioxo-3,3-dimethylpentyl)-2-piperidinecarboxylic acid (23, 255 mg, 1.0 mmol, prepared from L-pipercolic acid in 4 steps following literature procedures by Holt et al. *J. Amer. Chem. Soc.,* 1993, 115, 9925-9938), followed by 1,3-dicyclohexylcarbodiimide (DCC, 247 mg, 1.2 mmol), and 4-(dimethylamino)-pyridine (DMAP, 85 mg, 0.70 mmol) under a nitrogen atmosphere. The resulting bright yellow suspension was allowed to stir overnight. The mixture was then filtered through glass wool and chromatographed (silica gel, 20% EtOAc/hexanes) to give (1R)-3-Phenyl-1-[3-9(3-tert-butyloxycarbamoylpropyl) oxy)phenyl]-1-propyl (2S)-1-(3,3-dimethyl-1,2-dioxopentyl)-2-piperidinecarboxylate (524 mg, 84%) as a colorless oil: $^1$H NMR (CDCl$_3$, 300 MHz) (single diastereomer, mixture of rotamers) 7.35-6.90 (m, 9H), 5.80 (t, J=5.9 Hz, 1H), 5.32 (d, J=5.0 Hz, 0.82 H, pipercolate a-H of rotamer A), 4.80 (br. s, 1H), 4.02 (t, J=6.1 Hz, 2H), 3.40-3.25 (m, 3H), 3.12 (td, J=13.0, 3.3 Hz, 1H), 2.60 (m, 2H), 2.35 (d, J=14 Hz, 1H), 2.28 (m, 1H), 2.07 (m, 1H), 1.96 (t, J=6.3 Hz, 2H), 1.80-1.60 (m, 5H), 1.43 (s, 9H), 1.22 (s, 3H), 1.20 (s, 3H), 0.88 (t, J=7.4 Hz, 3H); $^{13}$C NMR (CDCl$_3$, 75 MHz) (single diastereomer, mixture of rotamers) 208.2, 170.1, 167.6, 159.4, 156.4, 141.7, 141.3, 130.1, 128.9, 128.7, 1265, 119.4, 114.7, 113.2, 113.0, 66.1, 57.1, 51.7, 47.1, 44.5, 38.3, 32.9, 32.1, 30.0, 28.8, 26.8, 25.4, 24.9, 24.0, 23.8, 23.5, 21.6, 9.1. MS(FAB): (M+Na)$^+$ 645, (M+H)$^+$ 623.

A solution of the above compound (200 mg, 032 mmol) in CH$_2$Cl$_2$ (5.0 mL) was treated with trifluoroacetic add (1.0 mL) and the mixture was stirred at room temperature for 1 h. The reaction mixture was diluted with toluene (150 mL) and concentrated in vacuo to give 24 (203 mg, 100%) as a colorless gum: $^1$H NMR (CDCl$_3$, 300 MHz) (single diastereomer, mixture of rotamers) 7.90 (br. s, 3H), 7.30-6.70 (m, 9H), 5.70 (t, J=5.4 Hz, 1H), 5.23 (d, J=4.8 Hz, 1H), 4.01 (m, 2H), 3.30 (d, J=12.8 Hz, 1H), 3.13 (m, 3H), 258 (m, 2H), 2.40-2.00 (m, 4 H), 1.75-1.50 (m, 5H), 1.35 (m, 2H), 1.13 (s, 3H), 1.12 (s, 3H), 0.80 (t, J=7.4 Hz, 3H); $^{13}$C NMR (CDCl$_3$, 75 MHz) (single diastereomer, mixture of rotamers) 208.4, 175.3, 175.2, 170.1, 167.8, 158.8, 142.0, 141.2, 130.2, 128.9, 128.7, 1265, 119.8, 114.6, 113.0, 108.0, 66.1, 51.8, 47.1, 44.6, 38.6, 38.3, 32.8, 32.1, 27.3, 26.8, 25.3, 23.8, 23.4, 21.5, 9.0. HRMS (FAB): (M+Na)$^+$ calcd: 523.3172 found: 523.3162.

(1R)-3-Phenyl-1-(3-(hydroxycarbonylmethoxy)phenyl)-1-propyl (2S)-1-(3,3-dimethyl-1,2-dioxopentyl)-2-piperidinecarboxylate (25)

A solution of alcohol 3 (342 mg, 1.0 mmol) in CH$_2$Cl$_2$ (3 mL) was treated with (2S)-1-(1,2-dioxo-3,3-dimethylpentyl)-2-piperidinecarboxylic acid (23, 255 mg, 1.0 mmol, prepared from L-pipecolic acid in 4 steps following literature procedures by Holt et al. *J. Amer. Chem. Soc.,* 1993, 115, 9925-9938), followed by 1,3-dicyclohexylcarbodiimide (DCC, 247 mg, 1.2 mmol), and 4-(dimethylamino)-pyridine (DMAP, 85 mg, 0.70 mmol) under a nitrogen atmosphere. The resulting bright yellow suspension was allowed to stir overnight. The mixture was then filtered through glass wool and chromatographed (silica gel, 20% EtOAc/hexanes) to give (1R)-3-Phenyl-1-(3-(tert-butoxycarbonylmethoxy)phenyl]-1-propyl (2S)-1-(3,3-dimethyl-1,2-dioxopentyl)-2-piperidinecarboxylate (470 mg, 82%) as a colorless oil: $^1$H NMR (CDCl$_3$, 300 MHz) (single diastereomer, mixture of rotamers) 7.50-6.90 (m, 9H), 5.93 (t, J=6.0 Hz, 1H), 5.46 (d, J=3.4 Hz, 0.83 H, pipercolate a-H of rotamer A), 4.67 (s, 2H), 3.50 (d, J=12.9 Hz, 1H), 3.32 (td, J=12.5, 3.0 Hz, 1H), 2.75 (m, 2H), 2.53 (d, J=13.6 Hz, 1H), 2.41 (m, 1H), 2.22 (m, 1H), 2.97-2.71 (m, 6H), 1.62 (s, 9H), 138 (s, 3H), 1.35 (s, 3H), 1.03 (t, J=7.4 Hz); $^{13}$C NMR (CDCl$_3$, 75 MHz) (single diastereomer, mixture of rotamers) 208.3, 175.0, 170.0, 168.0, 167.5, 158.5, 141.7, 141.2, 130.2, 128.9, 128.7, 126.5, 120.2, 114.7, 113.6, 82.8, 66.1, 51.6, 47.1, 44.5, 38.2, 32.9, 32.0, 28.4, 26.8, 25.3, 24.0, 23.4, 21.6, 9.2. HRMS(FAB): (M+Na)$^+$ calcd: 602.3094. found: 602.3090.

A solution of the above tert-butyl ester (200 mg, 0.34 mmol) in CH$_2$Cl$_2$ (5.0 mL) was treated with trifluoroacetic acid (1.0 mL) and the mixture was stirred at room temperature for 1 h. The reaction mixture was diluted with toluene (150 mL) and concentrated in vacuo to give 25 (177 mg, 99%) as a colorless gum: $^1$H NMR (CDCl$_3$, 300 MHz) (single diastereomer, mixture of rotamers) 730-6.80 (m, 9H), 5.75 (m, 1H), 530 (d, J=4.8 Hz, 1H), 4.66 (s, 2H), 3.35 (d, J=9.27 Hz, 1H), 3.19 (td, J=12.4, 2.9 Hz, 1H), 2.69 (m, 2H), 239 (d, J=16.2 Hz, 1H), 2.30 (m, 1H), 2.10 (m, 1H), 1.90-1.60 (m, 6H), 1.50 (m, 1H), 1.19 (s, 3H), 1.17 (s, 3H), 0.85 (t, J=7.4 Hz, 3H); $^{13}$C NMR (CDCl$_3$, 75 MHz) (single diastereomer, mixture of rotamers) 208.0, 172.3, 169.8, 167.9, 158.2, 142.2, 141.1, 130.2, 128.9, 128.7, 126.5, 120.3, 115.5, 111.8, 65.5, 57.2, 52.0, 47.2, 44.6, 38.3, 33.0, 32.9, 32.1, 27.0, 25.3, 25.2, 23.9, 23.4, 21.5, 9.1. HRMS(FAB): (M+Na)$^+$ calcd: 546.2468. found: 546.2461.

(1R)-3-(3,4-Dimethoxyphenyl)-1-[3-(hydroxycarbonylmethoxy)phenyl]-1-propyl (2S)-1-(3,3-dimethyl-1,2-dioxopentyl)-2-piperidinecarboxylate (26)

A solution of (R) 1-(3-(tert-Butoxycarbonylmethoxy)phenyl)-3-(3,4-dimethoxyphenyl)propan-1-ol (13) (805 mg, 2.0 mmol) in CH$_2$Cl$_2$ (4 mL) at 0° C. was treated with (2S)-1-(1,2-dioxo-3,3-dimethylpentyl)-2-piperidinecarboxylic acid (23, 511 mg, 2.0 mmol, prepared from L-pipecolic acid in 4 steps following literature procedures by Holt et al. *J. Amer. Chem. Soc.,* 1993, 115, 9925-9938) followed by 4-(dimethylamino)pyridine (DMAP 1 mg) and 1,3-dicyclohexyl carbodiimide (DCC, 413 mg, 2 mmol) under a nitrogen atmosphere. The resulting bright yellow suspension was allowed to stir for 2 h then diluted with diethyl ether (20 mL). The reaction mixture was then filtered, evaporated, and flash chromatographed (silica gel, 25% Æ 30% EtOAc/hexanes) to afford 993 mg (78%) of a clear colorless viscous oil: IR (neat) 2940, 1735, 1645, 1515, 1455, 1225, 1150 cm$^{-1}$; $^1$H NMR (CDCl$_3$, 300 MHz) 7.20-7.17 (m, 2H), 6.91-6.69 (m, 5H), 5.73-5.68 (m, 1H). 5.24 (br s, 1H), 4.46 (s, 2H), 3.79 (s, 3H), 3.78 (s, 3H), 3.29 (br d, J=13.2 Hz, 1H), 3.07 (td, J=12.7, 3.0 Hz, 1H), 2.52-2.44 (m, 2H), 2.29 (br d, J=13.6 Hz, 1H), 2.20-2.13 (m, 1H), 2.04-1.95 (m, 1H), 1.71-1.51 (m, 7H), 1.41 (s, 9H), 1.16, (s, 3H), 1.14 (s, 3H), 0.82 (t, J=7.4 Hz, 3H); $^{13}$C NMR (CDCl$_3$, 75 MHz) 208.2, 170.1, 168.3, 167.6, 158.5, 149.3, 147.8, 141.8, 133.9, 130.1, 120.5, 120.3, 114.7, 113.7, 112.2, 111.7, 82.7, 66.2, 56.2, 51.7, 47.1, 44.6, 38.3, 32.9, 31.6, 28.8, 26.8, 25.3, 23.8, 23.5, 21.6, 9.1. HRMS (FAB): (M+Na)$^+$ calcd: 662.3305. found 662.3301.

A solution of the above tert-butyl ester (460 mg, 0.72 mmol) in CH$_2$Cl$_2$ (5.0 mL) was treated with trifluoroacetic acid (1.0 mL) and the mixture was stirred at room temperature for 1 h. The reaction mixture was diluted with toluene (150 mL) and concentrated in vacuo to give 26 (420 mg, 100%) as a yellowish foam: $^1$H NMR (CDCl$_3$, 300 MHz) (single diastereomer, mixture of rotamers) 8.00 (br. s, 1H), 7.35-6.70 (m, 7H), 5.82 (m, 1H), 5.33 (d, J=4.5 Hz, 1H), 4.71 (m, 2H), 3.89 (s, 3H), 3.87 (s, 3H), 3.38 (d, J=12.6 Hz, 1H), 3.24 (td, J=12.3, 2.7 Hz, 1H), 2.60 (m, 2H), 2.45-2.05 (m, 3H), 1.70 (m, 6H), 1.45 (m, 2H), 1.23 (s, 3H), 1.21 (s, 3H), 0.89 (t, J=7.4 Hz, 3H); $^{13}$C NMR (CDCl$_3$, 75 MHz) (single diastereomer, mixture of rotamers) 208.0, 172.0, 169.8, 167.8, 158.2, 149.4, 147.8, 142.2, 133.7, 130.2, 129.4, 128.6, 125.7, 120.6, 120.3, 115.5, 112.2, 111.8, 111.7, 108.2, 65.5, 56.3, 51.9, 47.2, 44.6, 38.5, 32.9, 31.7, 28.4, 27.0, 25.3, 23.9, 23.4, 21.8, 21.5, 9.1. HRMS (FAB): (M+Na)$^+$ calcd: 606.2679. found: 606.2692.

(1R)-3-(3,4,5-Trimethoxyphenyl)-1-[3-(hydroxycarbonylmethoxy)phenyl]-1-propyl (2S)-1-(3,3-dimethyl-1,2-dioxopentyl)-2-piperidinecarboxylate (27)

A solution of alcohol 14 (650 mg, 1.5 mmol) in CH$_2$Cl$_2$ (5 mL) was treated with (2S)-1-(1,2-dioxo-3,3-dimethylpentyl)-2-piperidinecarboxylic acid (23, 382 mg, 1.5 mmol, followed by 1,3-dicyclohexylcarbodiimide (370 mg, 1.8 mmol), and 4-(dimethylamino)-pyridine (128 mg, 1.0 mmol) under a nitrogen atmosphere. The resulting bright yellow suspension was allowed to stir overnight. The mixture was then filtered through glass wool and chromatographed (silica gel, 20-30% EtOAc/hexanes) to give (1R)-3-(3,4,5-trimethoxyphenyl)-1-[3-(tert-butoxycarbonylmethoxy)phenyl]-1-propyl (2S)-1-(3,3-dimethyl-1,2-dioxopentyl)-2-piperidinecarboxylate (776 mg, 78%) as a colorless oil: $^1$H NMR (CDCl$_3$, 300 MHz) (single diastereomer, mixture of rotamers) 730-6.80 (m, 4H), 6.37 (s, 2H), 5.82 (t, J=6.1 Hz, 1H), 5.33 (d, J=5.2 Hz, 1H), 4.54 (s, 2H), 3.85 (s, 6H), 3.83 (s, 3H), 3.38 (d, J=12.6 Hz, 1H), 3.16 (td, J=12.8, 3.1 Hz, 1H), 2.60 (m, 2H), 2.45-2.05 (m, 3H), 1.70 (m, 6H), 1.50 (s, 9H), 1.45 (m, 2H), 1.25 (s, 3H), 1.23 (s, 3H), 0.90 (t, J=7.4 Hz, 3H); $^{13}$C NMR (CDCl$_3$, 75 MHz) (single diastereomer, mixture of rotamers) 208.2, 175.1, 170.1, 168.2, 167.6, 158.5, 153.6, 141.7, 137.0, 130.1, 120.9, 120.2, 114.6, 113.7, 105.7, 82.7, 66.2, 61.2, 56.5, 51.7, 47.1, 44.6, 38.2, 32.9, 32.4, 28.4, 26.8, 25.3, 23.9, 23.5, 21.6, 9.1.

A solution of the above tert-butyl ester (400 mg, 0.60 mmol) in CH$_2$Cl$_2$ (5.0 mL) was treated with trifluoroacetic acid (1.0 mL) and the mixture was stirred at room temperature for 1 h. The reaction mixture was diluted with toluene (150 mL) and concentrated in vacuo to give 27 (358 mg, 98%) as a white foam: $^1$H NMR (CDCl$_3$, 300 MHz) (single diastereomer, mixture of rotamers) 7.30-6.80 (m, 4H), 6.39 (s, 2H), 5.82 (m, 1H), 5.33 (d, J=4.6 Hz, 1H), 4.70 (m, 2H), 3.86 (s, 6H), 3.84 (s, 3H), 3.38 (d, J=12.6 Hz, 1H), 3.22 (td, J=12.8, 3.1 Hz, 1 H), 2.60 (m, 2H), 2.45-2.05 (m, 3H), 1.70 (m, 6H), 1.45 (m, 2H), 1.23 (s, 3H), 1.21 (s, 3H), 0.89 (t, J=7.4 Hz, 3H); $^{13}$C NMR (CDCl$_3$, 75 MHz) (single diastereomer, mixture of rotamers) 208.0, 175.0, 171.7, 169.8, 167.8, 158.2, 153.6, 142.1, 136.9, 130.2, 129.4, 128.6, 125.7, 120.3, 115.5, 111.8, 107.9, 105.8, 65.6, 61.2, 56.5, 52.0, 47.2, 44.6, 383, 32.9, 325, 27.0, 25.3, 23.8, 23.4, 21.5, 9.1. MS(FAB): (M+Na)$^+$ calcd: 636.2785. found: 636.2756.

(R) 1-(3-(Hydroxycarbonylmethoxy)phenyl)-3-(3,4-methylenedioxyphenyl)-1-propyl (2S)-1-(3,3'-dimethyl-1,2-dioxopentyl)-2-piperidinecarboxylate (28)

A solution of (R) 1-(3-(tert-Butoxycarbonylmethoxy)phenyl)-3-(3,4-methylenedioxyphenyl)propan-1-ol (15) (500 mg, 1.29 mmol) in CH$_2$Cl$_2$ (4 mL) at 0° C. was treated with (2S)-1-(1,2-dioxo-3,3-dimethylpentyl)-2-piperidinecarboxylic acid (23, 330 mg, 1.29 mmol, prepared from L-pipecolic acid in 4 steps following literature procedures by Holt et al. *J. Amer. Chem. Soc.,* 1993, 115, 9925-9938) followed by 4-(dimethylamino)pyridine (DMAP 1 mg) and 1,3-dicyclohexyl carbodiimide (DCC, 267 mg, 1.29 mmol) under a nitrogen atmosphere. The resulting bright yellow suspension was allowed to stir for 2 h then diluted with diethyl ether (20 mL). The reaction mixture was filtered, evaporated, and flash chromatographed. Flash chromatography (silica gel, 20% Æ 30% EtOAc/hexanes) of crude material afforded 556 mg (69%) of a clear colorless oil: IR (neat) 2970, 1745, 1700, 1640, 1490, 1440, 1245, 1150 cm$^{-1}$; $^1$H NMR (CDCl$_3$, 300 MHz) (single diastereomer, mixture of rotamers) 7.32-726 (m, 1H), 6.99-6.84 (m, 6H), 5.93 (s, 2H). 5.80-76 (m, 1H), 5.33 (d, J=4.9 Hz, 1H), 4.55 (s, 2H), 3.38 (br d, J=12.9 Hz, 1H), 3.16 (td, J=12.3, 3.1 Hz, 1H), 2.63-2.50 (m, 2H), 2.38 (br d, J=13.7 Hz, 1H), 2.26-2.16 (m, 1H), 2.09-2.04 (m, 1H), 1.81-1.57 (m, 7H), 1.51 (s, 9H), 1.26, (s, 3H), 1.23 (s, 3H), 0.91 (t, J=7.4 Hz, 3H); $^{13}$C NMR (CDCl$_3$, 75 MHz) (single diastereomer, mixture of rotamers) 208.2, 170.0, 168.3, 167.6, 158.5, 148.1, 146.2, 141.7, 135.0, 130.1, 121.5, 120.2, 114.9, 113.6, 109.2, 108.6, 101.2, 82.7, 66.2, 51.7, 47.1, 44.5, 38.3, 32.9, 31.6, 28.4, 26.8, 25.3, 23.8, 23.5, 21.6, 9.1. HRMS (FAB): (M+Na)$^+$ calcd: 646.2992. found 646.3021.

A solution of the above tert-butyl ester (625 mg, 1.00 mmol) in CH$_2$Cl$_2$ (4.0 mL) was treated with trifluoroacetic acid (1.5 mL) and the mixture was stirred at room temperature for 1 h. The reaction mixture was diluted with toluene (150 mL) and concentrated in vacuo to give 28 (483 mg, 85%) as a clear colorless oil: IR (neat) 3420, 2940, 1735, 1700, 1640, 1490, 1440, 1245, 1040 cm$^{-1}$; $^1$H NMR (CDCl$_3$, 300 MHz) (single diastereomer, mixture of rotamers) 7.12 (t, J=6.7 Hz, 1H), 6.92-6.81 (m, 3H), 6.68-6.52 (m, 3H), 5.86 (s, 2H), 5.73 (t, J=7.2 Hz, 1H), 5.33 (s, 1H), 4.40 (s, 2H), 3.34 (d, J=12.2 Hz, 1H), 3.19 (t, J=12.0 Hz, 1H), 2.54-2.46 (m, 2H), 2.34 (d, J=12.6 Hz, 1H), 224-2.00 (m, 2H), 1.73-1.32 (m, 7H), 1.18 (s, 3H), 1.16 (s, 3H), 0.84 (t, J=7.3 Hz, 3H); $^{13}$C NMR (CDCl$_3$, 75 MHz) (single diastereomer, mixture of rotamers) 208.0, 169.9, 167.79, 158.3, 148.0, 146.2, 141.9, 135.0, 130.1, 121.5, 109.1, 108.6, 107.2, 101.2, 77.0, 51.9, 47.0, 44.6, 38.6, 32.9, 31.8, 26.9, 25.3, 23.9, 23.3, 21.6, 9.1.

(1R)-3-(3-Pyridyl)-1-(3-(hydroxycarbonylmethoxy)phenyl)-1-propyl (2S)-1-(3,3-dimethyl-1,2-dioxopentyl)-2-piperidinecarboxylate (29)

A solution of alcohol 21 (530 mg, 1.54 mmol) in CH$_2$Cl$_2$ (5 mL) was treated with (2S)-1-(1,2-dioxo-3,3-dimethylpentyl)-2-piperidinecarboxylic acid (23, 393 mg, 1.54 mmol, followed by 1,3-dicyclohexylcarbodiimide (381 mg, 1.85 mmol), and 4-(dimethylamino)-pyridine (132 mg, 1.08 mmol) under a nitrogen atmosphere. The resulting bright yellow suspension was allowed to stir overnight. The mixture was then filtered through glass wool and chromatographed (silica gel, 20-60% EtOAc/hexanes) to give (1R)-3-(3-Pyridyl)-1-[3-(tert-butoxycarbonylmethoxy)phenyl]-1-propyl (2S)-1-(3,3-dimethyl-1,2-dioxopentyl)-2-piperidinecarboxylate (860 mg, 96%) as a colorless oil: $^1$H NMR (CDCl$_3$, 300 MHz) (single diastereomer, mixture of rotamers) 8.46 (m, 2H), 7.50-6.80 (m, 6H), 5.80 (t, J=6.1 Hz, 1H), 5.32 (d, J=5.0 Hz, 1H), 4.54 (s, 2H), 3.38 (d, J=12.8 Hz, 1H), 3.14 (td, J=12.6, 3.0 Hz, 1H) 2.60 (m, 2H), 2.36 (d, J=13.7 Hz, 1H), 2.25 (m, 1H), 2.10 (m, 1H), 1.75 (m, 4H), 1.49 (s, 9H), 1.45 (m, 2H), 1.24 (s, 3H), 1.22 (s, 3H), 0.90 (t, J=7.4 Hz, 3H); $^{13}$C NMR (CDCl$_3$, 75 MHz) (single diastereomer, mixture of rotamers) 208.2, 175.1, 170.0, 168.2, 167.7, 158.6, 150.2, 148.1, 141.3, 136.6, 130.2, 123.8, 120.1, 115.0, 113.6, 107.9, 82.8, 66.1, 51.7, 47.1, 44.6, 39.2, 37.8, 34.4, 33.0, 29.2, 28.4, 26.7, 25.3, 23.9, 23.5, 21.6, 21.4, 9.1.

A solution of the above tert-butyl ester (400 mg, 0.69 mmol) in CH$_2$Cl$_2$ (5.0 mL) was treated with trifluoroacetic acid (1.0 mL) and the mixture was stirred at room temperature for 1 h. The reaction mixture was diluted with toluene (150 mL) and concentrated in vacuo to give 29 (424 mg, 96%, trifluoroacetic acid salt) as a white foam: $^1$H NMR (CDCl$_3$, 300 MHz) (single diastereomer, mixture of rotamers) 8.75 (s, 1H), 8.67 (d, J=10.4 Hz, 1H), 8.23 (t, J=5.6 Hz, 1H), 7.79 (dd, J=7.9, 5.6 Hz, 1H), 7.35-6.75 (m, 4H), 5.80 (t, J=6.1 Hz, 1H), 5.25 (d, J=5.0 Hz, 1H), 4.75 (m, 2H), 3.35 (d, J=13.2 Hz, 1H), 3.14 (td, J=12.6, 3.0 Hz, 1H) 2.75 (m, 2H), 2.30 (m, 3H), 1.70 (m, 6H), 1.40 (m, 2H), 1.22 (s, 6H), 0.92 (t, J=7.4 Hz, 3H); $^{13}$C NMR (CDCl$_3$, 75 MHz) (single diastereomer, mixture of rotamers) 208.3, 172.3, 169.9, 167.8, 158.6, 145.5, 142.5, 142.0, 139.8, 139.5, 130.6, 129.4, 128.6, 120.2, 117.1, 111.8, 65.2, 51.8, 47.1, 44.8, 36.7, 32.8, 28.4, 26.6, 25.2, 23.7, 21.4, 9.1. HRMS(FAB): (M+Na)$^+$ calcd: 547.2420. found: 547.2415.

(1R)-3-(3-Indolyl)-1-(3-(hydroxycarbonylmethoxy) phenyl)-1-propyl (2S)-1-(3,3-dimethyl-1,2-dioxopentyl)-2-piperidinecarboxylate (30)

The tert-butyl ester was prepared in a similar manner as the ester of 28 from (R) 1-(3-(tert-Butoxycarbonylmethoxy)phenyl)-3-(3-indoyl)propan-1-ol (22). Flash chromatography (silica gel, 30% EtOAc/hexanes) afforded 492 mg (76%) of clear colorless oil: IR (neat) 3410, 2970, 1735, 1700, 1635, 1455, 1225, 1150 cm$^{-1}$; $^1$H NMR (CDCl$_3$, 300 MHz) 8.04 (br s, 1H), 7.53 (d, J=7.8 Hz, 1H), 7.37 (d, J=8.0 Hz, 1H), 7.30-7.11 (m, 3H), 7.01-6.84 (m, 4H), 5.91-5.86 (m, 1H), 5.35 (d, J=4.8 Hz, 1H), 4.54 (s, 2H), 3.39 (d, J=13.3 Hz, 1H), 3.18 (td, J=12.6, 3.0 Hz, 1H), 2.87-2.74 (m, 2H), 2.41-2.18 (m, 3H), 1.82-1.57 (m, 7H), 1.50 (s, 9H), 1.27 (s, 3H), 1.24 (s, 3H), 0.92 (t, J=7.4 Hz, 3H); $^{13}$C NMR (CDCl$_3$, 75 MHz) 208.3, 170.1, 168.3, 167.7, 158.5, 141.9, 136.8, 130.1, 127.7, 122.3, 121.8, 120.3, 119.6, 119.1, 115.4, 114.7, 113.7, 111.5, 82.7, 66.2, 51.7, 47.1, 44.5, 36.8, 32.9, 28.4, 26.9, 25.4, 24.0, 23.4, 21.6, 9.1. HRMS(FAB): (M+Na)$^+$ calcd: 641.3203. found: 641.3193.

A solution of the above tert-butyl ester (112 mg, 0.18 mmol) in CH$_2$Cl$_2$ (5.0 mL) was treated with trifluoroacetic acid (1.0 mL) and the mixture was stirred at room temperature for 1 h. The reaction mixture was diluted with toluene (150 mL) and concentrated in vacuo to give 30 (102 mg, 100%) as a brown foam: $^1$H NMR (CDCl$_3$, 300 MHz) (single diastereomer, mixture of rotamers) 7.90-6.70 (m, 10H), 5.85 (m, 1H), 5.35 (m, 1H), 4.62 (m, 2H), 3.40 (m, 1 H), 3.25 (m, 1H), 2.80 (m, 2H), 2.40-2.05 (m, 3H), 1.85-1.45 (m, 12H), 1.23 (s, 3H), 1.21 (s, 3 H), 0.88 (t, J=7.4 Hz, 3H); $^{13}$C NMR (CDCl$_3$, 75 MHz) (single diastereomer, mixture of rotamers) 208.0, 175.0, 169.8, 167.9, 158.2, 142.3, 130.2, 129.4, 128.6, 125.7, 122.5, 119.7, 119.1, 115.3, 111.6, 108.0, 65.5, 52.0, 47.2, 44.6, 32.9, 27.0, 25.3, 23.9, 23.4, 21.6, 9.1. HRMS(FAB): (M+Na)$^+$ calcd: 585.2577. found: 585.2561.

Preparation of Dimerizers

Example 1

N,N'-Bis[3-(3-((1R)-1-((2S)-(3,3-dimethyl-1,2-dioxopentyl)piperidine-2-carbonyloxy)-3-phenyl)propylphenoxy)propyl]1,4-phenylenediacetamide (31)

A mixture of 1,4-phenylenediacetic acid (194 mg, 1.0 mmol) and disuccinimidyl carbonate (512 mg, 2.0 mg) in anhydrous acetonitrile (5.0 mL) was treated with pyridine (243 mL, 3.0 mmol). The mixture was stirred at room temperature under nitrogen overnight. The resulting suspension was partitioned between EtOAc (70 mL) and water (50 mL). The organic layer was separated, washed with 1 M Na$_2$CO$_3$, water, 0.5 N HCl, saturated brine, dried (Na$_2$SO$_4$), and concentrated in vacuo to give disuccinimidyl 1,4-phenylenediacetate (144 mg, 37%) as a white solid. $^1$H NMR (DMSO-d$_6$, 300 MHz) 7.34 (s, 4H), 4.10 (s, 4H), 2.80 (s, 8H).

A solution of 24 (102 mg, 0.16 mmol) in CH$_2$Cl$_2$ (2.0 mL) was treated with the above activated diester (31 mg, 0.080 mmol) and Et$_3$N (67 mL, 0.48 mmol). The mixture was stirred at room temperature overnight. The resulting clear solution was impregnated on silica gel and evaporated to dryness. Chromatography (silica gel, 50-100% EtOAc/hexanes) provided 31 (60 mg, 62%) as a white solid: mp 55-57° C.; $^1$H NMR (CDCl$_3$, 300 MHz) (single diastereomer, mixture of rotamers) 7.32-7.15 (m, 16H), 6.95 (d, J=7.7 Hz, 2H), 6.83 (s, 2H), 6.74 (m, 2H), 6.01 (br. s, 2H), 5.80 (t, J=5.8 Hz, 2H), 5.32 (d, J=4.9 Hz, 2H), 3.98 (t, J=5.7 Hz, 4H), 3.52 (s, 4H), 3.50-3.30 (m, 6H), 3.22 (td, J=12.4, 2.6 Hz, 2H), 2.67 (m, 4H), 2.38 (d, J=13.6 Hz, 2H), 2.30 (m, 2H), 2.12 (m, 2H), 1.95 (t, J=6.1 Hz, 4H), 1.85-1.60 (m, 10H), 1.50 (m, 4H), 1.23 (s, 6H), 1.21 (s, 6H), 0.89 (t, J=7.4 Hz, 6H); $^{13}$C NMR (CDCl$_3$, 75 MHz) (single diastereomer, mixture of rotamers) 208.2, 208.0, 171.3, 170.1, 169.9, 167.8, 159.2, 141.8, 141.6, 141.2, 134.4, 130.3, 130.1, 128.9, 128.7, 126.5, 119.3, 115.0, 114.7, 113.1, 112.8, 57.1, 51.7, 47.1, 44.5, 43.7, 39.3, 38.3, 38.2, 37.8, 33.0, 32.8, 32.1, 29.3, 26.9, 25.3, 23.9, 23.5, 21.6, 21.4, 9.17, 9.13. MS(FAB): (M+Na)$^+$ 1225, (M+H)$^+$ 1203.

Example 2

N,N'-Bis[3-(3-((1R)-1-((2S)-(3,3-dimethyl-1,2-dioxopentyl)piperidine-2-carbonyloxo)-3-phenyl)propylphenoxy)propyl]suberamide (32)

Following the same procedure as in Example 1 except replacing suberic acid for 1,4-phenylenediacetic acid, obtained 32 (54 mg, 56%) as a white solid. mp 44-46° C.; $^1$H NMR (CDCl$_3$, 300 MHz) (single diastereomer, mixture of rotamers) 7.35-6.85 (m, 18H), 6.18 (br. s, 2 H), 5.86 (t, J=5.9 Hz, 2H), 5.39 (d, J=4.9 Hz, 2H), 4.12 (t, J=5.9 Hz, 4H), 3.60-3.40 (m, 6H), 3.28 (td, J=12.6, 2.8 Hz, 2H), 2.70 (m, 4H), 2.47 (d, J=13.8 Hz, 2H), 2.35 (m, 2H), 2.30-2.00 (m, 12H), 1.95-1.70 (m, 14H), 1.55-1.35 (m, 6H), 1.30 (s, 6H), 1.28 (s, 6H), 0.96 (t, J=7.5 Hz, 6H); $^{13}$C NMR (CDCl$_3$, 75 MHz) (single diastereomer, mixture of rotamers) 208.3, 170.0, 167.8, 159.3, 141.8, 141.2, 130.2, 128.9, 128.7, 126.5, 119.4, 114.7, 113.0, 66.4, 51.7, 47.1, 44.5, 383, 37.7, 32.8, 32.1, 29.3, 28.7, 26.9, 25.8, 25.3, 23.9, 21.6, 9.1. MS(FAB): (M+Na)$^+$ 1205.

Example 3

N,N'-Bis[3-(3-((1R)-1-((2S)-(3,3-dimethyl-1,2-dioxopentyl)piperidine-2-carbonyloxo)-3-phenyl)propylphenoxy)propyl]pyridine-2,6-dicarboxamide (33)

Following the same procedure as in Example 1 except replacing pyridine-2,6-dicarboxylic acid for 1,4-phenylenediacetic acid, obtained 33 (44 mg, 54%) as a white solid. mp 60-62° C.; $^1$H NMR (CDCl$_3$, 300 MHz) (single diastereomer, mixture of rotamers) 8.34 (d, J=7.7 Hz, 2H), 8.00 (t, J=7.7 Hz, 1H), 7.99 (br. s, 2H, NHs), 730-6.75 (m, 18H), 5.77 (t, J=5.7 Hz, 2H), 5.30 (d, J=4.8 Hz, 2H), 4.02 (m, 4H), 3.63 (m, 4H), 3.35 (d, J=12.7 Hz, 2H), 3.20 (td, J=12.7, 2.8 Hz, 2H), 2.60 (m, 4H), 2.36 (d, J=13.3 Hz, 2H), 224 (m, 2H), 2.05 (m, 6H), 1.80-1.65 (m, 10H), 1.50 (m, 4H), 1.20 (s, 6H), 1.18 (s, 6H), 0.85 (t, J=7.4 Hz, 6H); $^{13}$C NMR (CDCl$_3$, 75 MHz) (single diastereomer, mixture of rotamers) 208.2, 170.1, 167.7, 164.0, 159.3, 149.1, 142.0, 141.2, 139.3, 130.2, 128.9, 128.7, 126.5, 125.4, 119.4, 115.1, 113.2, 107.9, 67.0, 57.1, 51.6, 47.1, 44.5, 38.3, 37.9, 32.8, 32.1, 29.6, 28.0, 26.9, 25.4, 23.9, 23.5, 21.6, 9.1. MS(FAB): (M+Na)$^+$ 1198, (M+H)$^+$ 1176.

Example 4

N,N'-Bis[3-(3-((1R)-1-(2S)-(3,3-dimethyl-1,2-dioxopentyl)piperidine-2-carbonyloxo)-3-phenyl)propylphenoxy)propyl]pyridine-3,5-dicarboxamide (34)

Following the same procedure as in Example 1 except replacing pyridine-3,5-dicarboxylic acid for 1,4-phenylenediacetic acid, obtained 34 (32 mg, 39%) as a white solid. mp 62-64° C.; $^1$H NMR (CDCl$_3$, 300 MHz) (single diastereomer, mixture of rotamers) 9.09 (d, J=1.8 Hz, 2H), 8.42 (d, J=1.9 Hz, 1H), 7.30-6.80 (m, 20H), 5.78 (t, J=5.6 Hz, 2H), 528 (d, J=4.7 Hz, 2H), 4.12 (t, J=5.6 Hz, 4H), 3.68 (m, 4H), 3.36 (d, J=13.0 Hz, 2H), 3.18 (td, J=13.4, 3.4 Hz, 2H), 2.60 (m, 4H), 2.35 (d, J=13.2 Hz, 2H), 2.25 (m, 2H), 2.05 (m, 6H), 1.80-1.65 (m, 10H), 1.50 (m, 4H), 1.18 (s, 6H), 1.16 (s, 6H), 0.84 (t, J=7.4 Hz, 6H); $^{13}$C NMR (CDCl$_3$, 75 MHz) (single diastereomer, mixture of rotamers) 208.3, 170.1, 167.8, 165.2, 159.1, 150.9, 141.9, 141.3, 130.3, 130.2, 128.9, 128.7, 126.5, 119.5, 115.0, 112.7, 107.9, 67.0, 51.7, 47.1, 44.5, 38.7, 38.2, 32.8, 32.1, 26.8, 25.3, 23.9, 23.5, 21.5, 9.1. MS(FAB): (M+Na)$^+$ 1198, (M+H)$^+$ 1176.

Example 5

N,N'-Bis[3-(3-((1R)-1-((2S)-(3,3-dimethyl-1,2-dioxopentyl)piperidine-2-carbonyloxo)-3-phenyl)propylphenoxy)propyl]N-methyl-pyridinium-3,5-dicarboxamide iodide (35)

A solution of 34 (10 mg, 8.5 mmol) in acetone (1.0 mL) was treated with MeI (60 mL, 10.2 mmol). The mixture was left to stand at room temperature under dark for 3 d and TLC (100% EtOAc) showed all starting material converted to a baseline compound. The resulting deep yellow solution was concentrated in vacuo to afford 35 (11 mg, 100%) as a yellow solid. $^1$H NMR (Acetone-d$_6$, 300 MHz) (single diastereomer, mixture of rotamers) 9.98 (s, 1H), 9.62 (s, 2H), 9.14 (br. s, 2H), 7.20-6.70 (m, 20H), 5.83 (t, J=5.2 Hz, 2H), 5.27 (d, J=4.5 Hz, 2H), 4.75 (s, 3H), 4.18 (t, J=6.4 Hz, 4H), 3.67 (q, J=6.1 Hz, 4H), 3.45 (d, J=13.4 Hz, 2H), 3.25 (m, 2H), 2.75 (m, 4H), 2.20-1.90 (m, 10H), 1.75 (m, 10H), 1.50 (m, 4H), 1.21 (s, 6H), 1.19 (s, 6H), 0.85 (t, J=7.5 Hz, 6H); $^{13}$C NMR (Acetone-d$_6$, 75 MHz) (single diastereomer, mixture of rotamers) 208.7, 170.8, 168.2, 162.1, 160.6, 148.7, 143.3, 142.6, 130.8, 129.6, 127.2, 119.8, 115.6, 113.9, 104.0, 77.8, 67.2, 52.5, 47.6, 45.3, 39.4, 38.1, 33.6, 32.8, 27.6, 26.1, 24.2, 23.8, 22.4, 9.5. MS(FAB): M$^+$ 1190.

Example 6

N,N'-Bis[3-(3-((1R)-1-((2S)-(3,3-dimethyl-1,2-dioxopentyl)piperidine-2-carbonyloxo)-3-phenyl)propylphenoxy)propyl]benzene-1,3-disulfonamide (36)

A solution of 24 (106 mg, 0.17 mmol) in CH$_2$Cl$_2$ (2.0 mL) was treated with Et$_3$N (71 mL, 0.51 mmol) and benzene-1,3-disulfonyl chloride (23 mg, 0.085 mmol). The mixture was stirred at room temperature overnight. The resulting yellow solution was then impregnated on silica gel and evaporated to dryness. Chromatography (silica gel, 50% EtOAc/hexanes) afforded 36 (64 mg, 61%) as a white solid. mp 58-60° C.; $^1$H NMR (CDCl$_3$, 300 MHz) (single diastereomer, mixture of rotamers) 8.39 (d, J=6.3 Hz, 1H), 8.03 (dd, J=7.8, 1.6 Hz, 2H), 7.57 (td, J=7.9, 4.4 Hz, 1H), 7.35-6.80 (m, 18H), 5.81 (m, 2H), 5.50 (m, 2H), 5.36 (d, J=4.4 Hz, 2 H), 3.95 (m, 4H), 3.43 (d, J=12.6 Hz, 2H), 3.22 (m, 6H), 2.65 (m, 4H), 2.43 (d, J=13.6 Hz, 2 H), 230 (m, 2H), 2.15 (m, 2H), 1.95 (m, 4H), 1.90-1.65 (m, 12H), 1.50 (m, 4H), 1.25 (s, 6H), 1.23 (s, 6H), 0.90 (t, J=7.4 Hz, 6H); $^{13}$C NMR (CDCl$_3$, 75 MHz) (single diastereomer, mixture of rotamers) 208.5, 170.1, 167.8, 159.0, 142.1, 141.9, 141.3, 131.1, 1305, 130.1, 128.9, 128.7, 126.5, 125.8, 119.5, 114.8, 112.7, 65.7, 57.2, 51.8, 47.1, 44.6, 41.2, 38.4, 32.9, 32.8, 32.1, 29.5, 26.8, 25.3, 23.9, 23.4, 21.6, 9.2, 9.1. MS(FAB): (M+Na)$^+$ 1269.

Example 7

N,N'-Bis[3-(3-((1R)-1-((2S)-(3,3-dimethyl-1,2-dioxopentyl)piperidine-2-carbonyloxo)-3-phenyl)propylphenoxy)propyl]5-aminobenzene-1,3-dicarboxamide (37)

A mixture of 5-aminoisophthalic acid (1.81 g, 10 mmol) and dioxane (60 mL) was treated with a solution of Na$_2$CO$_3$ (4.24 g, 40 mmol) in water (60 mL) and then with (Boc)$_2$O (3.5 mL, 15 mmol). The mixture was stirred at room temperature for 16 h. EtOAc (100 mL) was added to the mixture and 10% KHSO$_4$ (ca. 100 mL) added to bring the pH to 2. The organic layer was separated and the aqueous layer was extracted with EtOAc (2×100 mL). The combined EtOAc solution was washed with saturated brine, dried (Na$_2$SO$_4$), and concentrated in vacuo to give 5-tert-butyloxycarbamyl-benzene-1,3-dicarboxylic acid (2.8 g, 100%).

A mixture of the above diacid (477 mg, 1.5 mmol) and disuccinimidyl carbonate (768 mg, 3.0 mmol) in acetonitrile (20 mL) was treated with pyridine (364 mL, 4.5 mmol). The mixture was stirred vigorously at room temperature for 20 h. The resulting suspension was partitioned between EtOAc (150 mL) and 0.5 N HCl (50 mL). The organic layer was separated and then washed with water (50 mL), 10% NaHCO$_3$ (2×50 mL), saturated brine, dried (Na$_2$SO$_4$), and concentrated in vacuo. Chromatography (silica gel, 70% EtOAc/hexanes) afforded disuccinimidyl (5-tert-butyloxycarbamyl)benzene-1,3-dicarboxylate (193 mg, 27%) as a white solid. $^1$H NMR (CDCl$_3$, 300 MHz) 8.50 (s, 1H), 8.44 (s, 2H), 6.91 (s, 1H), 2.89 (s, 8H), 1.54 (s, 9H).

To a solution of 24 (81 mg, 0.127 mmol) in CH$_2$Cl$_2$ (2.0 mL) was added the above activated diester (30 mg, 0.064 mmol), followed by dropwise addition of Et$_3$N (53 mL, 0.38 mmol). The mixture was stirred at room temperature for 4 h. The resulting clear solution was impregnated on silica gel and evaporated to dryness. Chromatography (silica gel, 50-70% EtOAc/hexanes) provided N-Boc-37 (56 mg, 68%) as a white solid. $^1$H NMR (CDCl$_3$, 300 MHz) (single diastereomer, mixture of rotamers) 8.01 (s, 2H), 7.93 (s, 1H), 735-6.85 (m, 21H), 5.83 (t, J=6.0 Hz, 2H), 5.34 (d, J=4.6 Hz, 2H), 4.14 (t, J=5.2 Hz, 4H), 3.70 (m, 4H), 3.42 (d, J=12.8 Hz, 2H), 3.22 (t, J=10.2 Hz, 2H), 2.65 (m, 4H), 2.40 (d, J=13.0 Hz, 2H), 2.30 (m, 2H), 2.15 (m, 6H), 1.85-1.65 (m, 10H), 1.57 (s, 9H), 1.50 (m, 4H), 1.25 (s, 6H), 1.23 (s, 6H), 0.91 (t, J=7.4 Hz, 6H); $^{13}$C NMR (CDCl$_3$, 75 MHz) (single diastereomer, mixture of rotamers) 208.4, 170.1, 167.8, 166.8, 159.3, 153.1, 141.7, 141.3, 139.9, 136.1, 130.1, 128.8, 128.7, 126.5, 119.7, 119.4, 115.0, 112.8, 66.7, 51.7, 47.1, 44.5, 38.4, 38.2, 32.8, 32.1, 29.4, 28.7, 26.8, 25.3, 23.4, 21.5, 9.1.

A solution of N-Boc-37 (20 mg, 0.016 mmol) in CH$_2$Cl$_2$ (4.0 mL) was treated with trifluoroacetic acid (0.8 mL) and the mixture was stirred at room temperature for 1 h. The mixture was diluted with toluene (150 mL) and concentrated in vacuo to give 37 trifluoroacetic acid salt (20 mg, 96%) as a colorless gum. $^1$H NMR (CDCl$_3$, 300 MHz) (single diastereomer, mixture of rotamers) 7.67 (s, 1H), 7.45-6.90 (m, 22H), 5.88 (m, 2H), 5.40 (d, J=4.6 Hz, 2H), 4.80 (br. s, 4H), 4.20 (m, 4H), 3.75 (m, 4H), 3.45 (d, J=12.7 Hz, 2H), 3.32 (m, 2H), 2.75 (m, 4H), 2.50-230 (m, 4H), 2.20 (m, 6H), 1.78 (m, 10H), 1.50 (m, 4H), 1.32 (s, 6H), 1.30 (s, 6H), 0.98 (t, J=7.4 Hz, 6H). MS(FAB): (M+H)$^+$ 1190.

Example 8

N,N'-Bis[3-(3-((1R)-1-((2S)-(3,3-dimethyl-1,2-dioxopentyl)piperidine-2-carbonyloxo)-3-phenyl)propylphenoxy)propyl](±)-2,6-diaminopimelamide (38)

Following the same procedures as in Example 7 except replacing (±)-2,6-diaminopimelic acid for 5-aminoisophthalic acid, obtained di-Boc-38 (51 mg, 54%) as a white solid. $^1$H NMR (CDCl$_3$, 300 MHz) (single diastereomer, mixture of rotamers) 7.35-6.50 (m, 20H), 5.84 (t, J=5.8 Hz, 2H), 5.45-5.20 (m, 4H), 4.08 (t, J=5.4 Hz, 4H), 3.55-3.30 (m, 6H), 3.24 (t, J=12.5 Hz, 2H), 2.70 (m, 4H), 2.42 (d, J=13.0 Hz, 2H), 2.35 (m, 2H), 2.20 (m, 2H), 2.05 (m, 4H), 2.00-1.65 (m, 14H), 1.50 (m, 4H), 1.47 (s, 18H), 1.28 (s, 6H), 1.25 (s, 6H), 0.94 (t, J=7.4 Hz, 6H); $^{13}$C NMR (CDCl$_3$, 75 MHz) (single diastereomer, mixture of rotamers) 208.3, 170.1, 159.3, 141.8, 141.3, 130.1, 128.9, 128.7, 126.5, 119.3, 113.1, 80.4, 66.7, 51.7, 47.1, 44.5, 38.3, 32.8, 32.1, 29.5, 28.74, 28.72, 26.9, 25.3, 24.0, 23.4, 21.6, 9.1.

A solution of di-Boc-38 (20 mg, 0.014 mmol) in CH$_2$Cl$_2$ (4.0 mL) was treated with trifluoroacetic acid (0.8 mL) and the mixture was stirred at room temperature for 1 h. The mixture was diluted with toluene (150 mL) and concentrated in vacuo to give 38 di-(trifluoroacetic acid) salt (18.9 mg, 94%) as a colorless gum. $^1$H NMR (CDCl$_3$, 300 MHz) (single diastereomer, mixture of rotamers) 7.40-6.85 (m, 20H), 5.85 (m, 2H), 5.38 (m, 2H), 4.05 (m, 6H), 3.45-3.25 (m, 8H), 2.70 (m, 4H), 2.45 (m, 2H), 2.40 (m, 2H), 2.20 (m, 2H), 2.05 (m, 4H), 1.95-1.60 (m, 14H), 1.50 (m, 4H), 1.28 (s, 6H), 1.27 (s, 6H), 0.95 (t, J=7.4 Hz, 6H). MS(FAB): (M+H)$^+$ 1199.

Example 9

N,N'-Bis[3-(3-((1R)-1-((2S)-(3,3-dimethyl-1,2-dioxopentyl)piperidine-2-carbonyloxo)-3-phenyl)propylphenoxy)propyl]triethyleneglycol-1,10-biscarbamate (39)

To a solution of 24 (85 mg, 0.13 mmol) in CH$_2$Cl$_2$ at 0° C. was added Et$_3$N, followed by triethylene glycol bis(chloroformate). The mixture was stirred at 0° C. for 1 h, and TLC showed no starting material left. The mixture was concentrated in vacuo and the residue was chromatographed on silica (70-80% EtOAc/hexanes) to give 39 as a colorless gum, 40 mg (48%). $^1$H NMR (CDCl$_3$, 300 MHz) (single diastereomer, mixture of rotamers) 7.25-6.70 (m, 18H), 5.71 (t, J=5.8 Hz, 2H), 5.25 (d, J=4.7 Hz, 2H), 5.12 (br. s., 2H), 4.15 (t, J=4.4 Hz, 4H), 3.95 (t, J=5.9 Hz, 4H), 3.60 (t, J=4.8 Hz, 4H), 3.57 (s, 4H), 3.30 (m, 6H), 3.10 (td, J=12.7, 3.0 Hz, 2H), 2.50 (m, 4H), 2.30 (d, J=13.7 Hz, 2H), 2.20 (m, 2H), 2.05 (m, 2H), 1.92 (t, J=6.2 Hz, 4H), 1.75-1.50 (m, 10H), 1.35 (m, 4H), 1.16 (s, 6H), 1.13 (s, 6H), 0.81 (t, J=7.4 Hz, 6H); $^{13}$C NMR (CDCl$_3$, 75 MHz) (single diastereomer, mixture of rotamers) 208.2, 170.1, 167.6, 159.3, 159.9, 156.9, 141.7, 141.3, 130.1, 128.9, 128.7, 126.5, 119.4, 114.8, 113.2, 71.0, 70.1, 66.0, 64.3, 51.7, 47.1, 44.5, 39.2, 38.8, 38.3, 33.0, 32.9, 32.1, 29.9, 26.8, 25.4, 23.9, 23.8, 23.5, 21.6, 9.1. MS(FAB): (M+Na)$^+$ 1269.

Example 10

1,4-Xylyldiamine N,N'-bis[2-(3-((1R)-1-((2S)-(3,3-dimethyl-1,2-dioxopentyl)piperidine-2-carbonyloxo)-3-phenyl)propy)phenoxyacetamide] (40)

A solution of carboxylic acid 25 (104 mg, 0.20 mmol) in acetonitrile (2.0 mL) was treated with disuccinimidyl carbonate (56 mg, 0.22 mmol) and pyridine (48 mL, 0.60 mmol). The mixture was stirred at room temperature overnight. The mixture was then partitioned between EtOAc (70 mL) and water (50 mL). The organic phase was separated, washed with saturated brine, dried (Na$_2$SO$_4$), and concentrated in vacuo to give a white foam (115 mg, 93%). The activated succinimidyl ester was redissolved in anhydrous acetonitrile (2.0 mL). The solution was then treated with triethylamine (75 mL, 0.54 mmol) followed by a solution of 1,4-xylyldiamine in DMF (0.32 M, 288 mL, 0.092 mmol). The resulting suspension was stirred at room temperature for 1 h and TLC showed no starting material left. The mixture was partitioned between EtOAc (50 mL) and water (20 mL). The organic layer was separated, washed with 0.5 N HCl (aq.), saturated brine, dried (Na$_2$SO$_4$) and concentrated in vacuo. Chromatography (silica gel, 70% EtOAc/hexanes) afforded 40 (42 mg, 40%) as a white solid: mp 59-61° C.; $^1$H NMR (CDCl$_3$, 300 MHz) (single diastereomer, mixture of rotamers) 7.25-6.70 (m, 22H), 5.69 (m, 2H), 5.22 (d, J=4.8 Hz, 2H), 4.46 (s, 4H), 4.43 (d, J=3.9 Hz, 4H), 3.27 (d, J=13.2 Hz, 2H), 3.06 (td, J=12.6, 2.6 Hz, 2H), 2.50 (m, 4H), 2.27 (d, J=13.4 Hz, 2H), 2.16 (m, 2H), 2.00 (m, 2H), 1.75-1.50 (m, 10H), 1.35 (m, 4H), 1.12 (s, 6H), 1.10 (s, 6H), 0.78 (t, J=7.4 Hz, 6H); $^{13}$C NMR (CDCl$_3$, 75 MHz) (single diastereomer, mixture of rotamers) 208.3, 170.0, 168.4, 168.3, 167.6, 157.7, 142.2, 142.1, 141.1, 137.6, 130.4, 128.9, 128.7, 128.5, 126.6, 120.6, 114.3, 113.8, 67.7, 57.0, 51.6, 47.1, 445, 43.0, 39.2, 38.4, 38.1, 32.9, 32.1, 32.0, 26.8, 25.3, 23.9, 23.5, 21.6, 9.2. MS(FAB): (M+Na)$^+$ 1169, (M+H)$^+$ 1147.

Example 11

1,4-Bis(3-aminopropyl)piperazine N,N'-bis[2-(3-((1R)-1-((2S)-(3,3-dimethyl-1,2-dioxopentyl)piperidine-2-carbonyloxo)-3-phenyl)propyl)phenoxyacetamide] (41)

Following the same method as in Example 10 except replacing 1,4-bis(3-aminopropyl)piperazine for 1,4-xylyldiamine, obtained 41 (35 mg, 53%) as a white solid. $^1$H NMR (CDCl$_3$, 300 MHz) (single diastereomer, mixture of rotamers) 7.55-6.90 (m, 20H), 5.93 (t, J=5.6 Hz, 2H), 5.46 (d, J=4.8 Hz, 2H), 4.63 (s, 4H), 3.70-3.50 (m, 6H), 3.37 (m, 2H), 2.95-2.20 (m, 24H), 1.90 (m, 16H), 1.60 (m, 4H), 1.37 (s, 6H), 1.35 (s, 6H), 1.03 (t, J=7.5 Hz, 6H); $^{13}$C NMR (CDCl$_3$, 75 MHz) (single diastereomer, mixture of rotamers) 208.2, 170.0, 168.4, 167.7, 158.0, 142.3, 141.1, 130.4, 128.9, 128.7, 126.6, 120.5, 115.0, 113.8, 107.9, 68.2, 51.6, 47.1, 44.5, 38.5, 32.9, 26.8, 25.3, 23.9, 235, 21.6, 9.1. MS(FAB): (M+H)$^+$ 1211.

Example 12

3,3'-Diamino-N-methyldipropylamine N,N'-bis[2-(3-((1R)-1-((2S)-(3,3-dimethyl-1,2-dioxopentyl)piperidine-2-carbonyloxo)-3-phenyl)propy)phenoxyacetamide] (42)

Following the same method as in Example 10 except replacing 3,3'-Diamino-N-methyldipropylamine for 1,4-xylyldiamine, obtained 42 (28 mg, 48%) as a colorless gum. $^1$H NMR (CDCl$_3$, 300 MHz) (single diastereomer, mixture of rotamers) 7.50-6.75 (m, 20H), 5.76 (t, J=5.8 Hz, 2H), 5.29 (d, J=4.8 Hz, 2H), 4.45 (s, 4H), 3.35 (m, 6H), 3.17 (td, J=12.6, 2.7 Hz, 2H), 2.60 (m, 4H), 2.35 (m, 6H), 2.25 (m, 2H), 2.05 (m, 5H), 1.70 (m, 14H), 1.40 (m, 4H), 1.20 (s, 6H), 1.18 (s, 6H), 0.86 (t, J=7.5 Hz, 6H); $^{13}$C NMR (CDCl$_3$, 75 MHz) (single diastereomer, mixture of rotamers) 208.2, 170.0, 168.4, 167.7, 158.0, 142.2, 141.1, 130.4, 128.9, 128.7, 126.5, 120.3, 115.0, 114.6, 113.7, 108.0, 67.9, 56.4, 51.6, 47.1, 44.5, 38.4, 33.0, 32.9, 32.1, 26.8, 25.3, 23.9, 23.5, 21.6, 21.4, 9.1. MS(FAB): (M+H)$^+$ 1156, (M+Na)$^+$ 1178.

Example 13

1,5-Diaminopentane N,N'-bis[2-(3-((1R)-1-((2S)-(3,3-dimethyl-1,2-dioxopentyl)piperidine-2-carbonyloxo)-3-phenyl)propyl)phenoxyacetamide] (43)

Following the same method as in Example 10 except replacing 1,5-diaminopentane for 1,4-xylyldiamine, obtained 43 (18 mg, 30%) as a colorless gum. $^1$H NMR (CDCl$_3$, 300 MHz) (single diastereomer, mixture of rotamers) 7.40-7.00 (m, 18H), 6.80 (br. s, NHs, 2H), 5.85 (m, 2H), 533 (d, J=4.7 Hz, 2H), 4.50 (s, 4H), 3.37 (m, 6H), 3.20 (td, J=12.7, 2.7 Hz, 2 H), 2.65 (m, 4H), 2.38 (d, J=13.4 Hz, 2H), 228 (m, 2H), 2.14 (m, 2H), 1.90-1.40 (m, 20H), 1.24 (s, 6H), 1.22 (s, 6H), 0.90 (t, J=7.4 Hz, 6H); $^{13}$C NMR (CDCl$_3$, 75 MHz) (single diastereomer, mixture of rotamers) 208.2, 170.0, 168.3, 167.7, 157.8, 142.2, 141.2, 130.4, 128.9, 128.7, 126.5, 120.5, 114.2, 113.9, 67.8, 51.6, 47.1, 44.5, 39.2, 38.4, 32.9, 32.0, 29.6, 26.8, 25.4, 24.4, 23.9, 235, 21.6, 9.1. MS(FAB): (M+Na)$^+$ 1135.

Example 14

1,5-Diamino-3-oxapetane N,N'-bis[2-(3-((1R)-1-((2S)-(3,3-dimethyl-1,2-dioxopentyl)piperidine-2-carbonyloxo)-3-phenyl)propyl)phenoxyacetamide] (48)

Following the same method as in Example 10 except replacing 1,5-diamino-3-oxapentane dihydrochloride (Aldrich) for 1,4-xylyldiamine, obtained 48 (23 mg, 39%) as a colorless gum. $^1$H NMR (CDCl$_3$, 300 MHz) (single diastereomer, mixture of rotamers) 7.30-6.80 (m, 20H), 5.80 (m, 2H), 5.30 (d, J=4.9 Hz, 2H), 4.48 (s, 4H), 3.50 (br. s, 8H), 3.36 (d, J=13.6 Hz, 2H), 3.16 (td, J=12.6, 2.7 Hz, 2H), 2.60 (m, 4H), 2.36 (d, J=13.8 Hz, 2H), 2.26 (m, 2 H), 2.10 (m, 2H), 1.80-1.60 (m, 10H), 1.50 (m, 4H), 1.20 (s, 6H), 1.19 (s, 6H), 0.87 (t, J=7.5 Hz, 6H); $^{13}$C NMR (CDCl$_3$, 75 MHz) (single diastereomer, mixture of rotamers) 208.2, 170.0, 168.5, 167.7, 157.8, 142.2, 141.1, 130.4, 128.9, 128.7, 126.5, 120.5, 114.6, 113.7, 108.1, 69.9, 67.8, 51.6, 47.1, 44.5, 39.1, 38.4, 32.9, 32.0, 26.8, 25.3, 23.9, 23.5, 21.6, 21.4, 9.1. MS(FAB): (M+Na)$^+$ 1137.

Example 15

1,8-Diamino-3,6-dioxaoctane N,N'-bis[2-(3-((1R)-1-((2S)-(3,3-dimethyl-1,2-dioxopentyl)piperidine-2-carbonyloxo)-3-phenyl)propyl)phenoxyacetamide] (53)

Following the same method as in Example 10 except replacing 1,8-diamino-3,6-dioxaoctane (Fluka) for 1,4-xylyldiamine, obtained 53 (23 mg, 32%) as a colorless gum. $^1$H NMR (CDCl$_3$, 300 MHz) (single diastereomer, mixture of rotamers) 7.35-6.85 (m, 20H), 5.80 (t, J=5.7 Hz, 2H), 5.33 (d, J=4.9 Hz, 2H), 451 (s, 4H), 3.60 (br. s, 12H), 3.40 (d, J=12.3 Hz, 2H), 3.20 (td, J=12.6, 2.8 Hz, 2H), 2.65 (m, 4H), 2.40 (d, J=13.4 Hz, 2H), 2.26 (m, 2H), 2.10 (m, 2H), 1.90-1.60 (m, 10H), 1.50 (m, 4H), 1.25 (s, 6H), 1.22 (s, 6H), 0.90 (t, J=7.4 Hz, 6H); $^{13}$C NMR (CDCl$_3$, 75 MHz) (single diastereomer, mixture of rotamers) 208.2, 170.0, 168.4, 167.7, 157.8, 142.2, 141.1, 130.4, 128.9, 128.7, 126.5, 120.5, 114.7, 113.6, 70.7, 70.1, 67.8, 51.6, 47.1, 44.5, 39.2, 38.4, 32.9, 32.0, 26.8, 25.3, 23.9, 23.5, 21.6, 21.4, 9.1. MS(FAB): (M+Na)$^+$ 1181.

Example 16

1,11-Diamino-3,6,9-trioxaundecane N,N'-bis[2-(3-((1R)-1-(2S)-(3,3-dimethyl-1,2-dioxopentyl)piperidine-2-carbonyloxo)-3-phenyl)propyl)phenoxyacetamide] (59)

Following the same method as in Example 10 except replacing 1,11-Diamino-3,6,9-trioxaundecane (prepared using literature procedure of Dietrich, B.; Lehn, J.-M.; Sauvage, J. P.; Blanzat, *J. Tetrahedron,* 1973, 29, 1628) for 1,4-xylyldiamine, obtained 59 (18 mg, 24%) as a colorless gum. $^1$H NMR (CDCl$_3$, 300 MHz) (single diastereomer, mixture of rotamers) 7.35-6.80 (m, 20H), 5.77 (t, J=6.0 Hz, 2H), 5.30 (d, J=4.9 Hz, 2H), 4.48 (s, 4H), 3.60 (m, 16H), 3.35 (d, J=13.5 Hz, 2H), 3.16 (td, J=12.6, 2.9 Hz, 2H), 2.65 (m, 4H), 2.37 (d, J=13.6 Hz, 2 H), 2.25 (m, 2H), 2.05 (m, 2H), 1.80-1.60 (m, 12H), 1.50 (m, 4H), 1.21 (s, 6H), 1.19 (s, 6H), 0.87 (t, J=7.4 Hz, 6H); $^{13}$C NMR (CDCl$_3$, 75 MHz) (single diastereomer, mixture of rotamers) 208.2, 170.0, 168.4, 167.7, 157.8, 142.2, 141.1, 130.4, 128.9, 128.7, 126.5, 120.5, 114.7, 113.6, 108.0, 70.9, 70.7, 70.1, 67.8, 51.6, 47.1, 44.5, 39.2, 38.4, 32.9, 32.0, 26.8, 25.3, 23.9, 23.5, 21.6, 9.1. MS(FAB): (M+Na)+ 1125.

Example 17

1,5-Diaminopentane N,N'-bis[2-(3-((1R)-1-(2S)-(3,3-dimethyl-1,2-dioxopentyl)piperidine-2-carbonyloxo)-3-(3,4-dimethoxyphenyl)))propyl)phenoxy-acetamide] (44)

Following the same method as in Example 10 except replacing the acid monomer 26 for 25 and replacing 1,5-diaminopentane for 1,4-xylyldiamine, obtained 44 (58 mg, 49%) as a white foam. $^1$H NMR (CDCl$_3$, 300 MHz) (single diastereomer, mixture of rotamers) 7.35-6.65 (m, 16H), 5.79 (m, 2H), 5.33 (d, J=4.8 Hz, 2H), 4.49 (s, 4H), 3.87 (s, 6H), 3.86 (s, 6H), 3.35 (m, 6H), 3.20 (m, 2H), 2.95 (m, 2H), 2.60 (m, 4H), 2.38 (d, J=13.4 Hz, 2H), 2.28 (m, 2H), 2.10 (m, 2H), 1.90-1.40 (m, 20H), 1.23 (s, 6H), 1.22 (s, 6H), 0.90 (t, J=7.4 Hz, 6H); $^{13}$C NMR (CDCl$_3$, 75 MHz) (single diastereomer, mixture of rotamers) 208.2, 170.0, 168.3, 168.2, 167.7, 157.8, 149.3, 147.8, 142.3, 133.8, 130.4, 120.6, 114.2, 113.9, 112.2, 111.8, 108.0, 67.8, 56.3, 56.2, 51.6, 47.1, 44.5, 39.2, 38.6, 38.3, 32.9, 31.6, 29.6, 26.8, 25.3, 24.4, 23.8, 23.6, 9.1. MS(FAB): (M+Na)+ 1255.

Example 18

1,5-Diamino-3-oxapetane N,N'-bis[2-(3-((1R)-1-((2S)-(3,3-dimethyl-1,2-dioxopentyl)piperidine-2-carbonyloxo)-3-(3,4-dimethoxyphenyl))propyl)phenoxy-acetamide] (49)

Following the same method as in Example 10 except replacing the acid monomer 26 for 25 and replacing 1,5-diamino-3-oxapentane dihydrochloride (Aldrich) for 1,4-xylyldiamine, obtained 49 (73 mg, 62%) as a white foam. $^1$H NMR (CDCl$_3$, 300 MHz) (single diastereomer, mixture of rotamers) 7.35-6.65 (m, 16H), 5.79 (m, 2H), 5.33 (d, J=4.8 Hz, 2H), 4.51 (s, 4H), 3.87 (s, 6H), 3.86 (s, 6H), 3.55 (br.s, 8H), 3.35 (m, 2H), 3.20 (m, 2H), 2.60 (m, 4H), 2.38 (d, J=13.4 Hz, 2H), 2.28 (m, 2H), 2.10 (m, 2H), 1.90-1.40 (m, 20H), 1.23 (s, 6H), 1.22 (s, 6H), 0.90 (t, J=7.4 Hz, 6H); $^{13}$C NMR (CDCl$_3$, 75 MHz) (single diastereomer, mixture of rotamers) 208.2, 170.0, 168.5, 168.4, 167.7, 157.8, 149.3, 147.8, 142.3, 133.7, 130.4, 120.5, 114.6, 113.7, 112.2, 111.8, 69.9, 67.8, 56.3, 56.2, 51.6, 47.1, 44.5, 39.1, 38.6, 32.9, 31.6, 26.8, 25.3, 23.8, 23.6, 21.6, 9.1. MS(FAB): (M+Na)+ 1257.

Example 19

1,8-Diamino-3,6-dioxaoctane N,N'-bis[2-(3-((1R)-1-((2S)-(3,3-dimethyl-1,2-dioxo-pentyl)piperidine-2-carbonyloxo)-3-(3,4-dimethoxyphenyl))propyl)phenoxy-acetamide] (54)

Following the same method as in Example 10 except replacing the acid monomer 26 for 25 and replacing 1,8-diamino-3,6-dioxaoctane (Fluka) for 1,4-xylyldiamine, obtained 54 (54 mg, 49%) as a white foam. $^1$H NMR (CDCl$_3$, 300 MHz) (single diastereomer, mixture of rotamers) 7.35-6.65 (m, 16H), 5.79 (m, 2H), 533 (d, J=4.8 Hz, 2H), 4.50 (s, 4H), 3.87 (s, 6H), 3.86 (s, 6H), 3.59 (br.s, 12H), 3.35 (m, 2H), 3.20 (m, 2H), 2.60 (m, 4H), 2.38 (d, J=13.4 Hz, 2 H), 2.28 (m, 2H), 2.10 (m, 2H), 1.90-1.40 (m, 20H), 1.23 (s, 6H), 1.22 (s, 6H), 0.90 (t, J=7.4 Hz, 6H); $^{13}$C NMR (CDCl$_3$, 75 MHz) (single diastereomer, mixture of rotamers) 208.2, 170.1, 168.4, 167.7, 157.8, 149.3, 147.8, 142.3, 133.7, 130.4, 120.5, 114.7, 113.6, 112.2, 111.8, 70.6, 70.1, 67.8, 56.3, 56.2, 51.6, 47.1, 44.5, 39.2, 38.6, 32.9, 31.6, 26.8, 25.3, 23.8, 23.6, 21.6, 9.1. MS(FAB): (M+Na)+ 1301.

Example 20

1,11-Diamino-3,6,9-trioxaundecane N,N'-bis[2-(3-((1R)-1-((2S)-(3,3-dimethyl-1,2-dioxo-pentyl)piperidine-2-carbonyloxo)-3-(3,4-dimethoxyphenyl))propyl)phenoxy-acetamide] (60)

Following the same method as in Example 10 except replacing the acid monomer 26 for 25 and replacing 1,11-Diamino-3,6,9-trioxaundecane (prepared using literature procedure of Dietrich, B.; Lehn, J.-M.; Sauvage, J. P.; Blanzat, J. *Tetrahedron*, 1973, 29, 1628) for 1,4-xylyldiamine, obtained 60 (64 mg, 50%) as a colorless gum. $^1$H NMR (CDCl$_3$, 300 MHz) (single diastereomer, mixture of rotamers) 7.35-6.65 (m, 16H), 5.79 (m, 2H), 5.33 (d, J=4.8 Hz, 2H), 4.50 (s, 4H), 3.87 (s, 6H), 3.86 (s, 6H), 3.61 (m, 16H), 3.38 (m, 2H), 3.20 (m, 2H), 2.60 (m, 4H), 2.38 (m, 2H), 2.28 (m, 2H), 2.10 (m, 2H), 1.90-1.40 (m, 20H), 1.23 (s, 6H), 1.22 (s, 6H), 0.90 (t, J=7.4 Hz, 6H); $^{13}$C NMR (CDCl$_3$, 75 MHz) (single diastereomer, mixture of rotamers) 208.2, 170.1, 168.4, 167.7, 157.8, 149.3, 147.8, 142.3, 133.7, 130.4, 120.5, 114.7, 113.6, 1122, 111.8, 108.0, 70.6, 70.1, 67.8, 56.3, 56.2, 51.6, 47.1, 44.5, 39.2, 38.6, 32.9, 31.6, 26.8, 25.3, 23.8, 23.5, 21.6, 9.1. MS(FAB): (M+Na)+ 1345.

Example 21

1,5-Diaminopentane N,N'-bis[2-(3-((1R)-1-((2S)-(3,3-dimethyl-1,2-dioxopentyl)piperidine-2-carbonyloxo)-3-(3,4,5-trimethoxyphenyl))propyl)phenoxy-acetamide] (45)

Following the same method as in Example 10 except replacing the acid monomer 27 for 25 and replacing 1,5-diaminopentane for 1,4-xylyldiamine, obtained 45 (33 mg, 34%) as a white foam. $^1$H NMR (CDCl$_3$, 300 MHz) and $^{13}$C NMR (CDCl$_3$, 75 MHz) are correct. MS(FAB): (M+Na)+ 1315.

Example 22

1,5-Diamino-3-oxapetane N,N'-bis[2-(3-((1R)-1-(2S)-(3,3-dimethyl-1,2-dioxopentyl)piperidine-2-carbonyloxo)-3-(3,4,5-trimethoxyphenyl))propyl)phenoxy-acetamide] (50)

Following the same method as in Example 10 except replacing the acid monomer 27 for 25 and replacing 1,5-diamino-3-oxapentane dihydrochloride (Aldrich) for 1,4-xylyldiamine, obtained 50 (41 mg, 46%) as a white foam. $^1$H NMR (CDCl$_3$, 300 MHz) and $^{13}$C NMR (CDCl$_3$, 75 MHz) are correct. MS(FAB): (M+Na)+ 1317.

Example 23

1,8-Diamino-3,6-dioxaoctane N,N'-bis[2-(3-((1R)-1-((2S)-(3,3-dimethyl-1,2-dioxopentyl)piperidine-2-carbonyloxo)-3-(3,4,5-trimethoxyphenyl))propyl)phenoxy-acetamide] (55)

Following the same method as in Example 10 except replacing the acid monomer 27 for 25 and replacing 1,8- diamino-3,6-dioxaoctane (Fluka) for 1,4-xylyldiamine for 1,4-xylyldiamine, obtained 55 (37 mg, 38%) as a white foam. $^1$H NMR (CDCl$_3$, 300 MHz) and $^{13}$C NMR (CDCl$_3$, 75 MHz) are correct. MS(FAB): (M+Na)$^+$ 1361.

Example 24

1,11-Diamino-3,6,9-trioxaundecane N,N'-bis[2-(3-((1R)-1-((2S)-(3,3-dimethyl-1,2-dioxopentyl)piperidine-2-carbonyloxo)-3-(3,4,5-trimethoxyphenyl))propyl)phenoxy-acetamide] (61)

Following the same method as in Example 10 except replacing the acid monomer 27 for 25 and replacing 1,11-Diamino-3,6,9-trioxaundecane for 1,4-xylyldiamine, obtained 61 (27 mg, 32%) as a white foam. $^1$H NMR (CDCl$_3$, 300 MHz) and $^{13}$C NMR (CDCl$_3$, 75 MHz) are correct. MS(FAB): (M+Na)$^+$ 1405.

Example 25

1,5-Diaminopentane N,N'-bis[2-(3-((1R)-1-((2S)-(3,3-dimethyl-1,2-dioxopentyl)piperidine-2-carbonyloxo)-3-(3,4-methylenedioxyphenyl))propyl)phenoxy-acetamide] (46)

Following the same method as in Example 10 except replacing the acid monomer 28 for 25 and replacing 1,5-diaminopentane for 1,4-xylyldiamine, obtained 46 (42 mg, 42%) as a white foam. $^1$H NMR (CDCl$_3$, 300 MHz) and $^{13}$C NMR (CDCl$_3$, 75 MHz) are correct. MS(FAB): (M+Na)$^+$ 1223.

Example 26

5-Diamino-3-oxapetane N,N'-bis[2-(3-((1R)-1-((2S)-(3,3-dimethyl-1,2-dioxopentyl)piperidine-2-carbonyloxo)-3-(3,4-methylenedioxyphenyl))propyl)phenoxy-acetamide] (51)

Following the same method as in Example 10 except replacing the acid monomer 28 for 25 and replacing 1,5-diamino-3-oxapentane dihydrochloride (Aldrich) for 1,4-xylyldiamine, obtained 51 (39 mg, 34%) as a white foam. $^1$H NMR (CDCl$_3$, 300 MHz) and $^{13}$C NMR (CDCl$_3$, 75 MHz) are correct. MS(FAB): (M+Na)$^+$ 1225.

Example 27

1,8-Diamino-3,6-dioxaoctane N,N'-bis[2-(3-((1R)-1-(2S)-(3,3-dimethyl-1,2-dioxopentyl)piperidine-2-carbonyloxo)-3-(3,4-methylenedioxyphenyl))propyl)phenoxy-acetamide] (56)

Following the same method as in Example 10 except replacing the acid monomer 28 for 25 and replacing 1,8-diamino-3,6-dioxaoctane (Fluka) for 1,4-xylyldiamine for 1,4-xylyldiamine, obtained 56 (55 mg, 47%) as a white foam. $^1$H NMR (CDCl$_3$, 300 MHz) and $^{13}$C NMR (CDCl$_3$, 75 MHz) are correct. MS(FAB): (M+Na)$^+$ 1269.

Example 28

1,11-Diamino-3,6,9-trioxaundecane N,N'-bis[2-(3-((1R)-1-(2S)-(3,3-dimethyl-1,2-dioxopentyl)piperidine-2-carbonyloxo)-3-(3,4-methylenedioxyphenyl))propyl)phenoxy-acetamide] (62)

Following the same method as in Example 10 except replacing the acid monomer 28 for 25 and replacing 1,11-Diamino-3,6,9-trioxaundecane for 1,4-xylyldiamine, obtained 62 (52 mg, 42%) as a colorless gum. $^1$H NMR (CDCl$_3$, 300 MHz) and $^{13}$C NMR (CDCl$_3$, 75 MHz) are correct. MS(FAB): (M+Na)$^+$ 1313.

Example 29

1,5-Diaminopentane N,N'-bis[2-(3-((1R)-1-((2S)-(3,3-dimethyl-1,2-dioxopentyl)piperidine-2-carbonyloxo)-3-(3-pyridyl))propyl)phenoxyacetamide] (47)

Following the same method as in Example 10 except replacing the acid monomer 29 for 25 and replacing 1,5-diaminopentane for 1,4-xylyldiamine, obtained 47 (64 mg, 58%) as a white foam. $^1$H NMR (CDCl$_3$, 300 MHz) and $^{13}$C NMR (CDCl$_3$, 75 MHz) are correct. MS(FAB): (M+Na)$^+$ 1137.

Example 30

1,5-Diamino-3-oxapetane N,N'-bis[2-(3-((1R)-1-((2S)-(3,3-dimethyl-1,2-dioxopentyl)piperidine-2-carbonyloxo)-3-(3-pyridyl))propyl)phenoxyacetamide] (52)

Following the same method as in Example 10 except replacing the acid monomer 29 for 25 and replacing 1,5-diamino-3-oxapentane dihydrochloride (Aldrich) for 1,4-xylyldiamine, obtained 52 (52 mg, 55%) as a white foam. $^1$H NMR (CDCl$_3$, 300 MHz) and $^{13}$C NMR (CDCl$_3$, 75 MHz) are correct. MS(FAB): (M+Na)$^+$ 1139.

Example 31

1,8-Diamino-3,6-dioxaoctane N,N'-bis[2-(3-((1R)-1-(2S)-(3,3-dimethyl-1,2-dioxopentyl)piperidine-2-carbonyloxo)-3-(3-pyridyl))propyl)phenoxyacetamide] (57)

Following the same method as in Example 10 except replacing the acid monomer 29 for 25 and replacing 1,8-diamino-3,6-dioxaoctane (Fluka) for 1,4-xylyldiamine for 1,4-xylyldiamine, obtained 57 (48 mg, 47%) as a white foam. $^1$H NMR (CDCl$_3$, 300 MHz) and $^{13}$C NMR (CDCl$_3$, 75 MHz) are correct. MS(FAB): (M+Na)$^+$ 1183.

Example 32

1,11-Diamino-3,6,9-trioxaundecane N,N'-bis[2-(3-((1R)-1-((2S)-(3,3-dimethyl-1,2-dioxopentyl)piperidine-2-carbonyloxo)-3-(3-pyridyl))propyl)phenoxy-acetamide] (63)

Following the same method as in Example 10 except replacing the acid monomer 29 for 25 and replacing 1,11-Diamino-3,6,9-trioxaundecane for 1,4-xylyldiamine, obtained 63 (58 mg, 55%) as a colorless gum. $^1$H NMR (CDCl$_3$, 300 MHz) and $^{13}$C NMR (CDCl$_3$, 75 MHz) are correct. MS(FAB): (M+Na)$^+$ 1227.

Example 33

1,8-Diamino-3,6-dioxaoctane N,N'-bis[2-(3-((1R)-1-((2S)-(3,3-dimethyl-1,2-dioxopentyl)piperidine-2-carbonyloxo)-3-(3-indolyl))propyl)phenoxyacetamide] (58)

Following the same method as in Example 10 except replacing the acid monomer 30 for 25 and replacing 1,8- diamino-3,6-dioxaoctane (Fluka) for 1,4-xylyldiamine for 1,4-xylyldiamine, obtained 58 (20 mg, 20%) as a white foam. $^1$H NMR (CDCl$_3$, 300 MHz) and $^{13}$C NMR (CDCl$_3$, 75 MHz) are correct. MS(FAB): (M+Na)$^+$ 1259.

Example 34

Ethylenediamine N,N'-bis[2-(3-((1R)-1-(2S)-(3,3-dimethyl-1,2-dioxopentyl)piperidine-2-carbonyloxo)-3-(3,4-dimethoxyphenyl))propyl)phenoxy-acetamide] (64)

Following the same method as in Example 10 except replacing the acid monomer 26 for 25 and replacing ethylenediamine dihydrochloride for 1,4-xylyldiamine, obtained 64 (126 mg, 59%) as a white solid. $^1$H NMR (CDCl$_3$, 300 MHz) and $^{13}$C NMR (CDCl$_3$, 75 MHz) are correct. MS(FAB): (M+Na)$^+$ 1213.

Example 35

Ethylenediamine N,N'-bis[2-(3-((1R)-1-((2S)-(3,3-dimethyl-1,2-dioxopentyl)piperidine-2-carbonyloxo)-3-(3-pyridyl))propyl)phenoxyacetamide] (65)

Following the same method as in Example 10 except replacing the acid monomer 29 for 25 and replacing ethylenediamine dihydrochloride for 1,4-xylyldiamine, obtained 65 (79 mg, 42%) as a white solid. $^1$H NMR (CDCl$_3$, 300 MHz) and $^{13}$C NMR (CDCl$_3$, 75 MHz) are correct. MS(FAB): (M+H)$^+$ 1073.

Example 36

N,N'-Dimethylethylenediamine N,N'-bis[2-(3-((1R)-1-((2S)-(3,3-dimethyl-1,2-dioxopentyl)piperidine-2-carbonyloxo)-3-(3,4-dimethoxyphenyl))propyl)phenoxy-acetamide] (66)

Following the same method as in Example 10 except replacing the acid monomer 26 for 25 and replacing N,N'-dimethylethylenediamine for 1,4-xylyldiamine, obtained 66 (118 mg, 55%) as a white solid. $^1$H NMR (CDCl$_3$, 300 MHz) and $^{13}$C NMR (CDCl$_3$, 75 MHz) are correct. MS(FAB): (M+Na)$^+$ 1241.

Example 37

N,N'-Dimethylethylenediamine N,N'-bis[2-(3-((1R)-1-((2S)-(3,3-dimethyl-1,2-dioxopentyl)piperidine-2-carbonyloxo)-3-(3-pyridyl))propyl)phenoxyacetamide] (67)

Following the same method as in Example 10 except replacing the acid monomer 29 for 25 and replacing N,N'-dimethylethylenediamine for 1,4-xylyldiamine, obtained 67 (70 mg, 37%) as a white solid. $^1$H NMR (CDCl$_3$, 300 MHz) and $^{13}$C NMR (CDCl$_3$, 75 MHz) are correct. MS(FAB): (M+H)$^+$ 1101.

Synthetic Overview, Part II

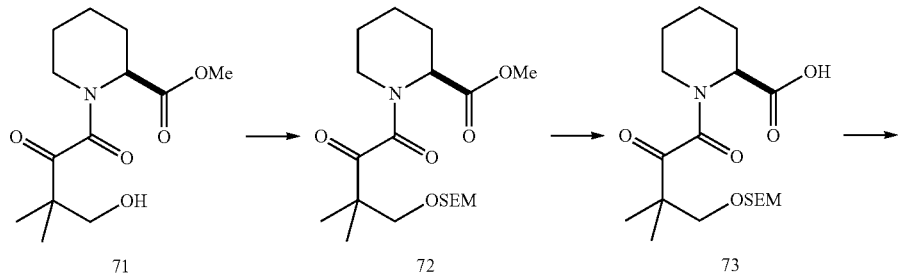

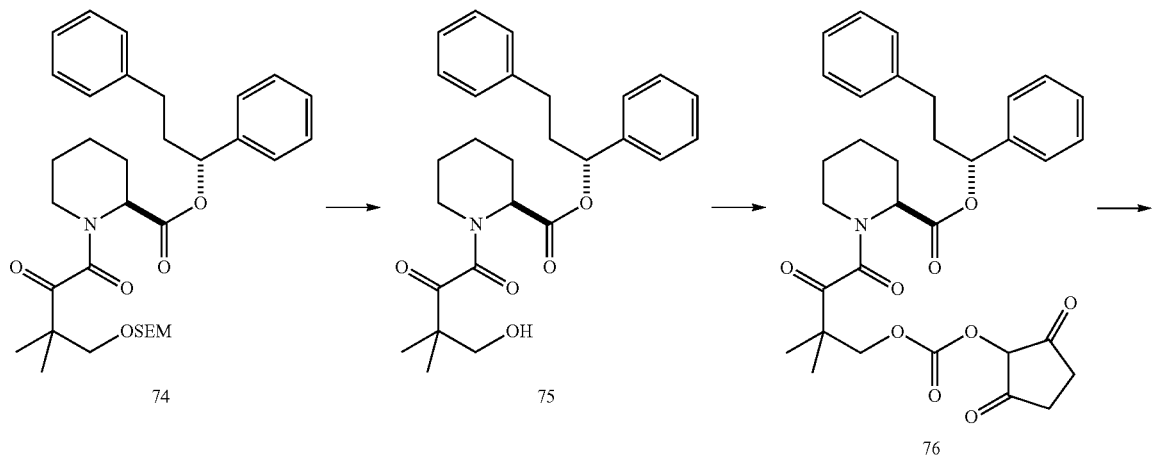

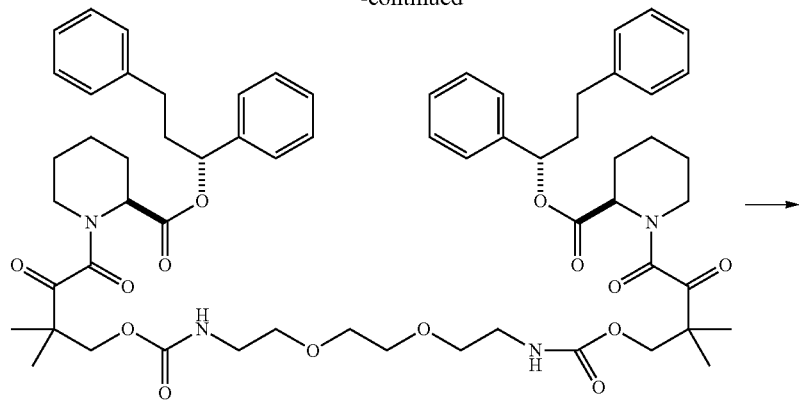

77

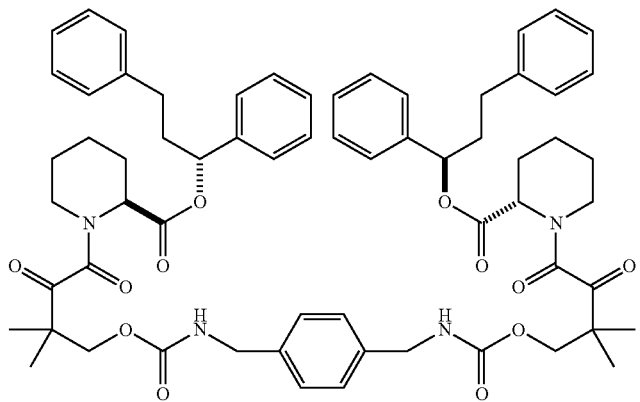

78

Synthetic Details

Methyl (2S)-1-(3,3-dimethyl-1,2-dioxo-4-hydroxy)butyl-2-piperidinecarboxylate, (71)

Prepared according to the procedure reported by D. A. Holt et al., *J. Am, Chem. Soc.* 1993, 115, 9925-9938 for the ethyl ester analog.

$^1$H NMR (CDCl$_3$) d 5.25 (dist d, J=5.2 Hz, 1H), 3.78 (s, 3H), 3.59-3.71 (m, 2H), 3.49 (br d, J=13.8 Hz, 1H), 3.37 (t, J=6.4 Hz, 1H), 3.18 (td, J=12.9, 3.3 Hz, 1H), 2.32 (br d, J=14.0 Hz, 1H), 1.25-1.80 (m, 5H), 1.23 (s, 6H). MS(DCI/NaI) m/z 289 (M+NH$_4$), 272 (M+H).

Methyl(2S)-1-{3,3-dimethyl-1,2-dioxo-4-[2-(trimethylsilyl)ethoxy]methoxy}butyl-2-piperidinecarboxylate, (72)

A solution of methyl (2S)-1-(3,3-dimethyl-1,2-dioxo-4-hydroxy)butyl-2-piperidinecarboxylate, 71 (1.80 g, 6.6 mmol), N,N'-diisopropylethylamine (1.03 g, 8.0 mmol), and 2-(trimethylsilyl)ethoxymethyl chloride (1.33 g, 8.0 mmol) in dichloromethane (25 mL) was stirred at room temperature for 21.5 h. The solution was concentrated and the residue was chromatographed (silica-gel, hexanes-ethyl acetate 10:1 to 6:1 gradient) to give the title compound (2.60 g) as a colorless liquid.

$^1$H NMR (CDCl$_3$) d 5.22 (br d, J=5.1 Hz, 1H), 4.62 (s, 2H), 3.73 (s, 3H), 3.49-3.71 (m, 5H), 3.14 (td, J=13.3, 3.4 Hz, 1H), 2.28 (br d, J=14.0 Hz, 1H), 1.18-1.77 (m, 5H), 1.30 (s, 3H), 1.27 (s, 3H), 0.84-0.94 (m, 2H), 0.00 (s, 9H). MS(FAB$^+$/NaI) m/z.

(2S)-1-{3,3-Dimethyl-1,2-dioxo-4-[2-(trimethylsilyl)ethoxy]methoxy}butyl-2-piperidinecarboxylic acid, (73)

A mixture of methyl (2S)-1-{3,3-dimethyl-1,2-dioxo-4-[2-(trimethylsilyl)ethoxy]methoxy}butyl-2-piperidinecarboxylate, 72 (2.50 g, 6.2 mmol), 1N lithium hydroxide (9.3 mL) and methanol (10 mL) was stirred at 0° C. for 30 min and then at room temperature for 7 h. The mixture was acidified with 1N HCl, diluted with water, and extracted with dichloromethane. The organic extract was washed with water, dried over anhydrous sodium sulfate, and concentrated to give a colorless oil (2.11 g) which was used without further purification.

$^1$H NMR (CDCl$_3$) d 10.25 (br s, 1H), 5.27 (d, J=4.9 Hz, 1H), 4.61 (s, 2H), 3.68 (dist. t, J=9.4, 9.9 Hz, 1H), 3.49-3.60 (m, 4H), 3.11-3.20 (m, 1H), 2.31 (br d, J=13.7 Hz, 1H), 1.36-1.79 (m, 5H), 1.29 (s, 3H), 1.27 (s, 3H), 0.91 (td, J=8.4, 3.0 Hz, 2H), 0.00 (s, 9H). $^{13}$C NMR (CDCl$_3$) d 207.5, 176.9, 168.7, 96.4, 75.0, 66.6, 52.5, 48.8, 45.3, 27.7, 26.2, 23.9 (2C), 22.6, 19.5, 0.00. MS(FAB$^-$) m/z 386 (M–H).

(1R)-1,3-Diphenyl-1-propyl (2S)-1-{3,3-dimethyl-1,2-dioxo-4-[2-(trimethylsilyl)ethoxy]methoxy}butyl-2-piperidinecarboxylate, (74)

A solution of (2S)-1-{3,3-dimethyl-1,2-dioxo-4-[2-(trimethylsilyl)ethoxy]methoxy}butyl-2-piperidinecarboxylic acid, 73 (1.00 g, 2.6 mmol) and (1R)-1,3-diphenyl-1-propanol (0.72 g, 3.4 mmol) in dichloromethane (10 mL) was treated with N,N-dicyclohexylcarbodiimide (0.70 g, 3.4 mmol) and 4-dimethylaminopyridine (0.22 g, 1.8 mmol). The resulting suspension was stirred at room temperature under a nitrogen atmosphere for 17 h. The mixture was then diluted with a small amount of ethyl acetate, filtered, and concentrated, and the residue was subjected to column chromatography (silica-gel, hexanes-ethyl acetate 8:1) to afford the title compound (1.33 g) as a colorless oil $^1$H NMR (CDCl$_3$) d 7.14-7.32 (m, 10H), 5.27-5.47 (m, 1H), 5.08 (br d, J=5.2 Hz, 1H), 4.59 (AB q, J$_{AB}$=6.8 Hz, 2H), 3.66 (dd, J=9.2, 8.6 Hz, 1H), 3.48-3.62 (m, 3H), 3.33 (br d, J=13.1 Hz, 1H), 2.70-2.92 (m, 5H), 2.00 (br d, J=11.5 Hz, 1H), 1.21-1.49 (m, 5H), 1.27 (s, 3H), 1.25 (s, 3H), 0.86-0.95 (m, 2H), 0.00 and −0.02 (2xs, 9H).

MS(FAB$^+$/NaI) m/z 604 (M+Na). Exact Mass: Calc. (M+Na) for C$_{33}$H$_{47}$NSiO$_6$, 604.3070. found, 604.3073.

(1R)-1,3-Diphenyl-1-propyl (2S)-1-(3,3-dimethyl-1,2-dioxo-4-hydroxy)butyl-2-piperidinecarboxylate, (75)

A solution of (1R)-1,3-diphenyl-1-propyl (2S)-1-{3,3-dimethyl-1,2-dioxo-4-[2-(trimethylsilyl)ethoxy]methoxy}butyl-2-piperidinecarboxylate, 74 (0.75 g, 1.3 mmol) and 48 wt % HF (05 mL) in acetonitrile (25 mL) was stirred at room temperature for 4 h, and then partitioned between 10% aqueous sodium bicarbonate and ethyl acetate. The organic layer was decanted, washed with water, dried over anhydrous sodium sulfate, and concentrated, and the residue chromatographed (silica-gel, hexanes-ethyl acetate 4:1 to 2:1 gradient) to afford 75 (0.45 g) as a colorless oil).

$^1$H NMR (CDCl$_3$) d 7.10-7.27 (m, 10H), 5.38-5.47 (m, 1H), 5.04 (br d, J=5.3 Hz, 1H), 3.47-3.621 (m, 3H), 3.29 (br d, J=13.9 Hz, 1H), 2.67-2.93 (m, 5H), 2.00 (br d, J=12.8 Hz, 1H), 1.17-157 (m, 5H), 1.15 (s, 3H), 1.14 (s, 3H). MS(FAB$^+$/NaI) m/z 474 (M+Na). Exact Mass: Calc. (M+Na) for C$_{25}$H$_{33}$NO$_5$, 474.2256. found, 474.2273.

(1R)-1,3-Diphenyl-1-propyl (2S)-1-[3,3-dimethyl-1,2-dioxo-4-(1-succinimidyloxycarbonyl)oxy]butyl-2-piperidinecarboxylate, (76)

A solution of (1R)-1,3-diphenyl-1-propyl (2S)-1-(3,3-dimethyl-1,2-dioxo-4-hydroxy)butyl-2-piperidinecarboxylate, 75 (223 mg, 0.49 mmol) in dichloromethane (13 mL) was treated with N,N-diisopropylethylamine (0.8 mL), and N,N'-disuccinimidyl carbonate (385 mg), and the mixture stirred at room temperature for 66 h. It was then washed with saturated sodium bicarbonate, dried over anhydrous sodium sulfate, and concentrated to afford a yellow oil (280 mg) which was used without further purification.

$^1$H NMR (C$_6$D$_6$) d 7.11-7.32 (m, 10H), 5.56-5.65 (m, 1H), 5.36 (br d, J=5.1 Hz, 1H), 4.51 (d, J=10.5 Hz, 1H), 4.17 (d, J=10.5 Hz, 1H), 352 (br d, J=13.4 Hz, 1H), 2.71-3.11 (m, 5H), 1.99 (br d, J=14.4 Hz, 1H), 1.70 (br s, 4H), 1.01-1.38 (m, 11H).

$^{13}$C NMR (C$_6$D$_6$) d 205.4, 171.0, 169.7, 168.2, 153.5, 139.2 (139.0), 131.2, 130.2, 130.1, 129.8, 129.5, 129.2, 128.3 (128.2), 77.9, 76.9, 53.1, 48.4, 45.3, 41.9, 41.8, 27.7, 26.6 (2C), 26.3, 23.5, 22.5, 22.3. MS(FAB$^+$/NaI) m/z 615 (M+Na), 474, 434.

Exact Mass Calc. (M+Na) for C$_{32}$H$_{36}$N$_2$O$_9$, 615.2319. found, 615.2299.

2,2-(Ethylenedioxy)diethylamine N,N'-{2,2-dimethyl-3,4-dioxo-4-{(2S)-2-[(1R)-1,3-diphenylpropyloxycarbonyl]-1-piperidinyl}butylcarbamate, (77)

A solution of (1R)-1,3-diphenyl-1-propyl-(2S)-1-[3,3-dimethyl-1,2-dioxo-4-(1-succinimidyloxycarbonyl)oxy]butyl-2-piperidinecarboxylate, 76 (75 mg, 0.13 mmol) and N,N-diisopropylethylamine (66.3 µL) in acetonitrile (4 mL) was treated with 2,2'-(ethylenedioxy)diethylamine (9.3 µL), and the mixture stirred at room temperature for 21 h. The solvent was removed and the residue chromatographed (silica-gel, hexanes-ethyl acetate 1:3 to 1:2 gradient) to give the title compound (20 mg) as a colorless oil.

$^1$H NMR (CDCl$_3$) d 7.10-755 (m, 20H), 5.48 (br dd, J=12.2, 6.1 Hz, 2H), 5.20-5.35 (br s, 2H), 5.09-5.18 (m, 2H), 4.22 (AB q, J$_{AB}$=10.6 Hz, 4H), 3.48-3.80 (m, 8H), 3.20-3.45 (m, 6H), 2.80-3.15 (m, 10H), 1.98-2.08 (m, 2H), 1.17-1.68 (m, 22H). $^{13}$C NMR (CDCl$_3$) d 205.3, 170.1, 166.9, 156.6, 137.6, 137.3, 129.7 (2C), 128.9, 128.8, 127.1, 127.0, 76.9, 70.6, 70.4, (69.9), (60.8), (56.9), 51.6, 47.3, (47.2), 44.0, 41.2, 40.7, 40.5, (40.2), (39.0), (28.1), 26.8, 25.2, (24.7), 22.3, (22.2), 21.8, (21.4), 21.0, (20.8), 14.6. MS(FAB$^+$/NaI) m/z 1125 (M+Na).

p-Xylylenediamine N,N'-{2,2-dimethyl-3,4-dioxo-4-{(2S)-2-[(1R)-1,3-diphenylpropyloxycarbonyl]-1-piperidinyl}butylcarbamate, (78)

A solution of p-xylylenediamine in dimethylformamide (0.1 mM, 0.5 mL) was added dropwise, over a 30 min-period, to a solution of 76 (66 mg, 0.11 mmol) and triethylamine (46 µL) in acetonitrile (1 mL). The mixture was then partitioned between ethyl acetate and water, and the organic layer was decanted, washed with water, dried over anhydrous sodium sulfate, and concentrated to a yellow oil. Column chromatography (silica-gel, hexanes-ethyl acetate 1:1) afforded the title compound (33 mg) as a colorless oil.

$^1$H NMR (C$_6$D$_6$) d 7.34-7.55 (m, 24H), 5.72-5.85 (m, 2H), 5.64-5.68 (m, 2H), 5.35-5.45 (m, 2H), 4.77 (AB q, J$_{AB}$=10.8 Hz, 4H), 4.46-4.57 (m, 4H), 3.64 (br d, J=12.2 Hz, 2H), 2.92-3.25 (m, 10H), 2.14 (br d, J=13.2 Hz, 2H), 1.20-1.75 (m, 22H). MS(FAB$^+$/NaI) m/z 1113 (M+Na).

Preparation of Bumped Monomers

Illustrative C-9 bumped monomers were prepared by the following scheme:

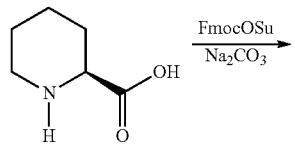

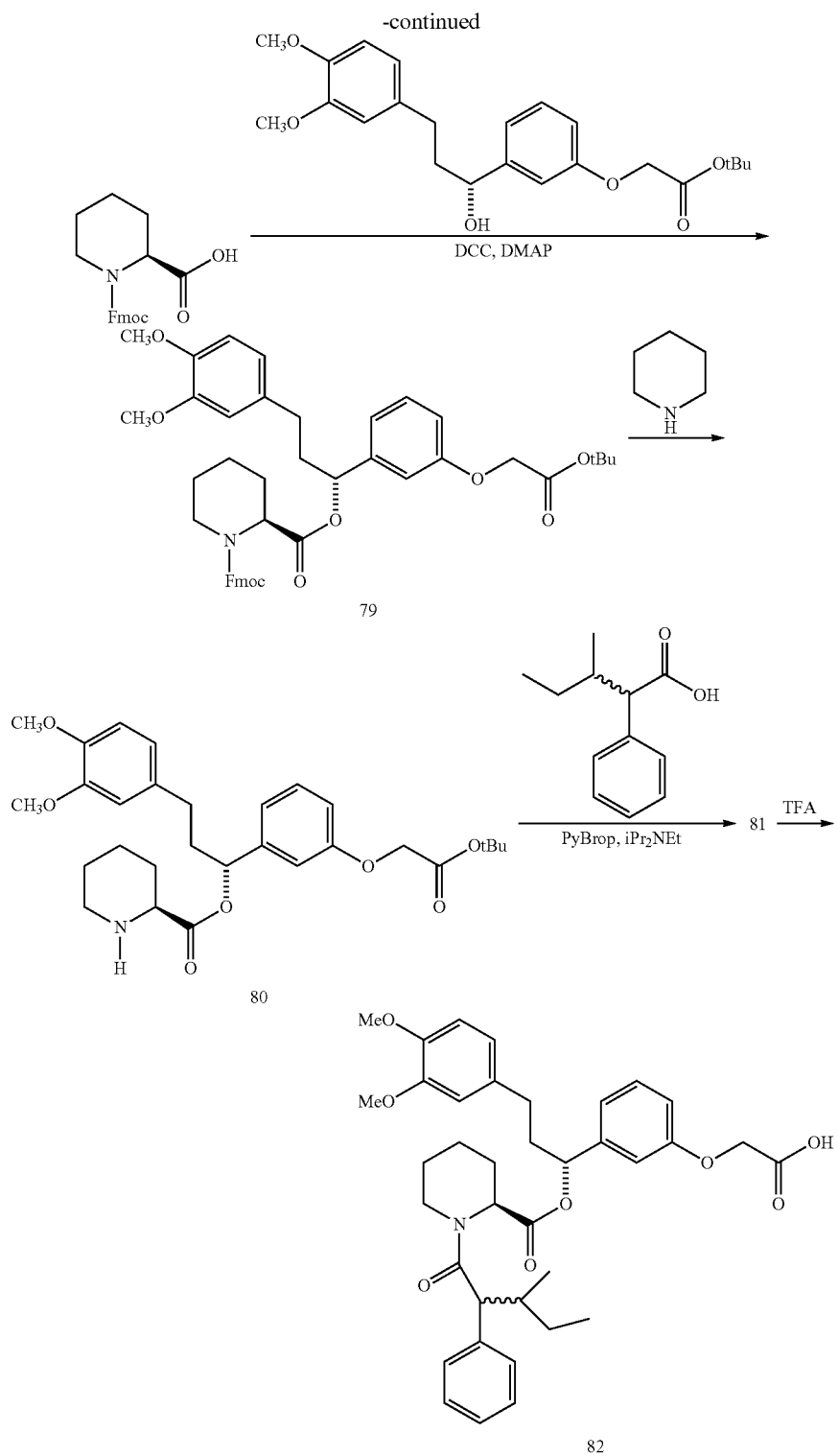

(1R)-3-(3,4-Dimethoxyphenyl)-1-[3-(t-butoxycarbonylmethoxy)phenyl]-1-propyl (2S)-1-(9-fluorenylmethoxycarbonyl)-2-piperidinecarboxylate (79)

A solution of (R) 1-(3-(tert-Butoxycarbonylmethoxy)phenyl)-3-(3,4-dimethoxyphenyl)propan-1-ol (13) (3.1 g, 7.7 mmol) in CH$_2$Cl$_2$ (40 mL) was treated with Fmoc pepicolic acid (3.0 g, 8.5 mmol) followed by 1,3-dicyclohexyl carbodiimide (DCC, 1.9 g, 9.2 mmol) and 4-(dimethylamino)pyridine (DMAP 560 mg, 4.6 mmol) under a nitrogen atmosphere. The resulting bright white suspension was allowed to stir overnight. The reaction mixture was then filtered, evaporated, and flash chromatographed (silica gel, 15% Æ 20% EtOAc/hexanes) to afford 4.7 g (83%) of a white foam: $^1$H NMR (CDCl$_3$, 300 MHz) 7.73 (m, 2H), 7.59 (t, J=6.6 Hz, 1H), 7.16-7.49 (m, 6H). 6.94 (d, J=7.6 Hz, 1H), 6.89 (s, 1H), 6.72-6.82 (m, 2H), 6.62 (m, 2H), 5.76 (br s, 1H), 5.02 (d, J=3.7 Hz, 1H), 4.25-4.49 (m, 5H), 4.07-4.14 (m, 1H), 3.83 (s, 6H), 3.14 (t, J=11.1 Hz, 1H), 2.46-2.54 (m, 2H), 2.16-2.33 (m, 2H), 2.00-2.07 (m, 1H), 1.68-1.78 (m, 4H), 1.46 (s, 9H), 1.39-1.56 (m, 1H); $^{13}$C NMR (CDCl$_3$, 75 MHz) 174.50, 171.33, 168.28, 158.48, 147.73, 144.30, 142.12, 133.90, 130.07, 128.07, 127.45, 125.48, 120.50, 120.35, 114.34, 113.66, 112.12, 111.74, 82.74, 76.82, 76.59, 68.20, 66.16, 56.32, 56.20, 47.63, 38.44, 31.98, 31.54, 28.42, 27.23, 25.18, 21.20.

(1R)-3-(3,4-Dimethoxyphenyl)-1-[3-(t-butoxycarbonylmethoxy)phenyl]-1-propyl (2S)-2-piperidinecarboxylate (80)

A solution of the above Fmoc protected compound (833 mg, 1.13 mmol) in CH$_2$Cl$_2$ (30 mL) was treated with piperidine (1.12 mL, 11.3 mmol) and the mixture was stirred at room temperature overnight. The reaction mixture was concentrated and flash chromatographed (silica gel, 50% Æ 100% EtOAc/hexanes) to afford 569 mg (98%) of the amine as a white foam: $^1$H NMR (CDCl$_3$, 300 MHz) (single enantiomer, mixture of rotamers) 7.28 (t, J=7.9 Hz, 1H), 6.98 (d, J=7.7 Hz, 1H), 6.93 (s, 1H), 6.84 (m, 2H), 6.71 (d, J=8.3 Hz, 1H), 6.69 (s; 1H), 5.77 (dd, J=6.3, 6.8 Hz, 1H), 4.55 (s, 2H), 3.91 (s, 6H), 3.42 (m, 1H), 3.33 (s, 1H), 3.01 (m, 1H), 239-2.63 (m, 3H), 2.11-2.27 (m, 1H), 2.05-2.09 (m, 1H), 1.92 (m, 1H), 1.54 (s, 9H), 1.54-1.74 (m, 4H); $^{13}$C NMR (CDCl$_3$, 75 MHz) 173.42, 168.29, 158.34, 149.20, 147.64, 142.54, 134.06, 129.92, 120.49, 120.19, 114.11, 113.54, 111.99, 111.60, 82.74, 75.21, 66.05, 61.45, 56.30, 56.21, 48.57, 38.55, 31.63, 29.41, 28.44, 25.70, 22.56. MS(FAB): (M+Na)$^+$ 536.

(1R)-3-(3,4-Dimethoxyphenyl)-1-[3-(t-butoxycarbonylmethoxy)phenyl]-1-propyl (2S)-1-(1-oxo-2-phenyl-3-methyl-pentyl)-2-piperidinecarboxylate (81)

A solution of the above amine (484 mg, 0.94 mmol) in CH$_2$Cl$_2$ (10 mL) was treated with 3-methyl-2-phenyl valeric acid (362 mg, 1.9 mmol) followed by PyBroP (878 mg, 1.9 mmol) and diisopropylethyl amine (819 mL, 4.7 mmol) under a nitrogen atmosphere. The resulting solution was allowed to stir overnight. The reaction mixture was concentrated and flash chromatographed (silica gel, 10% Æ 33% EtOAc/hexanes) to afford 380 mg (55%) of a white foam: $^1$H NMR (CDCl$_3$, 300 MHz) (single enantiomer, mixture of rotamers) 7.18-7.35 (m, 6H), 6.57-7.04 (m, 6H), 5.76-5.80 (m, 1H), 5.52-5.57 (m, 1H), 4.54 (s, 2H), 3.87 (s, 6H), 3.50-3.57 (m, 1H), 3.10 (t, J=13.3 Hz, 1H), 2.04-2.71 (m, 5H), 0.61-1.85 (m, 12H), 1.49 (s, 9H). HRMS(FAB): (M+Na)$^+$ calcd: 710.3669. found: 710.3664.

(1R)-3-(3,4-Dimethoxyphenyl)-1-[3-(hydroxycarbonylmethoxy)phenyl]-1-propyl (2S)-1-(1-oxo-2-phenyl-3-methyl-pentyl)-2-piperidinecarboxylate (82)

A solution of the above t-butyl ester (331 mg, 0.48 mmol) in CH$_2$Cl$_2$ (4 mL) was treated with trifluoroacetic acid (0.74 mL, 9.6 mmol) and the mixture was stirred at room temperature for 2 hours. The reaction mixture was diluted with toluene (50 mL) and concentrated and flash chromatographed (silica gel, 100% EtOAc) to afford 300 mg (100%) of the acid as a white solid: HRMS(FAB): (M+Na)$^+$ calcd: 654.3043. found: 654.3055.

Additional Synthetic Examples

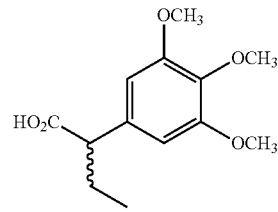 [SMILES: CCC(C(=O)O)c1cc(OC)c(OC)c(OC)c1]

2R/S-(3,4,5-Trimethoxyphenyl)butyric acid

A solution of 3,4,5-trimethoxyphenylacetic acid (32.8 g, 145 mmol) in THF (200 mL) at 0° C. was treated with a 1N solution of sodium bis(trimethylsilyl)amide (325 mL, 325 mmol) followed 15 min later by addition of iodoethane (12.8 mL, 160 mmol). The reaction mixture was allowed to warm to room temperature and stir for 12 h after which time the reaction mixture was diluted with EtOAc (1.5 L) and poured onto a mixture of ice (500 g) and acidified to a pH of 3 by careful addition of 1N aqueous HCl solution. The aqueous phase was extracted with EtOAc (500 mL) which were then combined and washed with water (250 mL) followed by a saturated aqueous NaCl solution (100 mL). The organic extract was then dried over MgSO$_4$, filtered, evaporated, and chromatographed (silica gel, 2.5% HOAc/48.75% EtOAc/48.75% hexanes) to afford product (33.92 g, 92%): $^1$H NMR (CDCl$_3$, 300 MHz) 6.53 (s, 2H), 3.85 (s, 6H), 3.83 (s, 3 H), 3.38 (t, J=7.6 Hz, 1H), 2.13-2.04 (m, 1H), 1.84-1.75 (m, 1H), 0.93 (t, J=7.4 Hz, 3H); $^{13}$C NMR (CDCl$_3$, 75 MHz) 179.9, 153.7, 137.8, 134.3, 105.6, 61.2, 56.6, 53.9, 26.8, 12.5.

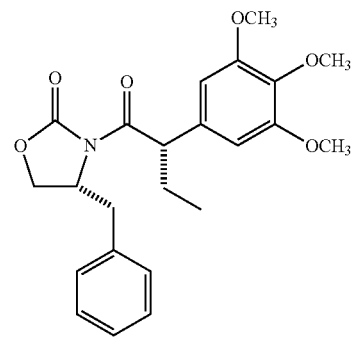 [SMILES: CC[C@H](C(=O)N1C(=O)OC[C@H]1Cc1ccccc1)c1cc(OC)c(OC)c(OC)c1]

(4R-Benzyl-2-oxazolidinonyl)
2S-(3,4,5-Trimethoxyphenyl)butyramide

A solution of 2R/S-(3,4,5-Trimethoxyphenyl)butyric acid (33.9 g, 133 mmol) in CH$_2$Cl$_2$ (350 mL) at room temperature was treated with thionyl chloride (50.0 mL, 685 mmol) and allowed to stir for 16 h. The reaction mixture was then concentrated and dissolved in THF (250 mL) and added to a solution of the sodium oxazolidinonide prepared by addition of n-BuLi (108 mL of 1.6N hexanes solution, 172.8 mmol) to a THF (600 mL) solution of R-4-benzyl-2-oxazolidinone (29.46 g, 166.3 mmol) at −78° C. which was allowed to warm to 0° C. and stir for 30 min. After addition of the chloride, the reaction mixture was allowed to warm to room temperature and stir for 1.5 h after which time was poured onto a saturated aqueous NH₄Cl solution (1 L) and the resulting slurry extracted with CH₂Cl₂ (3×1 L). The combined organic extracts were washed with a 1N aqueous NaOH solution (1 L) followed by water (1 L) and a saturated aqueous NaCl solution (750 mL). The organic extract was then dried over MgSO₄, filtered, evaporated, and chromatographed (silica gel, 5% EtOAc/5% hexanes/90% CH₂Cl₂) to afford product (12.65 g, 23%) as the less polar diastereomer.

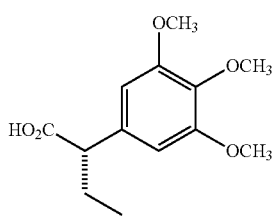

2S-(3,4,5-Trimethoxyphenyl)butyric acid

A solution of (4R-benzyl-2-oxazolidinonyl) 2S-(3,4,5-Trimethoxyphenyl)butyrimide (12.6 g, 30.6 mmol) in THF (75 mL) at 0° C. was slowly added to a slurry containing LiOH monohydrate (12.84, 306 mmol) and hydrogen peroxide (34.7 mL of a 30% aqueous solution, 306 mmol) in a THF/water (2:1) solution at 0° C. The reaction mixture was allowed to stir for 30 min after which time EtOAC (1 L) was added and the solution slowly acidified to a pH of 3 with a 1N aqueous solution of HCl. The organic phase was washed with water (500 mL) followed by a saturated aqueous NaCl solution (250 mL), then dried over MgSO₄, filtered, evaporated, and chromatographed (silica gel, 2.5% HOAc/48.75% EtOAc/48.75% hexanes) to afford product (5.99 g, 77%).

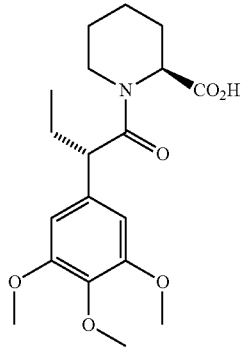 [SMILES: CC[C@H](C(=O)N1CCCC[C@H]1C(=O)O)c1cc(OC)c(OC)c(OC)c1]

N-2S-(3,4,5-Trimethoxyphenyl)butyryl-2S-piperidinecarboxylic acid

A solution of 2S-(3,4,5-trimethoxyphenyl)butyric acid (5.99 g, 23.6 mmol) in CH₂Cl₂ (175 mL) at room temperature was treated with methyl 2S-piperidinecarboxylate (4.66 g, 26 mmol) followed by triethylamine (10.9 mL, 78 mmol) and 2-chloro-1-methylpyridinium iodide (8.95 g 35 mmol). The reaction mixture was stirred for 2 h after which time it was concentrated and chromatographed (silica gel, 50% EtOAc/hexanes) to afford product (6.72 g, 75%).

A solution of the methyl ester (7.39 g, 19.5 mmol) in a MeOH/water solution (1.5 L/15 mL) at room temperature was treated with LiOH monohydrate (8.20 g, 195.4 mmol). The reaction mixture was stirred for 4 h, diluted with EtOAc (1 L) then poured onto a mixture of ice (200 g) and a 1N aqueous solution of HCl (225 mL). The organic portion was then washed with water (300 mL) followed by a saturated aqueous NaCl solution (250 mL), then dried over MgSO₄, filtered, and evaporated to a powder which was recrystallized from EtOAc to afford product (6.42 g, 90%) as a white crystalline solid: ¹H NMR (CDCl₃, 300 MHz) 8.17 (br s, 1H), 6.43 (s, 2H), 5.36 (d, J=3.9 Hz, 1H), 4.70 (d, J=5.4 Hz, 1H), 3.84-3.81 (m, 9H), 3.58 (t, J=6.9 Hz, 1H), 2.85 (t, J=12.0 Hz, 1H), 2.27 (t, J=13.5 Hz, 1H), 2.12-2.05 (m, 1H), 1.78-1.52 (m, 4H), 1.48-1.30 (m, 2H), 0.92 (t, J=7.3 Hz, 3H); ¹³C NMR (CDCl₃, 75 MHz) 174.4, 172.4, 152.1, 135.6, 133.9, 103.7, 59.6, 55.1, 51.0, 49.9, 42.4, 42.4, 27.1, 25.1, 23.9, 19.5, 11.3; MS(ES+): (M+H)⁺ 366; (ES−): (M−H)⁻ 364.

AP 1867

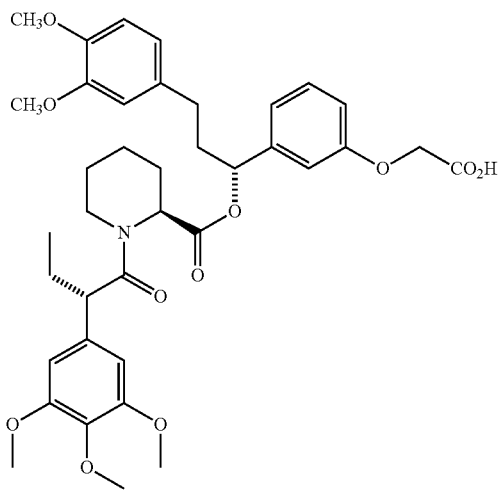

A solution of (R)-1-(3-(tert-butoxycarbonylmethoxy)phenyl)-3-(3,4-dimethoxyphenyl) propan-1-ol (13) (220 mg, 0.547 mmol) in CH₂Cl₂ (0.5 mL) at 0° C. was treated with (2S)-1-((2S)-(3,4,5-trimethoxyphenyl)butyryl)-2-piperidinecarboxylic acid (210 mg, 0.574 mmol) followed by 4-(dimethylamino)-pyridine (2 mg) and 1,3-dicyclohexylcarbodiimide (113 mg, 0.574 mmol). The resulting suspension was allowed to warm to room temperature and stir 16 h after which time it was diluted with EtOAc (3 mL) and filtered through a plug of Celite. The evaporated residue was chromatographed (silica gel, 40% Æ 50% EtOAc/hexanes) to afford (1R)-1-(3-(tert-butoxycarbonylmethoxy)phenyl)-3-(3,4-dimethoxyphenyl)propan-1-yl (2S)-1-((2S)-(3,4,5-trimethoxyphenyl)butyryl)-2-piperidine carboxylate (295 mg, 72%) as a colorless foam: TLC (EtOAc/hexanes, 2:3) Rf=0.20; MS(ES+): (M+H)⁺ 750, (M+Na)⁺ 772.

A solution of the above tert-butyl ester (250 mg, 0.362 mmol) in CH₂Cl₂ (10.0 mL) was cooled to 0° C. and treated with a steam of hydrogen chloride for 10 min. The reaction mixture was allowed to warm to room temperature and stir for 2 h after this time the reaction was evaporated for a solid white foam (245 mg, 90%): MS(ES+): (M+NH₄)⁺ 711, (M+Na)⁺ 716; (ES−): (M−H)⁻ 692.

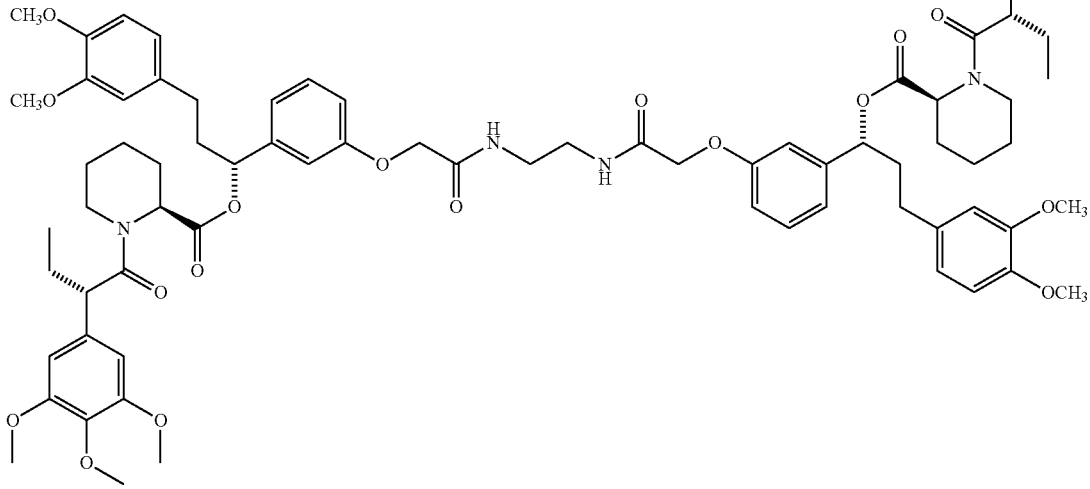

AP1903

A solution of AP1867 (8.2 g, 11.82 mmol) in CH$_2$Cl$_2$ (100 mL) at 0° C. was treated sequentially with benzotriazol-1-yloxytris-(dimethylamino)phosphonium hexafluorophosphate (7.3 g, 14.0 mmol), diisopropylethylamine (5.50 mL, 31.6 mmol), and ethylenediamine (395 uL, 5.91 mmol). The reaction mixture was allowed to stir at room temperature for 16 h after which time was diluted with EtOAc (150 mL) and washed with water (3×50 mL) followed by a saturated aqueous NaCl solution (25 mL). The organic solution was dried over MgSO4, filtered, and evaporated to afford a residue which was chromatographed (silica gel, EtOAc) to afford product. The product was then dissolved in MeOH (10 mL) and water added until the solution became turbid. Freezing of the aqueous methanolic solution (dry ice/acetone bath) followed by lyophilization at 100 mtorr afforded AP1903 (5.49 g, 61%) as a white powder: MS(ES+): (M+Na)$^+$ 1434; (ES−): (M−H)$^−$ 1410.

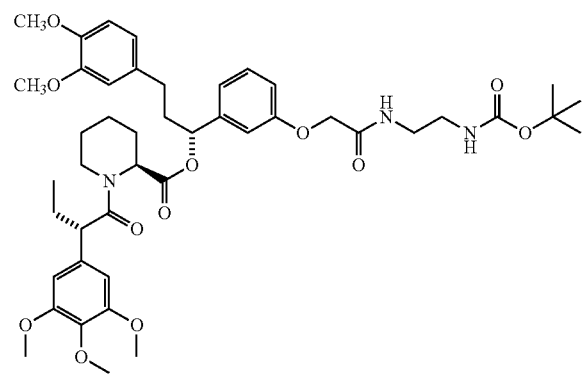

The acid AP 1867 (245 mg, 0.353 mmol) was dissolved in CH$_2$Cl$_2$ (1.0 mL), cooled to 0° C., and treated 4-(dimethylamino)-pyridine (2 mg) followed by 1,3-dicyclohexylcarbodiimide (77 mg, 0.371 mmol). The reaction mixture was allowed to stir for 5 min after which time tert-butyl N-(2-aminoethyl)-carbamate (61 uL, 0388 mmol) was added. The resulting suspension was allowed to stir for 16 h after which time it was diluted with EtOAc (3 mL), filtered through a plug of Celite, evaporated, and chromatographed (silica gel, EtOAc) to afford product (266 mg, 90%) as a colorless foam: TLC (EtOAc) Rf=036; MS(ES+): (M+H)$^+$ 836, (M+Na)$^+$ 858.

A solution of the above tert-butyl carbamate (266 mg, 0318 mmol) in CH$_2$Cl$_2$ (10.0 mL) was cooled to 0° C. and treated with a steam of hydrogen chloride for 10 min. The reaction mixture was allowed to warm to room temperature and stir for 2 h after which time was evaporated to afford a solid white foam which was partitioned between CH$_2$Cl$_2$ (15 mL) and a saturated aqueous NaHCO$_3$ solution (10 mL). The layers were separated and the aqueous layer washed with $CH_2Cl_2$ (5 mL) and the combined organic extracts washed with a saturated aqueous NaCl solution (10 mL) then dried over $Na_2SO_4$, filtered, and evaporated to afford product (203 mg, 87%) as a colorless sticky foam: MS(ES+): $(M+H)^+$ 736.

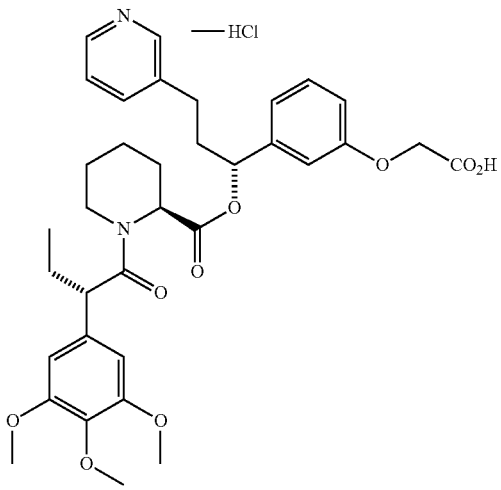

(1R)-1-(3-(Carboxymethoxy)phenyl)-3-(3-pyridyl)-1-propyl (2S)-1-((2S)-(3,4,5-trimethoxyphenyl)butyryl)-2-piperidinecarboxylate hydrochloride (AP14252)

A solution of (R)-1-(3-(tert-butoxycarbonylmethoxy)phenyl)-3-(3-pyridyl)propan-1-ol (21) (179 mg, 0.521 mmol) in $CH_2Cl_2$ (0.5 mL) at 0° C. was treated with (2S)-1-((2S)-(3,4,5-trimethoxyphenyl)butyryl)-2-piperidinecarboxylic acid (200 mg, 0.547 mmol) followed by 4-(dimethylamino)-pyridine (2 mg) and 1,3-dicyclohexylcarbodiimide (113 mg, 0.547 mmol). The resulting bright yellow suspension was allowed to warm to room temperature and stir for 16 h after which time it was diluted with EtOAc (3 mL) and filtered through a plug of Celite. The evaporated residue was chromatographed (silica gel, EtOAc) to afford product (303 mg, 84%) as a colorless foam: TLC (EtOAc) Rf=0.44; IR (neat) 2940, 1750, 1640, 1590, 1455, 1240, 1155 $cm^{-1}$; MS(ES+): $(M+Na)^+$ 691.

A solution of the above tert-butyl ester (250 mg, 0.362 mmol) in $CH_2Cl_2$ (10.0 mL) was cooled to ° C. and treated with a steam of hydrogen chloride for 10 min. The reaction mixture was allowed to warm to room temperature and stir for 2 h. After this time the reaction was evaporated for a solid white foam: MS(ES+): $(M+H)^+$ 635; (ES−): $(M-H)^-$ 633.

AP14290

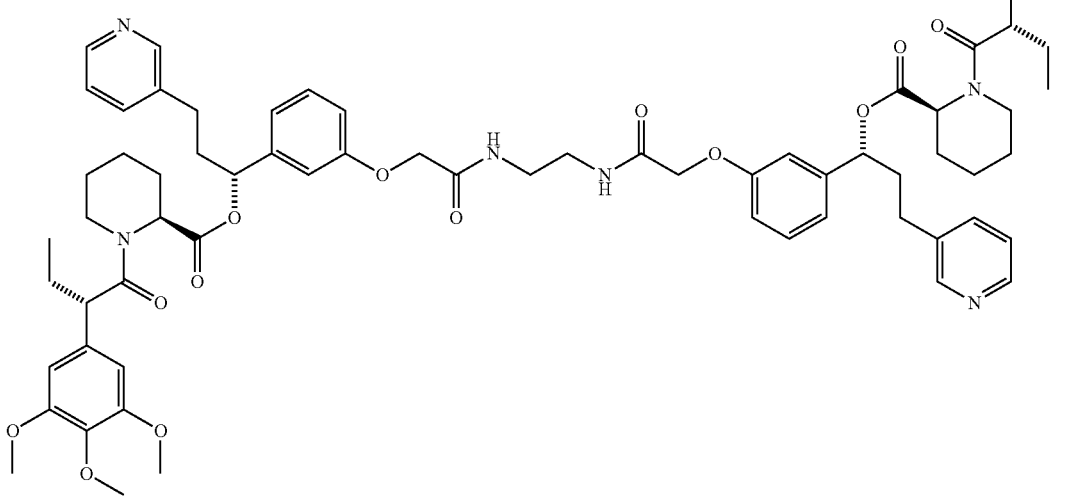

The acid hydrochloride AP14252 was dissolved in $CH_2Cl_2$ (1.0 mL), cooled to 0° C., and treated with triethylamine (48 uL, 0.362 mmol), 4-(dimethylamino)-pyridine (2 mg), and 1,3-dicyclohexylcarbodiimide (90 mg, 0.434 mmol). The reaction mixture was allowed to stir for 5 mm after which time a $CH_2Cl_2$ solution (100 uL) containing ethylenediamine (9.7 uL, 0.145 mmol) was added. The resulting suspension was allowed to warm to room temperature and stir for 16 h after which time it was diluted with EtOAc (3 mL), filtered through a plug of Celite, evaporated, and chromatographed (silica gel, 2"×0.5" column, 10% MeOH/EtOAc) to afford product (102 mg, 54% from tert-butyl ester) as a colorless foam: TLC (MeOH/EtOAc, 5:95) Rf=0.28; IR (neat) 3345, 2940, 1740, 1680, 1650, 1540, 1505, 1455, 1425, 1245, 1130, 1015 cm$^{-1}$; MS(ES+): (M+H)$^+$ 1293.

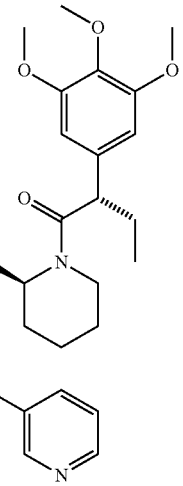

The acid (1R)-1-(3-(carboxymethoxy)phenyl)-3-(3-pyridyl)-1-propyl (2S)-1-(2S)-(3,4,5-trimethoxyphenyl)butyryl)-2-piperidinecarboxylate hydrochloride (AP14252) (28.5 mg, 0.0425 mmol) was dissolved in CH$_2$Cl$_2$ (0.5 mL), cooled to 0° C., and treated with a CH$_2$Cl$_2$ solution (100 uL) containing triethylamine (5.6 uL, 0.0425 mmol) followed by 4-(dimethylamino)-pyridine (catalytic amount) and 1,3-dicyclohexylcarbodiimide (9.1 mg, 0.0442 mmol). The reaction mixture was allowed to stir for 5 min after which time the solid amine (25 mg, 0.034 mmol) was added. The resulting suspension was allowed to warm to room temperature and stir for 16 h after which time was diluted with EtOAc (3 mL), filtered through a plug of Celite, evaporated, and chromatographed (silica gel, 5 Æ 10% MeOH/EtOAc) to afford product (28 mg, 61%) as a colorless foam: TLC (MeOH/CHCl$_3$, 1:9) Rf=0.28; IR (neat) 3445, 2940, 1740, 1675, 1645, 1590, 1515, 1455, 1420, 1240, 1130, 1015 cm$^{-1}$% MS(ES+): (M+H)$^+$ 1352.

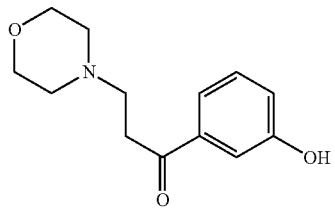 [SMILES: O=C(CCN1CCOCC1)c1cccc(O)c1]

1-(3-Hydroxyphenyl)-3-(1-morpholino)propan-1-one

A solution of morpholine (1.0 mL, 11.5 mmol) in EtOH (10 mL) was treated with 3-hydroxyacetaphenone (1.56 g, 11.5 mmol) and paraformaldehyde (340 mg, 11.5 mmol) followed by acetic acid (1.3 mL, 23 mmol). The resulting mixture was heated at reflux for 16 h then cooled and evaporated. The residue was then diluted with a 5% aqueous HCl solution (10 mL) then washed with diethyl ether (2×10 mL) followed by neutralization by addition of solid NaHCO$_3$. The neutralized aqueous solution was extracted with diethyl ether (2×10 mL) which was then dried over MgSO$_4$, filtered, and concentrated to a residue. The residue was chromatographed (silica gel, 5% MeOH/CH$_2$Cl$_2$) to afford product (680 mg, 25%) as a brownish oil: TLC (MeOH/CH$_2$Cl$_2$, 5:95) Rf=0.22; IR (neat) 2960, 2855, 1685, 1585, 1450, 1360, 1275, 1115, 995, 865 cm$^{-1}$; $^1$H NMR (CDCl$_3$, 300 MHz) 7.48 (d, J=7.8 Hz, 1H), 7.42 (t, J=2.0 Hz, 1H), 7.32 (t, J=7.9 Hz, 1H), 7.05 (m, 1H), 3.75 (t, J=4.7 Hz, 4H), 3.25 (t, J=7.3 Hz, 2H), 2.87 (t, J=7.3 Hz, 2H), 2.57 (t, J=4.5 Hz, 4H); MS(ES−): (M−H)$^-$ 234.

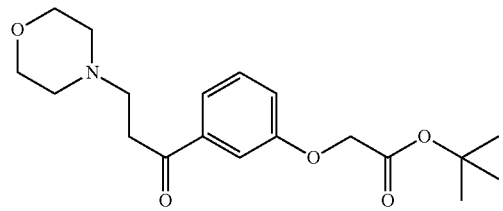 [SMILES: CC(C)(C)OC(=O)COc1cccc(C(=O)CCN2CCOCC2)c1]

1-(3-(tert-Butoxycarbonylmethoxy)phenyl)-3-(1-morpholino)propan-1-one

A 60% mineral oil suspension of NaH (1.97 g, 49 mmol) in anhydrous DMF (20 mL) was cooled to 0° C. in an ice bath and a DMF solution (10 mL) of 1-(3-Hydroxyphenyl)-3-(1-morpholino)propan-1-one (10.5 g, 45 mmol) added. The resulting yellow solution was stirred for 15 min followed by addition of tert-butylbromoacetate (7.26 mL, 49 mmol). The reaction mixture was stirred at 0° C. for 15 min, allowed to warm to room temperature, and partitioned between EtOAc (50 mL) and water (150 mL). The aqueous portion was washed with EtOAc (2×50 mL) and the combined organic extracts washed with a saturated aqueous NaCl solution (2×50 mL), dried over Na$_2$SO$_4$, filtered, evaporated, and flash chromatographed (silica gel, 1% MeOH/EtOAc) to afford product (105 g, 67%) as an oil: TLC (MeOH/CH$_2$Cl$_2$, 5:95) Rf=0.39; IR (neat) 2975, 1750, 1685, 1585, 1445, 1370, 1225, 1155, 1120 cm$^{-1}$; $^1$H NMR (CDCl$_3$, 300 MHz) 7.57 (d, J=7.7 Hz, 1H), 7.46 (s, 1H), 7.38 (t, J=8.0 Hz, 1H), 7.13 (d, J=8.2 Hz, 1H), 4.57 (s, 2H), 3.71 (t, J=4.7 Hz, 4H), 3.15 (t, J=7.3 Hz, 2H), 2.82 (t, J=7.3 Hz, 2H), 2.50 (t, J=4.6 Hz, 4H), 1.49 (s, 9H); MS(ES+): (M+H)$^+$ 350.

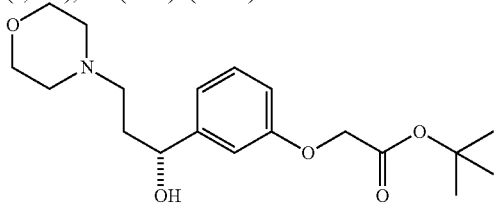 [SMILES: CC(C)(C)OC(=O)COc1cccc([C@H](O)CCN2CCOCC2)c1]

1R-(3-(tert-Butoxycarbonylmethoxy)phenyl)-3-(1-morpholino)propan-1-ol

A solution of 1-(3-(tert-butoxycarbonylmethoxy)phenyl)-3-(1-morpholino)propan-1-one (1.0 g, 2.86 mmol) in THF (5 mL) at −78° C. was treated with a solution of (+)-b-chlorodiisopinocamphenylborane (2.76 g, 8.59 mmol) in THF (10 mL) at −78° C. The resulting mixture was allowed to stand in a −20° C. freezer for 48 h after which time the mixture was evaporated and treated with diethyl ether (40 mL) followed by diethanolamine (5 mL). The viscous mixture was allowed to stir at room temperature for 4 h followed by filtration through a pad of Celite with the aid of ethyl acetate. The cloudy filtrate was evaporated and flash chromatographed (silica gel, 5% MeOH/EtOAc) to afford 270 mg (27%) of an oil that solidified to a waxy solid on standing: TLC (MeOH/CH$_2$Cl$_2$, 5:95) Rf=0.33; IR (neat) 2955, 1750, 1585, 1455, 1370, 1225, 1155, 1120, 1075 cm$^{-1}$; $^1$H NMR (CDCl$_3$, 300 MHz) 7.57 (d, J=7.9 Hz, 1H), 6.97 (m, 2H), 6.78 (d, J=8.1 Hz, 1H), 4.91 (t, J=5.7 Hz, 1H), 452 (s, 2H), 3.75 (t, J=4.6 Hz, 4H), 2.70-2.40 (m, 6H), 1.85 (m, 2H), 1.49 (s, 9H); MS(ES+): (M+H)$^+$ 352.

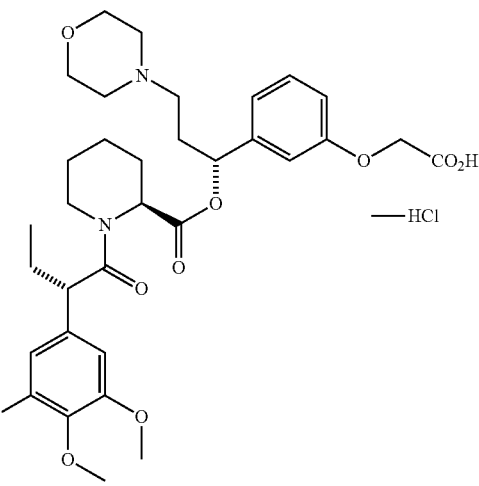

(1R)-1-(3-(carboxymethoxy)phenyl)-3-(morpholino)-1-propyl (2S)-1-((2S)-(3,4,5-trimethoxyphenyl)butyryl)-2-piperidine carboxylate (AP14246)

A solution of (R)-1-(3-(tert-butoxycarbonylmethoxy)phenyl)-3-(1-morpholino)propan-1-ol (96 mg, 0.274 mmol) in CH$_2$Cl$_2$ (2.0 mL) at 0° C. was treated with (2S)-1-((2S)-(3,4,5-trimethoxyphenyl)butyryl)-2-piperidinecarboxylic acid (100 mg, 0.274 mmol) followed by 4-(dimethylamino)-pyridine (2 mg) and 1,3-dicyclohexylcarbodiimide (59 mg, 0.287 mmol). The resulting suspension was allowed to warm to room temperature and stir 16 h after which time was diluted with EtOAc (5 mL) and filtered through a plug of Celite. The evaporated residue was chromatographed (silica gel, 3% MeOH/EtOAc) to afford product (154 mg, 81%) as a colorless foam: TLC (MeOH/CHCl$_3$, 5:95) Rf=0.28; IR (neat) 2940, 1750, 1645, 1590, 1455, 1245, 1155, 1130 cm$^{-1}$; MS(ES+): (M+H)$^+$ 699.

A solution of the above tert-butyl ester in CH$_2$Cl$_2$ (10.0 mL) was cooled to 0° C. and treated with a steam of hydrogen chloride for 10 min. The reaction mixture was allowed to warm to room temperature and stir for 2 h, after this time the reaction was evaporated for a solid white foam: MS(ES+): (M+H)$^+$ 643, (ES−): (M−H)$^-$ 641.       AP14291

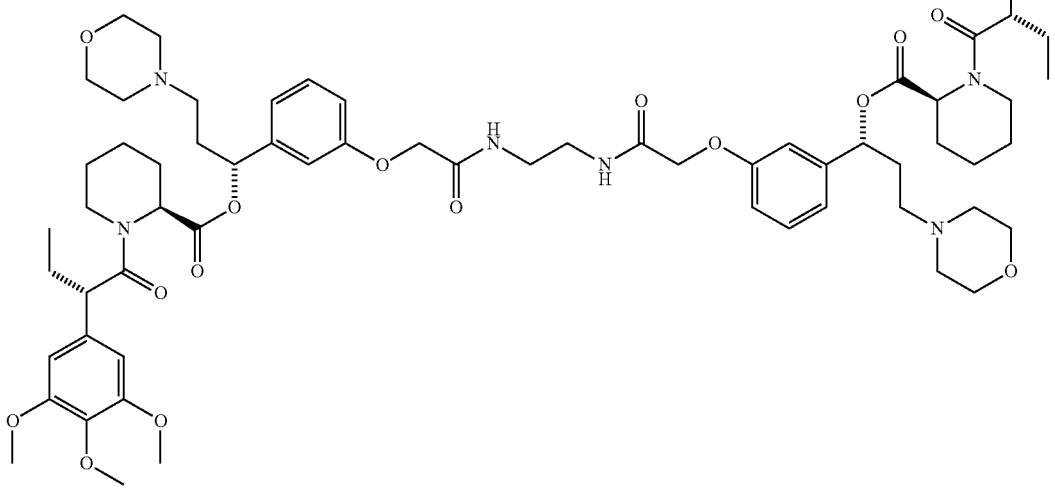

The acid hydrochloride AP14246 (50.6 mg 0.0745 mmol) was dissolved in $CH_2Cl_2$ (0.25 mL), cooled to 0° C., and treated with a $CH_2Cl_2$ solution (100 uL) containing triethylamine (9.8 uL, 0.0745 mmol) followed by 4-(dimethylamino)-pyridine (catalytic amount) and 1,3-dicyclohexylcarbodiimide (18.4 mg, 0.0894 mmol). The reaction mixture was allowed to stir for 5 min after which time a $CH_2Cl_2$ solution (100 uL) containing ethylenediamine (2.0 uL, 0.0298 mmol) was added. The resulting suspension was allowed to warm to room temperature then diluted with EtOAc (3 mL), filtered through a plug of Celite, evaporated, and chromatographed (silica gel, 2"×0.5" column, 20% MeOH/EtOAc) to afford product (25 mg, 64%) as a colorless foam: TLC (MeOH/EtOAc, 1:4) Rf=0.19; IR (neat) 2940, 1730, 1680, 1650, 1590, 1455, 1245, 1130 $cm^{-1}$; MS(ES+): $(M+H)^+$ 1310.

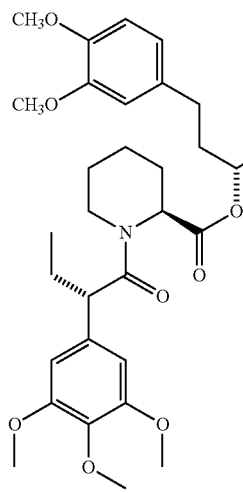

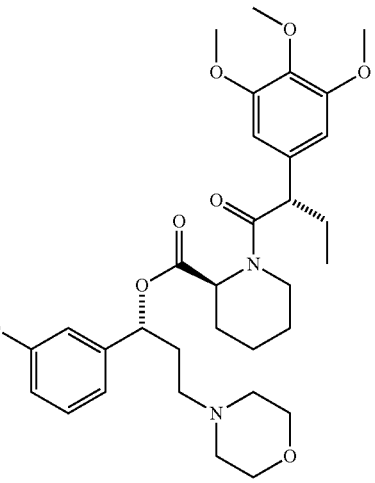

AP14272

The acid hydrochloride, (1R)-1-(3-(carboxymethoxy)phenyl)-3-(morpholino)-1-propyl (2S)-1-((2S)-(3,4,5-trimethoxyphenyl)butyryl)-2-piperidinecarboxylate hydrochloride (AP14246), (100 mg, 0.147 mmol) was dissolved in $CH_2Cl_2$ (0.5 mL), cooled to 0° C., and treated with triethylamine (20 uL, 0.147 mmol) followed by 4-(dimethylamino)-pyridine (2 mg) and 1,3-dicyclohexylcarbodiimide (33 mg, 0.162 mmol). The reaction mixture was allowed to stir for 5 min after which time the solid amine was added (108 mg, 0.147 mmol) was added. The resulting suspension was allowed to stir overnight (16 h) then diluted with EtOAc (3 mL), filtered through a plug of Celite, evaporated, and chromatographed (silica gel, 5 Æ 10% MeOH/EtOAc) to afford product (170 mg, 85%) as a colorless foam: TLC (MeOH/EtOAc, 5:95) Rf=0.19; IR (neat) 3355, 2940, 1740, 1670, 1645, 1590, 1515, 1240, 1130, 1020 $cm^{-1}$; MS(ES+): $(M+H)^+$ 1361.

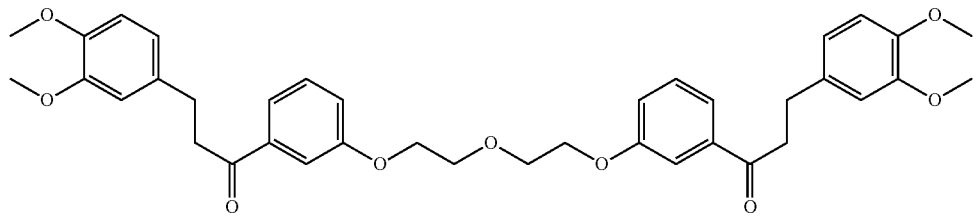

2-[1-(3-(3,4-Dimethoxyphenyl)propan-1-one)-3'-phenoxy]ethyl ether

A 60% mineral oil suspension of NaH (1.40 g, 3.49 mmol) in anhydrous DMF (25 mL) was cooled to 0° C. in an ice bath and solid 3-(3,4-dimethoxyphenyl)-1-(3-hydroxyphenyl)propan-1-one (10 g, 3.49 mmol) added portionwise. The resulting yellow solution was stirred for 15 min followed by addition of 2-iodoethyl ether (5.42 g, 1.02 mmol). The reaction mixture was stirred at 0° C. for 15 min and allowed to warm to room temperature and stir for 16 h. After this time the reaction mixture was partitioned between EtOAc (200 mL) and water (250 mL). The organic layer was washed with a saturated aqueous NaCl solution (3×200 mL), dried over MgSO$_4$, filtered, evaporated, and flash chromatographed (silica gel, 40 Æ 50 Æ 80% EtOAc/hexanes) to afford product (6.76 g, 63%) of a clear yellowish oil: TLC (ethyl acetate/hexanes, 1:1) Rf=028; IR (neat) 2935, 1685, 1515, 1460, 1260, 1140, 1030 cm$^{-1}$; $^1$H NMR (CDCl$_3$, 300 MHz) 7.54-7.36 (m, 2H), 7.33 (t, J=7.9 Hz, 1H), 7.11 (d, J=8.1 Hz, 1H), 6.81-6.77 (m, 3H), 4.19 (t, J=4.1 Hz, 2H), 3.94 (t, J=4.4 Hz, 2H), 3.86 (s, 3H), 3.84 (s, 3H), 2.45 (t, J=7.3 Hz, 2H), 3.00 (t, J=7.5 Hz, 2H); $^{13}$C NMR (CDCl$_3$, 75 MHz) 199.6, 159.6, 149.5, 148.0, 138.8, 134.5, 130.1, 121.4, 120.8, 120.6, 113.8, 112.5, 112.0, 70.4, 68.3, 56.5, 56.4, 41.3, 30.4; MS(ES+): (M+H)$^+$ 643, (M+Na)$^+$ 665.

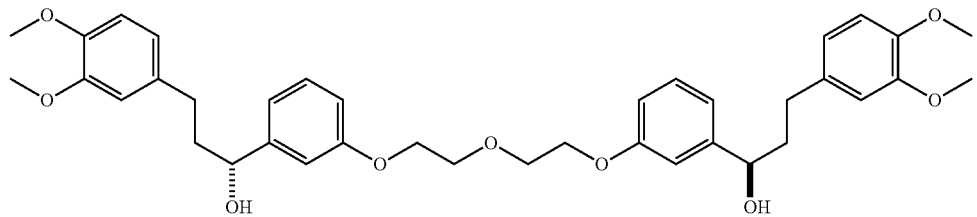

2-[1-(3-(3,4-Dimethoxyphenyl)propan-1-ol)-3'-phenoxy]ethyl ether

A solution of 2-[1-(3-(3,4-Dimethoxyphenyl)propan-1-one)-3'-phenoxy]ethyl ether (2.70 g, 4.20 mmol) in THF (10 mL) at −20° C. was treated with a solution of (+)-b-chlorodiisopinocamphenylborane (4.04 g, 12.6 mmol) in THF (10 mL) at −20° C. The resulting mixture was allowed to stand in a −20° C. freezer for 72 h after which time the mixture was evaporated and treated with diethyl ether (300 mL) followed by diethanolamine (10 mL). The viscous mixture was allowed to stir at room temperature for 6 h followed by filtration through a pad of Celite with the aid of ethyl acetate. The cloudy filtrate was evaporated and flash chromatographed (silica gel, 50 Æ 80 Æ 100% EtOAc/hexanes) to afford product (1.25 g, 46%) as a solid material: TLC (EtOAc/hexanes, 3:1) Rf=0.22; IR (neat) 3505, 2935, 1590, 1515, 1451, 1260, 1140, 1030 cm$^{-1}$; $^1$H NMR (CDCl$_3$, 300 MHz) 7.26-7.20 (m, 1H), 6.92-6.70 (m, 6H), 4.64-2.60 (m, 1 H), 4.15 (t, J=4.4 Hz, 2H), 3.92 (t, J=5.0 Hz, 2H), 3.84 (s, 6H), 2.73-2.54 (m, 2H), 2.13-1.91 (m, 2 H); $^{13}$C NMR (CDCl$_3$, 75 MHz) 159.4, 149.3, 147.6, 146.8, 134.8, 129.9, 120.6, 118.9, 114.0, 112.8, 112.3, 111.8, 74.1, 70.4, 67.9, 56.3, 56.2, 41.0, 32.0; MS(ES+): (M+NH$_4$)$^+$ 664, (M+Na)$^+$ 669.

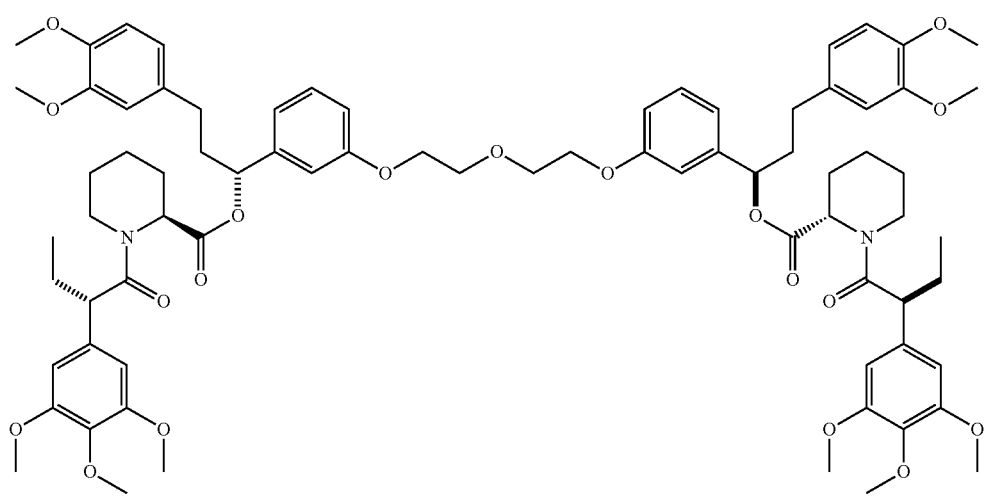

A solution of 2-[1-(3-(3,4-Dimethoxyphenyl)propan-1-ol)-3'-phenoxy]ethyl ether (100 mg, 0.155 mmol) in CH$_2$Cl$_2$ (2.0 mL) at 0° C. was treated with (2S)-1-(2S)-(3,4,5-trimethoxyphenyl)butyryl)-2-piperidinecarboxylic acid (181 mg, 0.495 mmol) followed by 4-(dimethylamino)-pyridine (2 mg) and 1,3-dicyclohexylcarbodiimide (102 mg, 0.495 mmol). The resulting bright yellow suspension was allowed to warm to room temperature and stir for 16 h after which time was diluted with EtOAc (5 mL) and filtered through a plug of Celite. The evaporated residue was chromatographed (silica gel, 5% EtOAc/hexanes) to afford product (101 mg, 49%) as a colorless foam: TLC (MeOH/CHCl$_3$, 5:95) Rf=0.38; IR (neat) 2940, 1740, 1645, 1590, 1515, 1455, 1240, 1130, 1030 cm$^{-1}$; MS(ES+): (M+NH$_4$)$^+$ 1358, (M+Na)$^+$ 1363.

(R) 1-(3-(Carboxymethoxy)phenyl)-3-(3,4-dimethoxyphenyl)propan-1-ol

A solution of (R) 1-(3-(tert-Butoxycarbonylmethoxy)phenyl)-3-(3,4-dimethoxyphenyl)propan-1-ol (13) (5.0 g, 12.5 mmol) in CH$_2$Cl$_2$ (25 mL) was cooled to 0° C. and treated with trifluoroacetic acid (10 mL). The reaction mixture was allowed to warm to room temperature and stir for 1 h after which time the mixture was evaporated and treated twice with benzene (30 mL) and evaporated to remove traces of trifluoroacetic acid. The crude material was placed on a vacuum pump for 4 h and then triturated with diethyl ether to afford product (3.4 g, 79%) as a white solid: IR (neat) 2935, 1745, 1680, 1590, 1515, 1445, 1260, 1155, 1025 cm$^{-1}$; $^1$H NMR (CDCl$_3$, 300 MHz) 9.54 (br s, 1H), 7.57 (d, J=7.7 Hz, 1H), 7.48 (s, 1H), 7.36 (d, J=8.0 Hz, 1H), 7.14-7.10 (m, 1H), 6.77-6.74 (m, 3H), 4.70 (s, 2H), 3.84 (m, 3H), 3.82 (m, 3H), 3.24 (t, J=7.3 Hz, 1H), 2.98 (t, J=7.8 Hz, 1H); $^{13}$C NMR (CDCl$_3$, 75 MHz) 199.6, 173.6, 1582, 149.3, 147.9, 138.8, 134.2, 130.3, 122.4, 120.7, 120.4, 113.7, 112.4, 112.0, 65.2, 56.4, 56.3, 41.1, 302; MS (ES+): (M+H)$^+$ 345, (M+Na)$^+$ 367; (ES-): (M-H)$^-$ 343.

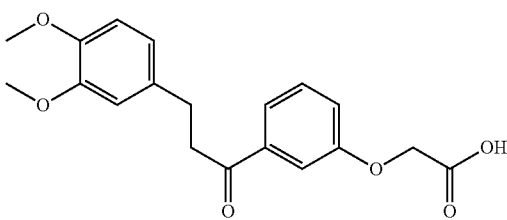 [SMILES: COc1ccc(CCC(=O)c2cccc(OCC(=O)O)c2)cc1OC]

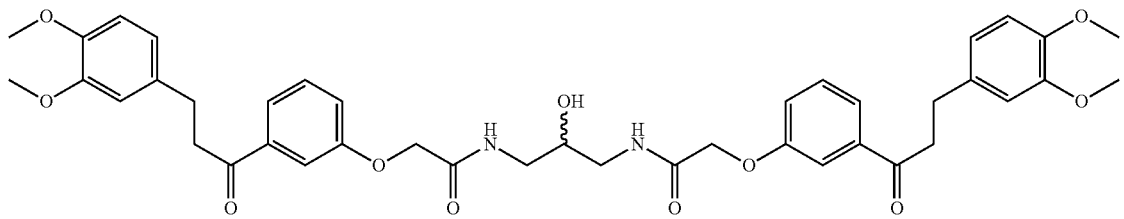

A solution of the previous acid (500 mg, 1.45 mmol) in CH$_2$Cl$_2$ (2.0 mL) at 0° C. was treated with 4-(dimethylamino)-pyridine (2 mg) followed by 1,3-dicyclohexylcarbodiimide (329 mg, 1.60 mmol). The resulting suspension was allowed to stir for 15 min then treated with a CH$_2$Cl$_2$ (2.0 mL) solution of 1,3-diamino-2-propanol (52.3 mg, 0.581 mmol). The reaction mixture was allowed to warm to room temperature and stir for 2 h after which time the reaction was diluted with EtOAc (10 mL) and filtered through a plug of Celite. The evaporated residue was chromatographed (silica gel, 100% EtOAc Æ 5% MeOH/EtOAc) to afford product (299 mg, 69%): TLC (EtOAc) Rf=0.35; IR (neat) 3355, 2930, 1680, 1515, 1440, 1260, 1155, 1030 cm$^{-1}$; $^1$H NMR (CDCl$_3$, 300 MHz) 7.56 (d, J=7.7 Hz, 2H), 7.47 (d, J=7.5 Hz, 2H), 7.36 (t, J=8.0 Hz, 2H), 7.26 (d, J=6.1 Hz, 2H), 7.11 (d, J=8.0, 2.5 Hz, 2H), 6.75-6.73 (m, 6H), 4.50 (s, 4H), 3.82 (s, 6H), 3.81 (br, 1H), 3.80 (s, 6H), 3.43-339 (m, 4H), 3.22 (t, J=7.3 Hz, 4H), 2.96 (t, J=7.7 Hz, 4H); $^{13}$C NMR (CDCl$_3$, 75 MHz) 199.2, 169.8, 157.8, 149.4, 147.9, 139.0, 134.1, 130.4, 122.4, 120.6, 120.1, 114.1, 112.4, 111.9, 70.5, 67.7, 56.4, 56.3, 42.8, 41.2, 30.2; MS(ES+): (M+H)$^+$ 743; (ES-): (M-H)$^-$ 741.

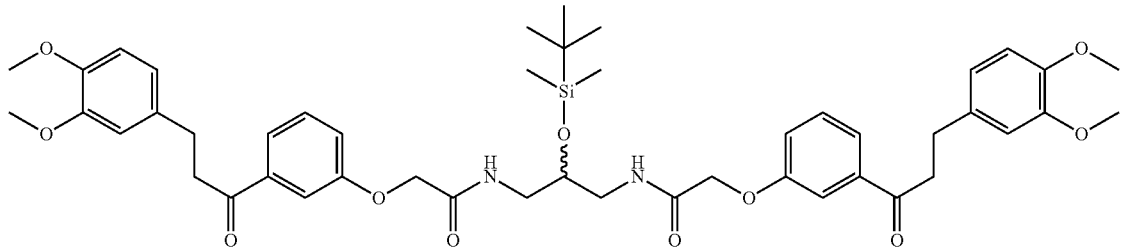

A solution of alcohol prepared above (950 mg, 1.28 mmol) in DMF (6.0 mL) was treated with imidazole (131 mg, 1.92 mmol) followed by tert-butyldimethylsilyl chloride (289 mg, 1.92 mmol) and allowed to stir for 3 h after which time an additional amount of imidazole (43 mg, 0.64 mmol) followed by tert-butyldimethylsilyl chloride (64 mg, 0.64 mmol) was added. The reaction mixture was stirred for a further 3 h and poured onto a biphasic mixture of EtOAc (25 mL) and water (50 mL). The organic layer was washed with a saturated aqueous NaCl solution (4×50 mL) then dried over NaSO$_4$, filtered, evaporated, and chromatographed (silica gel, 100% EtOAc Æ 5% MeOH/EtOAc) to afford product (709 mg, 65%) as well as recovered starting material (265 mg, 31%): TLC (EtOAc/hexanes, 3:1) Rf=0.56; IR (neat) 3440, 3355, 2935, 1680, 1590, 1515, 1440, 1260, 1155, 1030 cm$^{-1}$; $^1$H NMR (CDCl$_3$, 300 MHz) 7.53 (d, J=7.7 Hz, 2H), 7.46 (s, 2H), 7.33 (t, J=8.0 Hz, 2H), 7.09-7.05 (m, 4H), 6.72-6.70 (m, 6H), 4.47 (s, 4H), 3.87 (t, J=4.6 Hz, 6H), 3.79 (s, 6H), 3.77 (s, 6H), 3.60-3.52 (m, 2H), 3.19 (t, J=7.2 Hz, 4H), 3.05-2.99 (m, 2H), 2.94 (t, J=7.8 Hz, 4H), 0.80 (s, 9H), 0.30 (s, 6H); $^{13}$C NMR (CDCl$_3$, 75 MHz) 199.0, 168.6, 157.9, 149.4, 147.9, 139.0, 134.2, 130.4, 122.3, 120.6, 120.0, 114.1, 112.4, 111.9, 69.3, 67.7, 56.3, 41.9, 41.2, 30.2, 26.1, 18.3, −4.4; MS(ES+): (M+H)$^+$ 857, (M+NH$_4$)$^+$ 874; (ES−): (M−H)$^-$ 855.

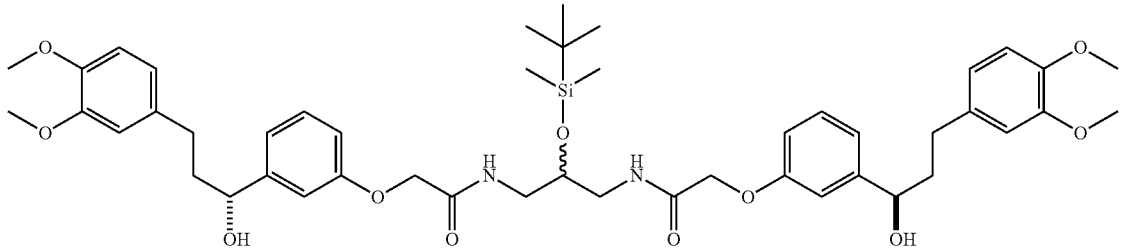

A solution of ketone (775 mg, 0.904 mmol) in THF (3 mL) at −20° C. was treated with a solution of (+)-b-chlorodiisopinocamphenylborane (1.16 g, 12.6 mmol) in THF (12 mL) at −20° C. The resulting mixture was allowed to stand in a −20° C. freezer for 64 h after which time the mixture was evaporated and treated with diethyl ether (20 mL) followed by diethanolamine (2 mL). The viscous mixture was allowed to stir at room temperature for 2 h followed by filtration through a pad of Celite with the aid of ethyl acetate. The cloudy filtrate was evaporated and flash chromatographed (silica gel, 75 Æ 100% EtOAc/hexanes) to afford product (487 mg, 63%) as a sticky solid: TLC (EtOAc/hexanes, 3:1) Rf=0.44; IR (neat) 3430, 2935, 1670, 1515, 1440, 1260, 1155, 1030 cm$^{-1}$; $^1$H NMR (CDCl$_3$, 300 MHz) 7.21-7.16 (m, 2H), 6.92-6.83 (m, 6H), 6.74-6.62 (m, 8H), 4.58 (dd, J=7.6, 5.3 Hz, 2H), 4.40 (s, 4H), 3.80 (br s, 1H), 3.76 (s, 6H), 3.75 (s, 6H), 3.44-3.33 (m, 2H), 3.01-2.92 (m, 2H), 2.68-2.48 (m, 4H), 2.03-1.85 (m, 4H), 0.79 (s, 9H), 0.00 (s, 6 H); $^{13}$C NMR (CDCl$_3$, 75 MHz) 169.3, 157.8, 149.3, 147.6, 134.8, 130.2, 120.6, 120.2, 114.0, 112.6, 112.5, 111.8, 106.8, 73.8, 69.2, 67.7, 56.3, 56.2, 41.9, 41.1, 32.1, 26.1, 18.3, −4.4; MS(ES+): (M+H)$^+$ 861.

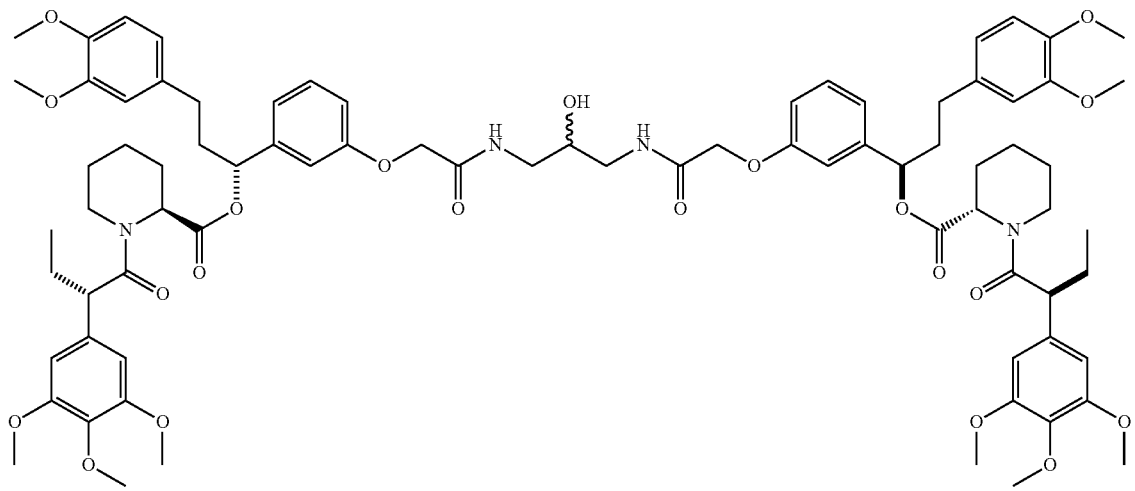

A solution of alcohol (100 mg, 0.116 mmol) in CH$_2$Cl$_2$ (3.0 mL) at 0° C. was treated with (2S)-1-((2S)-(3,4,5-trimethoxyphenyl)butyryl)-2-piperidinecarboxylic acid (136 mg, 0.371 mmol) followed by 4-(dimethylamino)-pyridine (2 mg) and 1,3-dicyclohexylcarbodiimide (77 mg, 0.371 mmol). The resulting suspension was allowed to stir for 16 h then diluted with EtOAc (5 mL) and filtered through a plug of Celite. The evaporated residue was chromatographed (silica gel, EtOAc) to afford product (68 mg, 38%) as a colorless foam: TLC (EtOAc/hexanes, 3:1) Rf=0.26, (MeOH/EtOAc, 3:97) Rf=0.39; IR (neat) 3440, 2935, 1740, 1680, 1645, 1590, 1515, 1455, 1260, 1130, 1030 cm$^{-1}$.

The ester (65 mg, 0.418 mmol) in acetonitrile (1.5 mL) at 0° C. was treated with a 5% HF/acetonitrile solution (1 mL) and allowed to warm to room temperature and stir for 30 min. The reaction mixture was poured onto a biphasic mixture of EtOAc (15 mL) and a saturated aqueous NaHCO$_3$ solution (10 mL). The organic portion was washed with an additional amount of base followed by a saturated aqeuous NaCl solution (2×10 mL). The organic solution was then dried over MgSO$_4$, filtered, evaporated, and chromatographed (silica gel, EtOAc Æ 3% MeOH/EtOAc) to afford product (38 mg, 68%) as a colorless foam: TLC (MeOH/ethyl acetate, 3:97) Rf=0.24; IR (neat) 3360, 2940, 1740, 1645, 1590, 1515, 1455, 1240, 1130, 1030 cm$^{-1}$; MS(ES+): (M+H)$^+$ 1441, (M+NH$_4$)$^+$ 1458, (M+Na)$^+$ 1463.

Synthesis of 4-nitrophenyl N-2-pentylcarbamate

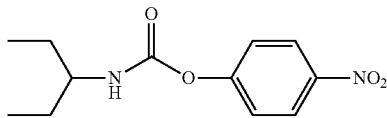

To a stirred solution of 4-nitrophenylchloroformate (597 mg, 2.84 mmol) in CH$_2$Cl$_2$ (5 mL) was added dropwise ethyl propylamine (330 mL, 2.84 mmol). The resulting white suspension was allowed to stir overnight. The reaction mixture was then diluted with CH$_2$Cl$_2$ (25 mL), washed with Sat. NaHCO$_3$ (2×20 mL) and brine, and dried over anhydrous MgSO$_4$. The solvent was evaporated to give 645 mg white solid. $^1$H NMR (CDCl$_3$, 300 MHz) 8.23 (d, J=9.1 Hz, 2H), 7.32 (d, J=9.1 Hz, 2H), 4.82 (m, 1H), 3.52-3.62 (m, 1H), 1.40-1.71 (m, 4H), 0.98 (t, J=7.4 Hz, 6H).

(1R)-3-(3,4-Dimethoxyphenyl)-1-[3-(t-butoxycarbonylmethoxy)phenyl]-1-propyl (2S)-1-(1'-ethylpropyl-carbamoyl)-2-piperidinecarboxylate

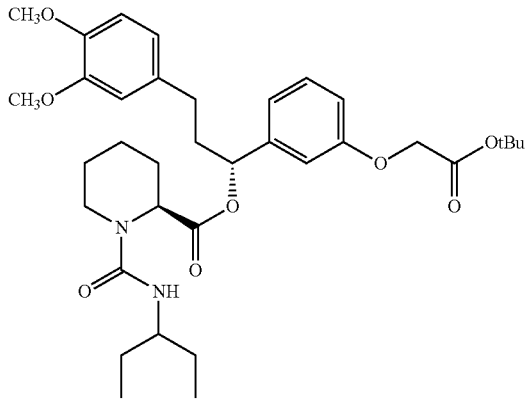

A solution of the amine (300 mg, 0.585 mmol) in CH$_2$Cl$_2$ (3 mL) was treated with the carbamate (184 mg, 0.702 mmol) followed by NEt$_3$ (163 mL, 1.17 mmol). The resulting bright yellow solution was allowed to stir overnight. The reaction mixture was concentrated and flash chromatographed (silica gel, 33% EtOAc/hexanes) to afford 209 mg (57%) of a white foam: $^1$H NMR (CDCl$_3$, 300 MHz) 7.25 (t, J=7.9 Hz, 1H), 6.90 (s, 1H), 6.81 (d, J=8.3 Hz, 1H), 6.77 (d, J=8.7 Hz, 1H), 6.67 (m, 2H), 5.76 (dd, J=7.3, 6.1 Hz, 1H), 5.05 (d, J=3.5 Hz, 1H), 4.52 (s, 2H), 4.35 (d, J=8.4 Hz, 1H), 3.86 (s, 3H), 3.84 (s, 3H), 3.68 (m, 1H), 3.54 (bd, J=11.3 Hz, 1H), 3.09 (dt, J=2.6, 12.3 Hz, 1H), 2.51-2.59 (m, 2H), 2.18-2.30 (m, 2H), 2.03-2.09 (m, 1H), 1.31-1.69 (m, 9H), 1.48 (s, 9H), 0.88 (t, J=7.3 Hz, 6H); $^{13}$C NMR (CDCl$_3$, 75 MHz) 172.22, 168.34, 158.77, 158.40, 149.17, 147.61, 142.17, 133.96, 129.96, 120.51, 120.20, 114.28, 113.63, 112.10, 111.62, 82.72, 76.19, 66.12, 56.26, 56.18, 54.21, 53.50, 42.27, 38.41, 31.48, 28.40, 28.10, 25.18, 20.98, 10.62. MS(FAB): (M+H)$^+$: 627.50.

(1R)-3-(3,4-Dimethoxyphenyl)-1-[3-(hydroxycarbonylmethoxy)phenyl]-1-propyl (2S)-1-(1'-ethylpropyl-carbamoyl)-2-piperidinecarboxylate

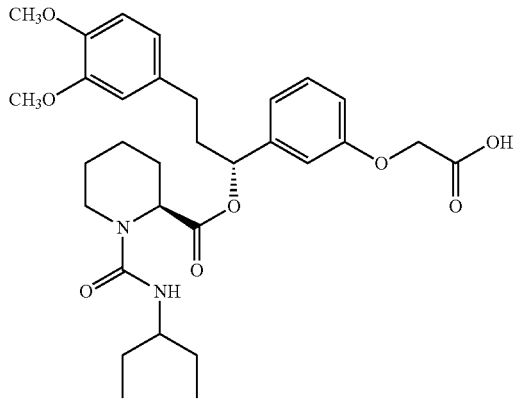

A solution of the above t-butyl ester (209 mg, 0.33 mmol) in CH$_2$Cl$_2$ (6 mL) was treated with trifluoroacetic acid (1.29 mL, 16.5 mmol) and the mixture was stirred at room temperature for 2 hours. The reaction mixture was diluted with toluene (50 mL) and concentrated and flash chromatographed (silica gel, 100% EtOAc with 2% HOAc) to afford 163 mg (86%) of the acid as a white solid: $^1$H NMR (CDCl$_3$, 300 MHz) 7.41 (br, 1H), 7.22 (t, J=7.8 Hz, 1H), 6.68-6.96 (m, 6H), 5.69 (dd, J=5.2, 8.3 Hz, 1H), 5.13 (d, J=4.0 Hz, 1H), 4.60 (d, J=4.7 Hz, 2H), 4.43 (br, 1H), 3.86 (s, 3H), 3.84 (s, 3H), 3.60-3.73 (m, 1H), 3.46 (bd, J=9.0 Hz, 1H), 3.17 (dt, J=3.0, 12.1 Hz, 1H), 2.50-2.69 (m, 2H), 2.99-2.33 (m, 3H), 1.22-1.82 (m, 9H), 0.86 (t, J=7.4 Hz, 3H), 0.80 (t, J=7.4 Hz, 3H); $^{13}$C NMR (CDCl$_3$, 75 MHz) 172.09, 171.86, 159.16, 158.52, 149.34, 147.79, 142.43, 133.94, 129.95, 120.60, 119.91, 115.82, 112.19, 111.84, 110.99, 76.58, 65.92, 56.33, 56.27, 54.29, 53.81, 42.21, 38.49, 31.86, 27.82, 27.39, 25.09, 23.02, 20.90, 10.49. MS(FAB): (M−H)$^-$: 569.48.

Assay of Binding of Bumped Synthetic FKBP Ligands to FKBP Mutants Bearing Compensatory Mutations Affinities of bumped synthetic ligands for FKBP were determined using a competitive assay based on fluorescence polarization (FP). A fluorescein-labelled FK506 probe (4) was synthesized, and the increase in the polarization of its fluorescence used as a direct readout of % bound probe in an equilibrium binding experiment containing sub-saturating FKBP and variable amounts of bumped ligand as competitor. The assay yields IC50 values that are related to the affinity of the competitive ligand for the protein.

(i) Synthesis of Fluoresceinated FK506 Probe (4)
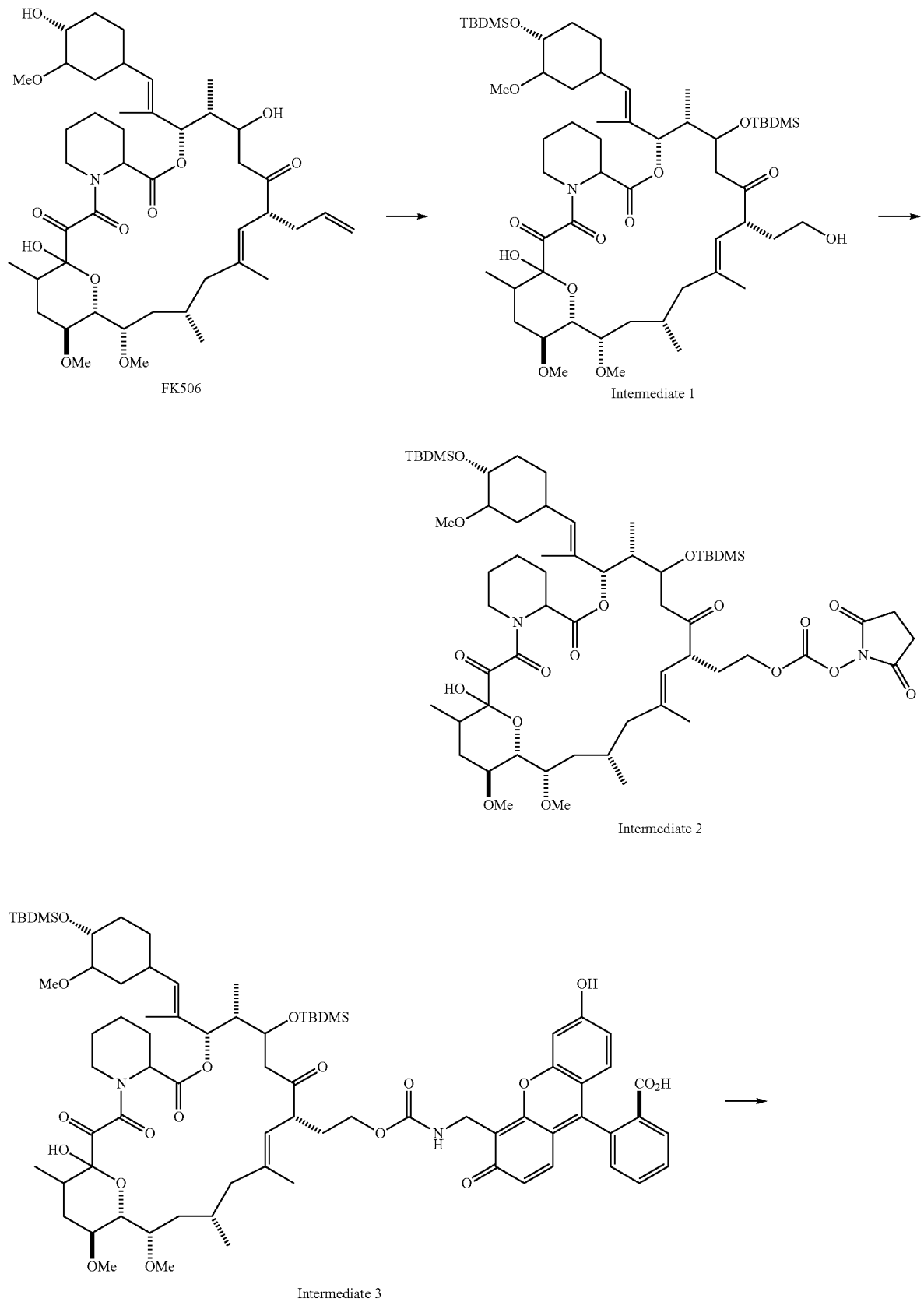

-continued

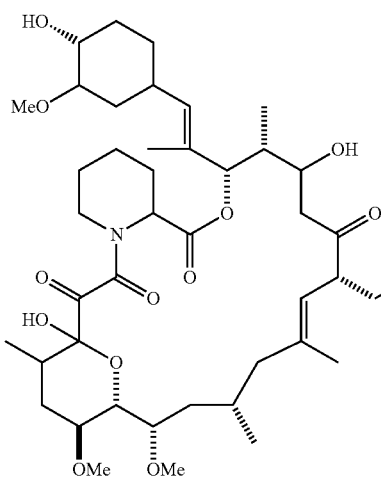

Intermediate 4

24,32-Bis(tert-Butyldimethylsilyl)ether of FK506 tert-Butyldimethylsilyl trifluoromethanesulfonate (108 μL, 470 μmol) was added dropwise to a stirred solution of FK506 (103 mg, 128 μmol) and 2,6-lutidine (89.5 μL, 768 μmol) in dichloromethane (3 mL) at 0° C. The resulting solution was stirred at 0° C. for 2 h, and then treated with MeOH (0.5 mL) and ether (15 mL). The mixture was washed with 10% aqueous NaHCO$_3$ (3 mL) and brine (3 mL). The organic layer was decanted, dried over anhydrous Na$_2$SO$_4$, filtered, and concentrated to a yellow oil. Column chromatography (silica-gel, hexanes-EtOAc 3:1) gave the title compound as a colorless oil (104 mg).

Intermediate 1

To a solution of 24,32-bis(tert-butyldimethylsilyl)ether of FK506 (100 mg, 97 μmol) in THF (2.5 mL) was added morpholine N-oxide (68 mg, 580 μmol), followed by water (60 μL), and a 4% aqueous solution of osmium tetroxide (123 μL, 20 μmol). The resulting mixture was stirred at room temperature for 4.5 h. It was then treated with 50% aqueous MeOH (1.5 mL) and sodium periodate (207 mg, 970 μmol), and the suspension stirred for an additional 1 h. The mixture was diluted with ether (10 mL) and washed with saturated aqueous NaHCO$_3$ (2×4 mL). The organic layer was decanted, dried over anhydrous sodium sulfate containing a small amount of sodium sulfite, filtered, and concentrated. The residue was dissolved in anhydrous THF (2.8 mL), cooled to −78° C. under nitrogen, and treated with a 0.5 M solution of lithium tris[(3-ethyl-3-pentyl)oxy]aluminum hydride in THF (282 μL). The resulting solution was stirred at −78° C. for 1.75 h, and then quenched by addition of ether (6 mL) and saturated ammonium chloride solution (250 μL). The mixture was allowed to warm up to room temperature and treated with anhydrous sodium sulfate. Filtration and concentration under reduced pressure afforded a pale yellow oil (97 mg), which was purified by column chromatography (silica-gel, hexanes-EtOAc 3:1) to afford 1 as a colorless oil.

Intermediate 2

A solution of the above alcohol (300 mg, 290 μmol) in acetonitrile (10 mL) was treated with 2,6-lutidine (338 μL, 2.9 mmol) and N,N'-disuccinimidylcarbonate (371 mg, 1.45 mmol). The resulting suspension was stirred at room temperature for 14.5 h, and then concentrated under reduced pressure. The residue was chromatographed (silica-gel, hexanes-EtOAc 2:1 to 100% EtOAc gradient) to afford the mixed carbonate 2 as a pale yellow oil (127 mg).

Intermediate 3

A solution of the above carbonate (30 mg, 26 μmol) and triethylamine (36 μL, 260 μmol) in acetonitrile (1 mL) was treated with 4'-(aminomethyl)fluorescein (13.5 mg, 34 μmol). The resulting bright orange suspension was stirred at room temperature for 1 h, and then concentrated under reduced pressure. The residue was chromatographed (silica-gel, hexanes-EtOAc 1:1 to 100% EtOAc to EtOAc-MeOH 1:1 gradient) to give 3 (20.5 mg) as a bright yellow solid.

Intermediate 4

A solution of bis-silyl ether 3 (35 mg, 25 μmol) in acetonitrile (2 mL) was treated with 48% (w/w) HF in water (250 μL). The resulting mixture was stirred at room temperature for 5.5 h. It was then diluted with dichloromethane (10 mL) and washed with water (2×2 mL). The organic layer was decanted, dried over anhydrous sodium sulfate, and concentrated under reduced pressure. The residue was chromatographed (silica-gel, 100% EtOAc) to afford 4 (13 mg) as a bright yellow solid.

(ii) Determination of Sub-Saturating Concentration of FKBP Mutant by Direct Binding Genes encoding mutant FKBPs were engineered using standard methods [F. M. Ausubel et al., Eds., Current Protocols in Molecular Biology (John Wiley & Sons, New York, 1994)]. Recombinant pure wild-type and mutant FKBPs were expressed and purified by standard methods (see eg. Wiederrecht, G. et al. 1992. *J. Biol. Chem.* 267, 21753-21760).

For competition FP assays, the appropriate protein concentration (giving ~90% binding of probe) was first determined by direct binding of probe to protein (see eg. Beacon FP System Applications Guide, Panvera Corp, Madison, Wis.). All binding assay procedures were performed at room temperature. Serial dilutions of each protein were prepared in 50 mM potassium phosphate pH 7.8/150 mM NaCl/100 µg/ml bovine gamma globulin ("FP buffer": prepared using only low-fluorescence reagents from Panvera), and 100 µl volumes transferred to wells of a Dynatech micro-fluor black 96-well fluorescence plate. 100 µl of 10 nM 4 in FP buffer plus 2% ethanol (prepared from an ethanol stock of the probe) was then added to each well with mixing. Duplicate control wells contained FP buffer instead of FKBP (for 0% probe binding) or 10 µM wild-type FKBP (for 100% binding).

The plates were stored covered in the dark for approximately 30 min to permit equilibration and then the fluorescence polarization of the sample in each well was read on a Jolley FPM-2 FP plate reader (Jolley Consulting and Research, Inc., Grayslake, Ill.) in accordance with the manufacturer's recommendations. Polarization (mP units) for each protein concentration was plotted (y axis) vs. final concentration of FKBP (x axis). Concentrations were determined by OD280 measurements. Arbitrary units were used for non-quantitated proteins. Non-linear least square analysis was used to fit the curve and extract the $K_d$ of the protein for the probe (in cases where the protein concentration was known) using the following four-parameter equation:

$$y=M3+(((x+M1+M2)-\text{SQRT}(((x+M1+M2)^2)-(4*x*M1)))/(2*(M1)))*(M4-M3)$$

where M1 is the probe concentration, M2 the $K_d$, and M3 and M4 the minimum and maximum mP values respectively. The M3 and M4 fitted values were used to calculate the concentration of FKBP mutant that gives 90% probe binding, and this value was then used in subsequent competition experiments.

(iii) Determination of Binding Affinities (IC50s) of Synthetic FKBP Ligands Using Competition FP Serial 10-fold dilutions of each synthetic ligand were prepared in 100% ethanol in glass vials and stored on ice. All other manipulations were performed at room temperature. Purified recombinant wild-type or mutant FKBP was diluted to (200/98)×the concentration predetermined to give 90% probe binding, and 98 µl aliquots transferred to wells of a Dynatech micro-fluor black 96-well fluorescence plate. 2.0 µl samples of the synthetic ligands were then transferred in duplicate to the wells with mixing. Finally, a probe solution was prepared containing 10 nM 4 in 0.1% ethanol/FP buffer, and 100 µl added to each well with mixing. Duplicate control wells contained ethanol instead of FKBP ligand (for 100% probe binding) or ethanol instead of FKBP ligand and FP buffer instead of FKBP (0% binding).

The plates were stored covered in the dark for approximately 30 min to permit equilibration and then the fluorescence polarization of the sample in each well read on a Jolley FPM-2 FP plate reader (Jolley Consulting and Research, Inc., Grayslake, Ill.) in accordance with the manufacturer's recommendations. The mean polarization (mP units) for each competitor concentration, in some cases converted to % total binding by reference to the control values, was plotted (y axis) vs. log molar final concentration of competitor (x axis). Non-linear least square analysis was used to fit the curve and extract the IC50 using the following equation:

$$y=M1+(M4-M1)/(1+\exp(M2*(M3-x)))$$

where M3 is the IC50. For incomplete curves the IC50 was determined by interpolation. FK506 was included as a control in each case.

Cell-Based Transfection Assay

Dimerizers may also be assayed for their ability to activate transcription of a reporter gene linked to a regulatory sequence responsive to the dimerization of FKBP-containing fusion proteins containing one or more transcription regulatory domains (e.g. DNA binding domains and transcription activation domains). We have made use of such as system as follows. Human 293 cells were transiently transfected by calcium phosphate procedure with plasmids PCGNNGF3 and PCGNNF3VP16, expressing Gal4 DNA binding domain (aa 1-147) fused to 3 copies of FKBP12 and 3 copies of FKBP12 fused to the VP16 activation domain (aa 411-490), respectively. The reporter plasmid (G51L2-SEAP) used in these assays contains a gene that encodes for secreted alkaline phosphatase (SEAP) under the control of the minimal IL2 promoter and 5XGAL4 binding sites placed upstream of the promoter. In all cases, a plasmid expressing growth hormone was used as an internal control to moniter transfection efficiency.

Approximately, 16 hrs after transfection, the media was removed and the cells were washed twice with PBS. Cells were refed with 2.5 ml of DMEM containing 10% serum and two hours later, synthetic dimerizers were added directly to the medium at appropriate concentrations in 5 ul of ethanol carrier solution. Approximately, 24 hrs after the addition of the drugs, 100 ul of the media was removed and assayed for SEAP activity and another 100 ul of the media was used to assay for growth hormone activity (to normalize for transfection efficiency).

Results for a sample of our multimerizers in that system are shown below (see Dimerizer Assay Worksheet) at multimerizer concentrations from 0.1 to $10^4$ nM, as indicated, normalized for hGH expression, and expressed as a % of maximal transcriptional activity observed with the prototype multimerizer, FK1012 (see Spencer et al, Science, supra).

Analogous assays have also been conducted using cell lines such as 1080 cells in place of 293 cells; activation domains such as the NF-kB p65 activation domain in place of VP16; and the composite DNA binding domain, ZFHD1 (see Pomerantz, J. L., et al. 1995. *Science.* 267:93-96.) in place of GALA (with the reporter gene linked to a DNA sequence recognized by ZFHD1 in place of a GALA site).

It should be appreciated that multimerizers of this invention will vary somewhat in their observed activity, depending on the particular chimeric proteins and other components of such systems. We recommend that the practitioner select multimerizers based on their performance in the particular system of interest.

Dimerizer-Dependent Activation of Signal Transduction

Many cellular receptors can be activated by aggregation, either by their physiological ligand or by anti-receptor antibodies. Such aggregation of two proteins can often trigger a specific intracellular signal. One of the uses of multimerizers of this invention is to trigger activation of a receptor effector domain by oligomerizing fusion proteins containing such effector domains together with ligand-binding domains (such as FKBP domains) capable of binding to the multimerizing agent. Preferably, the FKBP domains are modified or selected to permit selective binding with a "bumped" multimerizing agent, i.e., containing at least one monomeric constituent M of formula II, even in the presence of endogenous, wild-type FKBP moieties in the cells to be treated. One example of an effector domain is the intracellular domain of Fas. Such domains have been incorporated into fusion proteins which also contain one or more FKBP domains and which are anchored to the cell membrane through a transmembrane protein anchor or through lipid modification of the protein(s), such as myristoylation.

Two examples of the use of bumped dimerizer in signal transduction are to trigger receptor tyrosine kinase activation and to trigger apoptosis via Fas activation, which is discussed below. Unless otherwise mentioned all DNA manipulations were performed following standard procedures (F. M. Ausubel et al., Eds., Current Protocols in Molecular Biology, John Wiley & Sons, New York, 1994) and all protein protocols were performed following standard procedures (Harlow, E. and Lane, D. 1988. Antibodies, a Laboratory Manual. Cold Spring Harbor Laboratory, Cold Spring Harbor). All PCR products used to make constructs were confirmed by sequencing. For additional information and guidance in this regard, see the international patent applications cited infra.

A. Constructs Encoding Chimeric Proteins that Include Domain(s) of Fas

The ability to control Fas activation and trigger apoptosis via a small molecule has applications both in gene therapy, where it may be used to selectively eliminate engineered cells, and in experimental systems. The proteins described here are anchored to the membrane by either of two methods: (1) by a myristoylation sequence or (2) via the low affinity NGF receptor, also called p75, p75 is useful experimentally because of the availability of antibodies to its extracellular domain, and its lack of high affinity interaction with any identified ligand (Bothwell, M. 1995. Annu. Rev. Neurosci. 18:223-253), but another protein anchor could substitute.

1. Construction of Expression Vectors Encoding Chimeric Dimerizable Construct.

The construction of the expression vectors encoding one or more FKBPs and a myristoylaton domain or p75 domain and a Fas effector domain are described in detail in published international patent application WO 96/41865. Conventional subcloning techniques were used to substitute modified FKBPs into these constructs (in place of wt FKBP domains) and derivatives thereof.

2. Assay of Rapamycin-Mediated Fas Activation in Cell Lines

The ability of a dimerizer to activate the Fas signal transduction pathway and trigger cell death in cells engineered to express a FAS-FKBP fusion can be tested in cells appropriately transduced by retroviral vectors to express the desired fusion protein. A retroviral vector containing DNA encoding the construct of interest is used to make transducing supernatants by co-transfection via calcium phosphate precipitation of the vector DNA and DNA encoding proteins required for retroviral packaging (Muller et al., 1991, Molecular Cell. Biol. 11, 1785-1792). Alternatively, stable packaging cell lines can be transfected with the retroviral vector to generate retroviral vector supernatants. The retroviral supernatant is used to transduce target cells. To screen compounds and constructs, we used the human fibrosarcoma line HT1080. Two to three days after transfection, cells are plated into G418 and the resistant population or clones are isolated by standard means. To monitor dimerizer-induced apoptosis, cells are plated into a 96-well plate at either 5000 or 10,000 cells/well in MEM medium containing 10% fetal bovine serum. The next day, medium removed and replaced with fresh medium containing the test compound at various dilutions, in triplicate. In some cases, Actinomycin D is included at 50 ng/ml. Untreated wells are always included. The next day, medium is removed and replaced with medium containing 10% Alamar Blue viability indicator, which changes absorbance properties as a function of reducing agent released into the medium by cell metabolism. Alternatively, cells are counted. Optical density at the appropriate wavelength is measured using a platereader spectroscope. Results are normalized to the signal obtained by untreated wells (100%), and EC50 values determined. A control cell line that has been retrovirally transduced with vector alone is also tested as a control for any killing not due to the drug. Results from such assays are set forth in the Synthetic Multimerizers Table, infra. Cell populations and clones vary in the proportion of cells responsive to Fas, depending on the clone and the construct. Variations that work well can be readily identified.

As an alternative method for monitoring cell death, cells expressing a construct containing p75 followed by 2 mutant FKBPs followed by a Fas effector domain were transfected using an episomal vector, pCEP4 (Invitrogen Corp.) into which we had inserted DNA encoding hGH under control of a CMV promoter. The vector confers resistance to hygromycin. Clones resistant to hygromycin were selected and tested for response to dimerizer and expression of hGH after treatment with a dimerizer, AP1903. Monitoring Alamar Blue or hGH levels led to very similar EC50 curves for cell viability (measured as a % of control value) plotted against dimerizer concentration. In both cases the concentration of dimerizer corresponding to 50% of control was less than 1 nM.

3. Assay of Dimerizer-Induced Apoptosis in Animals

HT1080 cells expressing hGH and a Fas-FKBP construct as described above were harvested in PBS containing 10 mM EDTA plus 0.1% glucose, then washed and resuspended in PBS containing 0.1% bovine serum albumin plus 0.1% glucose. They were injected intramuscularly into nude mice in a volume of 100 ul, $2 \times 10^6$ cells/mouse. The next day, the mice received an intravenous injection of compound or vehicle. The next day and days following, blood samples were obtained and hGH was measured. Three multimerizers of this invention (of formula IV above) which were thus tested were found to decrease circulating hGH by 50% at the following doses: 0.2+/−0.01 mg/kg; 0.5+/−0.2 mg/kg; 2+/−1 mg/kg (number of experiments $\geq 2$ in all cases) as calculated from estimated initial plasma concentrations immediately after the injection. These results are consistent with effective cell killing, i.e., effective mediation of protein-protein interaction between the fusion proteins in the engineered cells within the mice.

The invention claimed is:

1. A compound of the formula

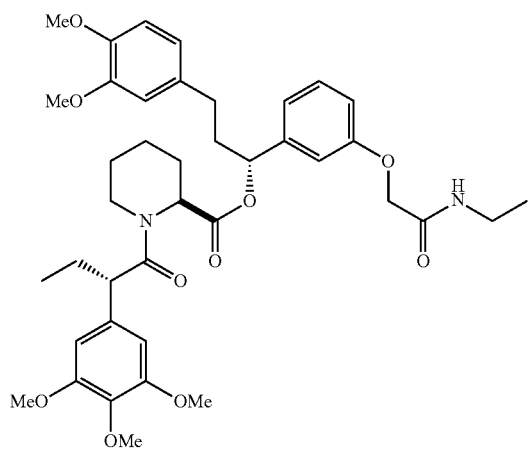

-continued
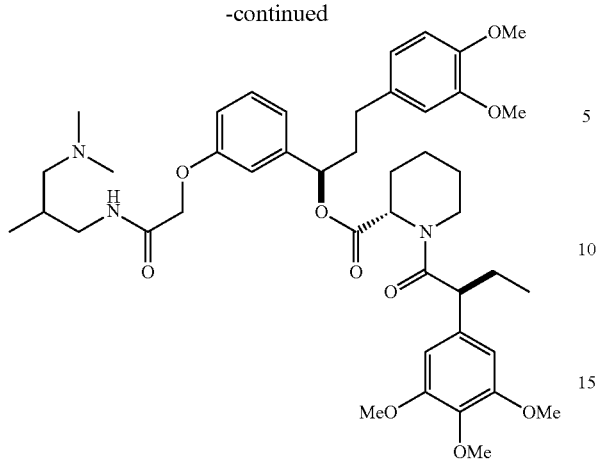
or a salt thereof.
2. A compound of the formula
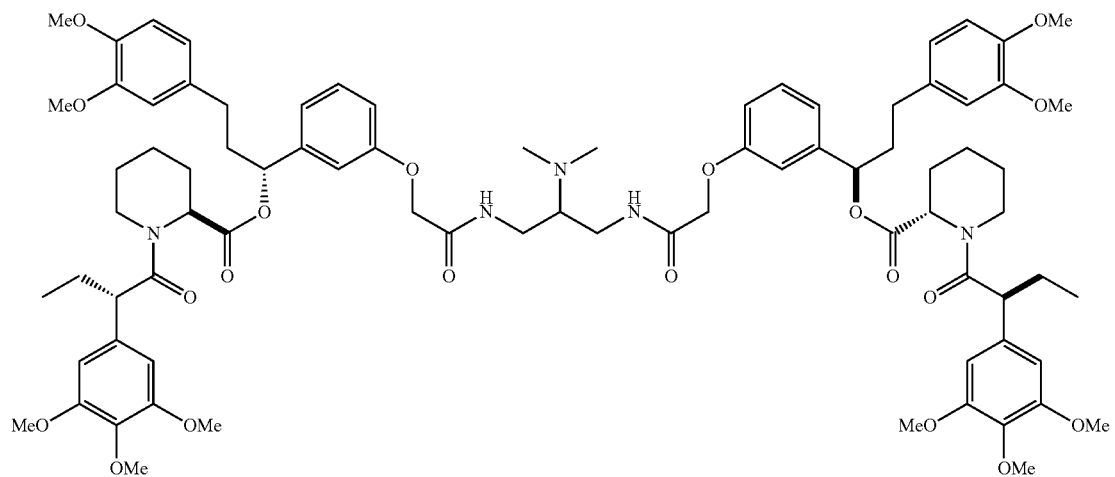
or a salt thereof.
* * * * *